US010597715B2

(12) United States Patent
Zhou et al.

(10) Patent No.: US 10,597,715 B2
(45) Date of Patent: Mar. 24, 2020

(54) METHODS FOR SEQUENCING NUCLEIC ACIDS

(71) Applicant: CENTRILLION TECHNOLOGY HOLDINGS CORPORATION, Grand Cayman (KY)

(72) Inventors: Wei Zhou, Saratoga, CA (US); Filip Crnogorac, Palo Alto, CA (US); Glenn McGall, Palo Alto, CA (US); Jian Cao, Sunnyvale, CA (US)

(73) Assignee: Centrillion Technology Holdings, Grand Cayman (KY)

( * ) Notice: Subject to any disclaimer, the term of this patent is extended or adjusted under 35 U.S.C. 154(b) by 904 days.

(21) Appl. No.: 15/100,919

(22) PCT Filed: Dec. 5, 2014

(86) PCT No.: PCT/US2014/068954
§ 371 (c)(1),
(2) Date: Jun. 1, 2016

(87) PCT Pub. No.: WO2015/085274
PCT Pub. Date: Jun. 11, 2015

(65) Prior Publication Data
US 2016/0369334 A1  Dec. 22, 2016

Related U.S. Application Data

(60) Provisional application No. 61/912,027, filed on Dec. 5, 2013, provisional application No. 61/912,022, filed on Dec. 5, 2013, provisional application No. 61/912,559, filed on Dec. 6, 2013, provisional application No. 61/971,536, filed on Mar. 28, 2014, provisional application No. 61/971,542, filed on Mar. 28, 2014, provisional application No. 61/973,864, filed on Apr. 2, 2014, provisional application No. 61/979,431, filed on Apr. 14, 2014, provisional application No. 61/979,448, filed on Apr. 14, 2014, provisional application No. 61/984,057, filed on Apr. 25, 2014, provisional application No. 62/008,985, filed on Jun. 6, 2014, provisional application No. 62/012,238, filed on Jun. 13, 2014, provisional application No. 62/033,125, filed on Aug. 5, 2014.

(51) Int. Cl.
*C12Q 1/6874* (2018.01)
*C12Q 1/6837* (2018.01)

(52) U.S. Cl.
CPC ......... *C12Q 1/6874* (2013.01); *C12Q 1/6837* (2013.01)

(58) Field of Classification Search
None
See application file for complete search history.

(56) References Cited

U.S. PATENT DOCUMENTS

| 4,469,863 A | 9/1984 | Ts'o et al. |
|---|---|---|
| 4,988,617 A | 1/1991 | Landegren et al. |
| 5,034,506 A | 7/1991 | Summerton et al. |
| 5,216,141 A | 6/1993 | Benner |
| 5,235,033 A | 8/1993 | Summerton et al. |
| 5,242,794 A | 9/1993 | Whiteley et al. |
| 5,386,023 A | 1/1995 | Sanghvi et al. |
| 5,476,930 A | 12/1995 | Letsinger et al. |
| 5,478,893 A | 12/1995 | Ghosh et al. |
| 5,494,810 A | 2/1996 | Barany et al. |
| 5,602,240 A | 2/1997 | De Mesmaeker et al. |
| 5,637,684 A | 6/1997 | Cook et al. |
| 5,644,048 A | 7/1997 | Yau |
| 5,712,124 A | 1/1998 | Walker |
| 5,750,341 A | 5/1998 | Macevicz |
| 5,780,613 A | 7/1998 | Letsinger et al. |
| 5,795,714 A | 8/1998 | Cantor et al. |
| 5,969,119 A | 10/1999 | Macevicz |
| 6,262,216 B1 | 7/2001 | McGall |
| 6,306,597 B1 | 10/2001 | Macevicz |
| 6,410,278 B1 | 6/2002 | Notomi et al. |
| 6,511,803 B1 | 1/2003 | Church et al. |
| 6,582,938 B1 | 6/2003 | Su et al. |
| 6,692,914 B1 | 2/2004 | Klaerner et al. |
| 6,994,964 B1 | 2/2006 | Chang et al. |
| 7,048,481 B2 | 5/2006 | Sugata et al. |
| 7,170,050 B2 | 1/2007 | Turner et al. |
| 7,211,390 B2 | 5/2007 | Rothberg et al. |
| 7,244,559 B2 | 7/2007 | Rothberg et al. |
| 7,244,567 B2 | 7/2007 | Chen et al. |
| 7,250,253 B1 | 7/2007 | Klapproth et al. |

(Continued)

FOREIGN PATENT DOCUMENTS

| CN | 102224257 A | 10/2011 |
|---|---|---|
| EP | 1291354 A2 | 3/2003 |

(Continued)

OTHER PUBLICATIONS

Akeroyd, et al. The combination of living radical polymerization and click chemistry for the synthesis of advanced macromolecular architectures. European Polymer Journal. 2011; 47.6: 1207-1231.
Allemand, J. F., Bensimon, D., Jullien, L., Bensimon, A. & Croquette, V. pH-dependent specific binding and combing of DNA. Biophys J 73, 2064-2070, (1997).
Anonymous. Topomize DNA library prep kit. Nov. 10, 2015.
"Sawai, H., Synthesis and properties of oligoadenylic acids containing 2-5-phosphoramide linkage. The chemical society of Japan. 1984.805-808."

(Continued)

*Primary Examiner* — Christopher M Gross
(74) *Attorney, Agent, or Firm* — Centrillion Technology Holdings Corporation

(57) ABSTRACT

Provided herein are methods and compositions for the sequencing of long nucleic acids, such as DNA. The methods and compositions are suited for the spatial labeling and sequencing of long nucleic acid molecules.

20 Claims, 46 Drawing Sheets

(56) References Cited

U.S. PATENT DOCUMENTS

| | | |
|---|---|---|
| 7,264,929 B2 | 9/2007 | Rothberg et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,405,281 B2 | 7/2008 | Xu et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,670,770 B2 | 3/2010 | Chou et al. |
| 7,713,689 B2 | 5/2010 | Chilkoti |
| RE42,315 E | 5/2011 | Lopez et al. |
| 8,367,314 B2 | 2/2013 | Chilkoti |
| 9,328,382 B2 | 5/2016 | Drmanac et al. |
| 2002/0068290 A1 | 6/2002 | Yarovinsky |
| 2002/0132245 A1 | 9/2002 | Boles et al. |
| 2003/0050438 A1* | 3/2003 | Montgomery ....... B01J 19/0046 530/334 |
| 2003/0082576 A1 | 5/2003 | Jones et al. |
| 2004/0171053 A1 | 9/2004 | Hu |
| 2004/0185260 A1 | 9/2004 | Luzinov et al. |
| 2005/0084912 A1 | 4/2005 | Poponin |
| 2005/0158879 A1 | 7/2005 | Klaerner et al. |
| 2005/0244863 A1 | 11/2005 | Mir |
| 2006/0205089 A1 | 9/2006 | Dratz et al. |
| 2008/0206764 A1 | 8/2008 | Williams et al. |
| 2009/0002935 A1 | 1/2009 | Cheng |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0068655 A1 | 3/2009 | Williams et al. |
| 2009/0121133 A1 | 5/2009 | Amirparviz |
| 2009/0181861 A1 | 7/2009 | Li et al. |
| 2009/0326208 A1 | 12/2009 | Carrino et al. |
| 2010/0022412 A1 | 1/2010 | Rigatti et al. |
| 2010/0173394 A1 | 7/2010 | Colston, Jr. et al. |
| 2010/0203597 A1 | 8/2010 | Chen et al. |
| 2010/0208724 A1 | 8/2010 | Booth et al. |
| 2010/0240827 A1 | 9/2010 | Barwick et al. |
| 2010/0268478 A1 | 10/2010 | Andregg et al. |
| 2011/0046324 A1 | 2/2011 | Matyjaszewski et al. |
| 2011/0143966 A1 | 6/2011 | McGall et al. |
| 2011/0143967 A1 | 6/2011 | McGall et al. |
| 2011/0172119 A1 | 7/2011 | Boutell |
| 2012/0004132 A1 | 1/2012 | Zhang et al. |
| 2012/0021200 A1 | 1/2012 | Koberstein et al. |
| 2012/0208724 A1 | 8/2012 | Steemers et al. |
| 2012/0258313 A1 | 10/2012 | Wen et al. |
| 2012/0270964 A1 | 10/2012 | Piletsky et al. |
| 2013/0143771 A1 | 6/2013 | Chilkoti |
| 2013/0157870 A1 | 6/2013 | Pushkarev et al. |
| 2013/0165350 A1 | 6/2013 | Kuimelis et al. |
| 2013/0171461 A1 | 7/2013 | Dach et al. |
| 2013/0172214 A1 | 7/2013 | Ye et al. |
| 2013/0211006 A1 | 8/2013 | Menchen et al. |
| 2013/0244249 A1 | 9/2013 | Jiang et al. |
| 2014/0186940 A1 | 7/2014 | Goel |
| 2014/0357523 A1 | 12/2014 | Zeiner et al. |
| 2015/0141269 A1 | 5/2015 | Soldatov et al. |
| 2016/0046985 A1 | 2/2016 | Drmanac et al. |
| 2016/0168632 A1 | 6/2016 | Edwards |
| 2016/0244548 A1 | 8/2016 | Boniface et al. |
| 2016/0298110 A1 | 10/2016 | McGall |
| 2016/0303534 A1 | 10/2016 | Zhou et al. |
| 2016/0369334 A1 | 12/2016 | Zhou et al. |
| 2017/0016063 A1 | 1/2017 | McGall et al. |
| 2017/0022554 A1 | 1/2017 | Drmanac et al. |

FOREIGN PATENT DOCUMENTS

| | | |
|---|---|---|
| EP | 1655069 A1 | 5/2006 |
| WO | WO-9844151 A1 | 10/1998 |
| WO | WO-0102452 A1 | 1/2001 |
| WO | WO-0227026 A2 | 4/2002 |
| WO | WO-03010203 A1 | 2/2003 |
| WO | WO-2004067759 A2 | 8/2004 |
| WO | WO-2004081183 A2 | 9/2004 |
| WO | WO-2007060456 A1 | 5/2007 |
| WO | WO-2007133831 A2 | 11/2007 |
| WO | WO-2008022332 A2 | 2/2008 |
| WO | WO-2010003132 A1 | 1/2010 |
| WO | WO-2010058342 A1 | 5/2010 |
| WO | WO-2010100265 A1 | 9/2010 |
| WO | WO-2012106546 A2 | 8/2012 |
| WO | WO-2012134602 A2 | 10/2012 |
| WO | WO-2012140224 A1 | 10/2012 |
| WO | WO-2013056090 A1 | 4/2013 |
| WO | WO-2013063382 A2 | 5/2013 |
| WO | WO-2012106546 A3 | 11/2013 |
| WO | WO-2013184754 A2 | 12/2013 |
| WO | WO-2015017759 A1 | 2/2015 |
| WO | WO-2015085268 A1 | 6/2015 |
| WO | WO-2015085274 A1 | 6/2015 |
| WO | WO-2015085275 A2 | 6/2015 |
| WO | WO-2015085275 A3 | 9/2015 |
| WO | WO-2016201111 A1 | 12/2016 |

OTHER PUBLICATIONS

Ayres, et al. Polymer brushes: Applications in biomaterials and nanotechnology. Polym. Chem. 2010; 1: 769-777.

Barbey, et al. Polymer brushes via surface-initiated controlled radical polymerization: synthesis, characterization, properties, and applications. Chem Rev. Nov. 2009;109(11):5437-5527. doi: 10.1021/cr900045a.

Beaucage, et al. Tetrahedron Letters. 1981; 22:1859-1862.

Bensimon, A. et al. Alignment and sensitive detection of DNA by a moving interface. Science 265, 2096-2098, (1994).

Bentley et al. Accurate whole human genome sequencing using reversible terminator chemistry. Nature 456(7218):53-59 (2008).

Bolli, et al. α-Bicyclo-DNA: Synthesis, Characterization, and Pairing Properties of α-DNA-Analogues with Restricted Conformational Flexibility in the Sugar—Phosphate Backbone. Carbohydrate Modifications in Antisense Research. ACS Symposium Series, vol. 580. Chapter 7, pp. 100-117.

Braunecker et al. Controlled/living radical polymerization: Features, developments, and perspectives. Progress in Polymer Science 32(1):93-146 (2007).

Brill, et al., Synthesis of Oligodeoxynucleoside phosphorodithioates via thioamidites. Journal American Chemical society. 111; 1989.

Brown, et al., Chemical synthesis and cloning of a tyrosine tRNA gene. Methods of enzymology. Academic press. 1979.

Carlsson, et al., Screening for genetic mutations. Scientific correspondence. Nature. 1996; 380:207.

U.S. Appl. No. 62/012,238, filed Jun. 13, 2014.
U.S. Appl. No. 62/173,140, filed Jun. 9, 2015.
U.S. Appl. No. 61/979,448, filed Apr. 14, 2014.

Cullen, et al. Polymeric brushes as functional templates for immobilizing ribonuclease A: study of binding kinetics and activity. Langmuir. Feb. 5, 2008;24(3):913-20. Epub Dec. 13, 2007.

Dempcy et al. Synthesis of a thymidyl pentamer of deoxyribonucleic guanidine and binding studies with DNA homopolynucleotides PNAS US 92:6097-6101 (1995).

Ding, et al., Single-molecule mechanical identification and sequencing. Nature Methods. Apr. 2012; 9(4): 367-372.

Eckstein, F., Oligonucleotides and Analogues: A Practical Approach, Oxford University Press. 1991.

Edmondson, et al. Polymer brushes via surface-initiated polymerizations. Chem Soc Rev. Jan. 10, 2004;33(1):14-22. Epub Dec. 2, 2003.

Egholm, et al., Peptide nucleic acids (PNA). Oligonucleotide analogs with an achiral. Journal American Chemical Society. 1992: 114 (5); pp. 1895-1897.

Egholm, et al., PNA hybridizes to complementary oligonucleotides obeying the Watson-Crick hydrogen-bonding rules. Nature. Oct. 7, 1993;365(6446):566-8.

(56) References Cited

OTHER PUBLICATIONS

European Search Report and search opinion dated Sep. 29, 2016 for International Application EP 16173782.0.
European search report with written opinion dated Jul. 17, 2017 for EP14868406.
Ferree, et al., Electrokinetic Stretching of Tethered DNA. Biophys J. Oct. 2003; 85(4): 2539-2546.
Fodor, S. P. et al. Light-directed, spatially addressable parallel chemical synthesis. Science 251, 767-773, (1991).
Galvin, et al. Applications of surface-grafted macromolecules derived from post-polymerization modification reactions. Progress in Polymer Science. 2012; 37.7: 871-906.
Gao, et al., In Situ synthesis of oligonucleotide microarrays. Biopolymers. 2004. 73; 579-596.
Gueroui, et al., Observation by fluorescence microscopy of transcription on single combed DNA. Proceedings of the National Academy of Sciences of the United States of America 99, 6005-6010, (2002).
Haber, et al., Magnetic tweezers for DNA micromanipulation. Review of scientific instruments. 2000. 71:4561.
Henry, et al. Three-dimensional arrangement of short DNA oligonucleotides at surfaces via the synthesis of DNA-branched polyacrylamide brushes by SI-ATRP. Macromol Rapid Commun. Sep. 15, 2011;32(18):1405-10. doi: 10.1002/marc.201100317. Epub Jul. 28, 2011.
Herdewijn, et al. Hexopyranosyl-Like Oligonucleotides. Carbohydrate Modifications in Antisense Research. ACS Symposium Series, vol. 580. Chapter 6, pp. 80-99.
Horn, et al., Oligonucleotides with Alternating Anionic and Cationic Phosphoramidate Linkages: Synthesis and Hybridization of Stereouniform Isomers. Tetrhedron letters. 1996. 37:6; 743-746.
International search report and written opinion dated Feb. 24, 2015 for PCT/US2014/068947.
International search report and written opinion dated Apr. 28, 2015 for PCT Application No. PCT/US14/68954.
International search report and written opinion dated Jun. 25, 2015 for PCT Application No. PCT/US14/68955.
International Search Report and Written Opinion dated Sep. 23, 2016 for International Application PCT/US2016/036709.
Jeffs, et al., Unusual conformation of a 3'-thioformacetal linkage in a DNA duplex*. Journal of Biomolecular NMR. 1994. 17-34.
Jenkins, et al., The Biosynthesis of Carbocyclic Nucleosides. Chemical society reviews. 1995; 169-176.
Kiedrowski, et al. Parabolic growth of a self-replicating hexadeoxynucleotide bearing a 3-5-phosphoamidate linkage. Agnew. Chem. 1991; 4:30.
Kim et al., Multiplexed single-molecule assay for enzymatic activity on flow-stretched DNA. Nat Methods. May 2007;4(5):397-9. Epub Apr. 15, 2007.
Kizhakkedathu, et al. Poly(oligo(ethylene glycol)acrylamide) Brushes by Surface Initiated Polymerization: Effect of Macromonomer Chain Length on Brush Growth and Protein Adsorption from Blood Plasma. Langmuir. 2009; 25: 3794-3801.
Koshkin, et al. LNA (Locked Nucleic Acid): An RNA Mimic Forming Exceedingly Stable LNA: LNA Duplexes. Journal American Chemical Society 1998: 120;13252-3.
Lee, et al. Immobilization of Amine-modified Oligonucleotides on Bifunctional Polymer Brushes Synthesized by Surface-initiated Polymerization. Bull. Korean Chem. Soc. 2012; 33(6): 2043-6.
Letsinger et al., Cationic oligonucleotides. J. Am. Chem. Soc.1988; 110(3):4470-4471.
Letsinger et al., Effects of pendant groups at phosphorus on binding properties of d-ApA analogues. Nucleic Acids Res. Apr. 25, 1986;14(8):3487-99.
Letsinger et al., Hybridization of Alternating Cationic/Anionic Oligonucleotide to RNA Segments. Nucleosides & Nucleotides. 13:1597 (1994).
Letsinger, et al., Nucleotide chemistry. XVI. Phosporamidate analogs of oligonucleotides. J. Org. Chem.,1970,35(11),pp. 3800-3803.

Maddry, et al. Synthesis of Nonionic Oligonucleotide Analogues. Carbohydrate Modifications in Antisense Research. ACS Symposium Series, vol. 580. Chapter 3, pp. 40-51.
Mag et al., Synthesis and selective cleavage of an oligodeoxynucleotide containing a bridged internucleotide 5'-phosphorothioate linkage. Nucleic Acids Res. 19:1437 (1991).
Mansfeld, et al. Clickable initiators, monomers and polymers in controlled radical polymerizations-a prospective combination in polymer science. Polymer Chemistry. 2010; 1.10: 1560-1598.
Marguiles, et al. Genome sequencing in microfabricated high-density picolitre reactors. Nature. Sep. 15, 2005;437(7057):376-80. Epub Jul. 31, 2005.
McGall, G. H. & Christians, F. C. High-density genechip oligonucleotide probe arrays. Adv Biochem Eng Biotechnol 77, 21-42, (2002).
Meier, et al., Peptide nucleic acids (PNas)-Unusual properties nonionic oligonucleotide analogues. Angew. Chemical. Int. Ed. Engl. 1992; 31:8.
Mesmaeker, et al. Comparison of rigid and flexible backbones in antisense oligonucleotides. Bioorganic and medical chemistry. 1994. 4;3;395-398.
Mesmaeker, et al. Novel Backbone Replacements for Oligonucleotides. Carbohydrate Modifications in Antisense Research. ACS Symposium Series, vol. 580. Chapter 2, pp. 24-39.
Michalet, X. et al. Dynamic molecular combing: stretching the whole human genome for high-resolution studies. Science 277, 1518-1523, (1997).
Mitra, et al. In situ localized amplification and contact replication of many individual DNA molecules. Nucleic Acids Res. Dec. 15, 1999;27(24):e34.
Narang, et al., Improved Phosphotriester Method for the Synthesis of Gene Fragments. Methods in enzymology. 1979. 68:90-98.
Nuwaysir, et al., Gene expression analysis using oligonucleotide arrays produced by maskless photolithography. Genome Res. 2002. 12, 1749-1755.
Office action dated Mar. 28, 2017 for CN Application No. 201480074638.8.
Olivier, et al. Surface-initiated controlled polymerization as a convenient method for designing functional polymer brushes: From self-assembled monolayers to patterned surfaces. Progress in polymer science. 2012; 37.1: 157-181.
Orski, et al. High Density Scaffolding of Functional Polymer Brushes: Surface Initiated Atom Transfer Radical Polymerization of Active Esters. Langmuir. 2010; 26(3): 2136-2143.
Pauwels et al., Biological activity of new 2-5A analogues. Chemica scripta. 1986. 26: 141-145.
Payne, et al., MolecularThreading:M echanicalExtraction,Stretching and Placem entofD N A M oleculesfrom a Liquid-Airinterface. PLoS ONE 8(7): e69058.
Premier Biosoft. Accelerating research in life sciences. 1994. Available at http://www.premierbiosoft.com/netprimer/index.html. Accessed on Oct. 18, 2016.
Proudnikov, et al. Immobilization of DNA in polyacrylamide gel for the manufacture of DNA and DNA-oligonucleotide microchips. Anal Biochem. May 15, 1998;259(1):34-41.
Prucker, et al. Polymer Layers through Self-Assembled Monolayers of Initiators. Langmuir. 1998; 14(24): 6893-6898.
Rawls, et al. Optimistic about antisense: promising clinical results and chemical strategies for further improvements delight antisense drug researchers. C&EN.1997. 35-39.
Rehman, et al. Immobilization of acrylamide-modified oligonucleotides by co-polymerization. Nucleic Acids Res. Jan. 15, 1999;27(2):649-55.
Reisner, et al. DNA confinement in nanochannels: physics and biological applications. Rep. Prog. Phys. 2012.75:10.
Rodriguez-Emmenegger, et al. Substrate-independent approach for the generation of functional protein resistant surfaces. Biomacromolecules. Apr. 11, 2011;12(4):1058-66. doi: 10.1021/bm101406m. Epub Mar. 25, 2011.
Ruhe, et al. Functional Polymer Brushes. Journal of Macromolecular Science, Part C: Polymer Reviews. 2002; 42.1: 91-138.

(56) References Cited

OTHER PUBLICATIONS

Seiffert, S. & Oppermann, W. Amine-Functionalized Polyacrylamide for Labeling and Crosslinking Purposes. Macromolecular Chemistry and Physics 208, 1744-1752, (2007).
Senaratne, et al. Self-assembled monolayers and polymer brushes in biotechnology: current applications and future perspectives. Biomacromolecules. 2005; 6.5: 2427-2448.
Shapero, et al. SNP genotyping by multiplexed solid-phase amplification and fluorescent minisequencing. Genome Res. Nov. 2001;11(11):1926-34.
Soni, et al., Progress toward ultrafast DNA sequencing using solid-state nanopores. Clin Chem. Nov. 2007; 53(11):1996-2001. Epub Sep. 21, 2007.
Sprinzl, et al., Enzymatic Incorporation of ATP and CTP Analogues into the 3' End of tRNA. Eur. J. Biochem. 81, 579-589 (1977).
Thomson, et al. Oligonucleotide and polymer functionalized nanoparticles for amplification-free detection of DNA. Biomacromolecules. Jun. 11, 2012;13(6):1981-9. doi: 10.1021/bm300717f. Epub May 30, 2012.
Timofeev, et al. Regioselective immobilization of short oligonucleotides to acrylic copolymer gels. Nucleic Acids Res. Aug. 15, 1996;24(16):3142-8.
United Kingdom combined search and examination report dated Jul. 3, 2017 for GB1613408.
Walker et al., Strand displacement amplification—an isothermal,in vitroDNA amplification technique. Nucl. Acids Res. (1992) 20 (7): 1691-1696. doi: 10.1093/nar/20.7.1691.
Wang et al., Stretching DNA with optical tweezers. Biophys J. Mar. 1997; 72(3): 1335-1346.
Westin et al., Anchored multiplex amplification on a microelectronic chip array. Nature Biotechnology 18,199-204(2000).
Yuan, et al. Polymer-functionalized silica nanosphere labels for ultrasensitive detection of tumor necrosis factor-alpha. Anal Chem. Sep. 1, 2011;83(17):6800-9. doi: 10.1021/ac201558w. Epub Aug. 15, 2011.
Zhang, et al., Assembly of Highly Aligned DNA Strands onto Si Chips. Langmuir,2005,21(9),pp. 4180-4184.
Zhang, et al., Preparation of megabase-sized DNA from a variety of organisms using the nuclei method for advanced genomics research. Nature Protocols 7, 467-478 (2012).
Mardis. Next-generation DNA sequencing methods. Annu Rev Genomics Hum Genet. 2008;9:387-402. doi: 10.1146/annurev.genom.9.081307.164359.
Compton. Nucleic acid sequence-based amplification. Nature. Mar. 7, 1991;350(6313):91-2.
EP14867116.7 Office Action dated Aug. 31, 2018.
EP14867494.8 Office Action dated Aug. 30, 2018.
CN201480074638.8 Office Action dated Jul. 12, 2018 (w/ English translation).
Gunderson, et al. A genome-wide scalable SNP genotyping assay using microarray technology. Nat Genet 37(5):549-554 (2005).
Office action dated Jul. 2, 2018 for U.S. Appl. No. 15/101,671.
Office action dated Jul. 17, 2018 for U.S. Appl. No. 15/101,168.
Office Action dated Nov. 3, 2017 for CN Patent Application No. 201480074638.8 (w/ English translation).
U.S. Appl. No. 15/178,411 Office Action dated Apr. 19, 2018.
Epicentre, DNA topoisomerase I, 2012. Vaccinia, Cat. Nos. VT710500, VT7101K and VT7105K.
European search report and search opinion dated Aug. 24, 2017 for EP Application No. 14867494.8.
European search report and search opinion dated Aug. 25, 2017 for EP Application No. EP14867116.7.
Office action dated Sep. 21, 2017 for U.S. Appl. No. 15/178,411.

\* cited by examiner

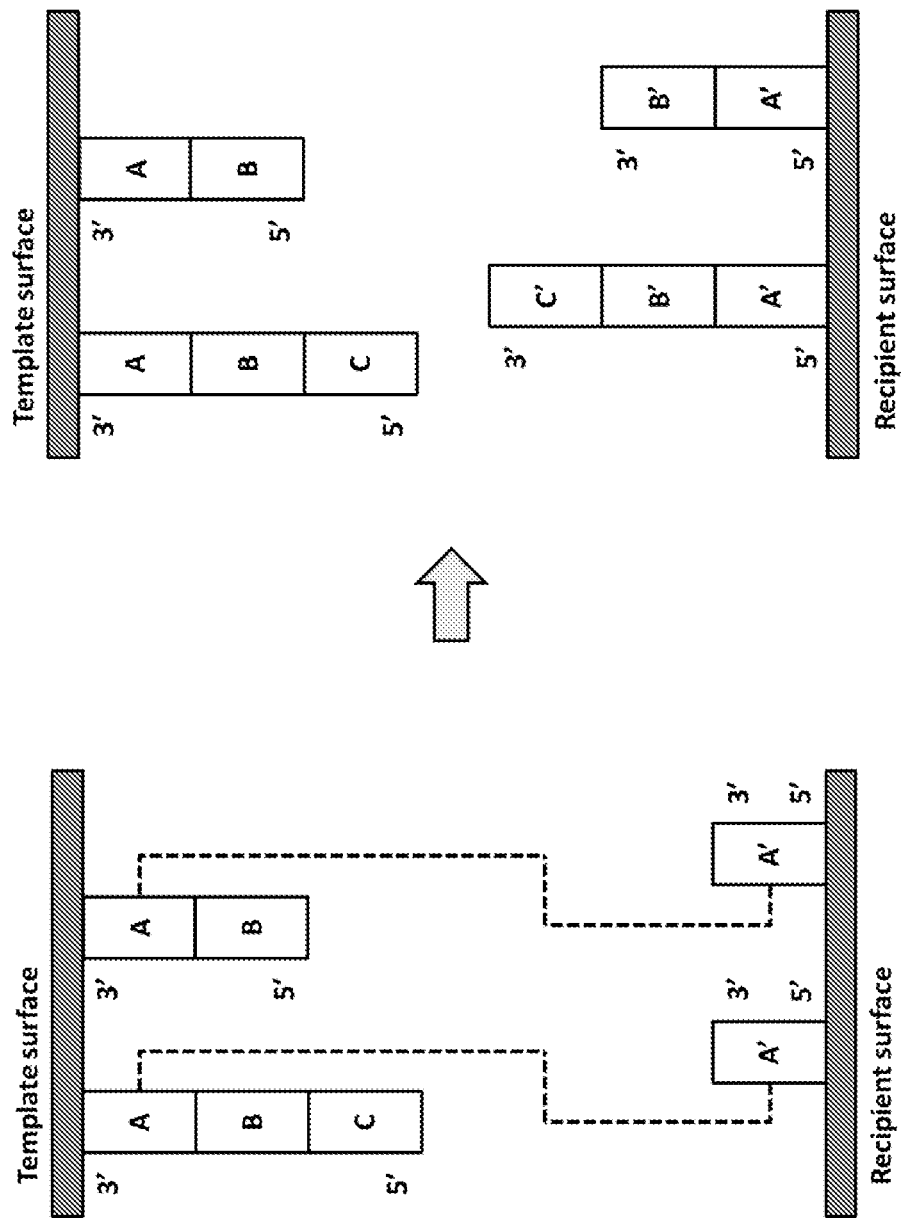

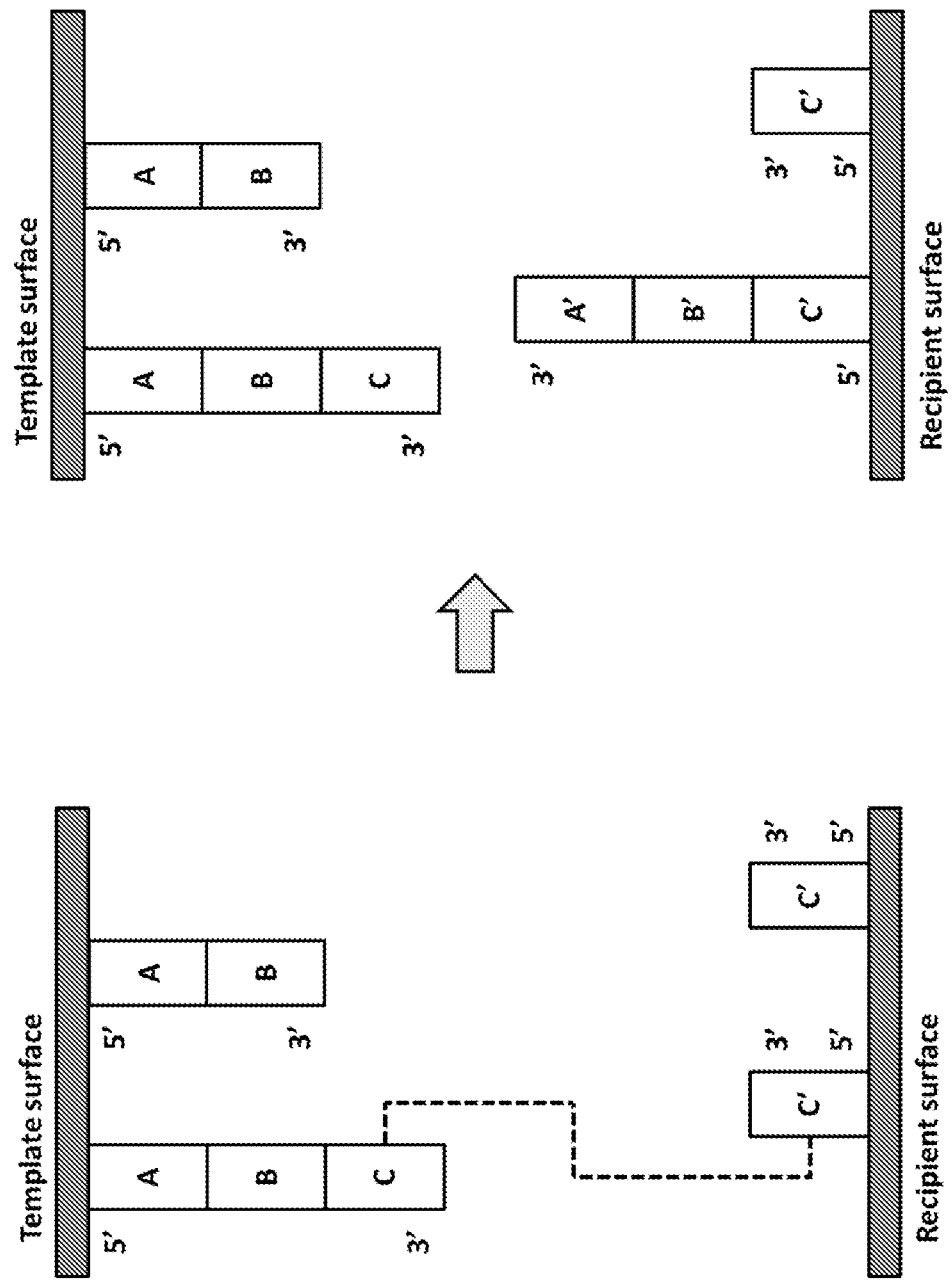

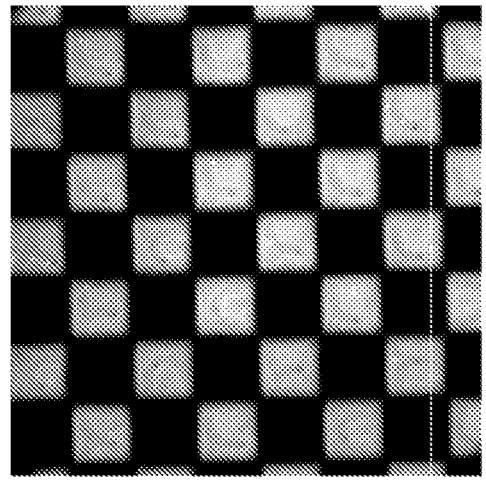
10x 0.5s 10 bin
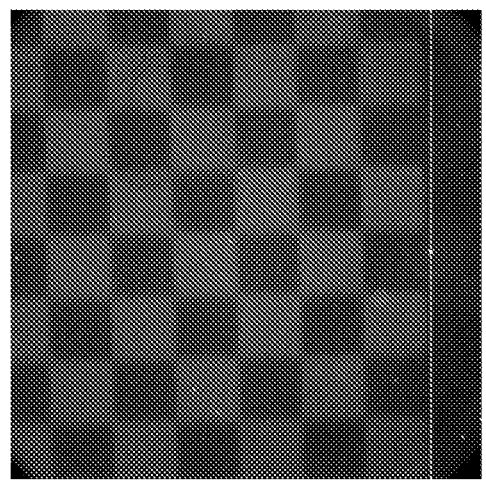
10x 2S 2 bin
FIG. 28

100 ms, 2bin
Cluster Number Ratio:
Approximately 1:50

METHODS FOR SEQUENCING NUCLEIC ACIDS

CROSS-REFERENCE

This application claims the benefit of U.S. Provisional Application No. 62/012,238 filed on Jun. 13, 2014, 61/979,448 filed on Apr. 14, 2014 61/912,027 filed on Dec. 5, 2013, 61/971,536 filed on Mar. 28, 2014, 61/973,864 filed on Apr. 2, 2014, 61/984,057 filed on Apr. 25, 2014, 62/008,985 filed on Jun. 6, 2014, 61/979,431, filed Apr. 14, 2014, 61/971,542, filed Mar. 28, 2014, and 62/033,125, filed Aug. 4, 2014, each of which is herein incorporated by reference in its entirety.

BACKGROUND

The Human Genome Project has resulted in a remarkable reduction in sequencing costs, from about $10 to less than $0.00001 per finished base. Exome sequencing can now be routinely used in both research and clinical settings for the detection of inherited or acquired mutations related to disease, and the FDA has listed over 100 drugs that have genotype information on their labels. In addition, the use of whole genome sequencing (WGS) has become widespread. However, current nucleic acid sequencing technology can be limited by sequencing length. As such, there can still be major limitations of the current technology which can severely limit the feasibility and utility of WGS for many studies. Namely, the read length of these "Next-Generation Sequencing" (NGS) technologies can be relatively short. The industry standard for sequencing may arguably be the Illumina HiSeq2500, which can sequence paired 150 base reads. With this relatively short read length, whole genome re-sequencing studies can generally be quite useful for identifying single nucleotide variants (SNVs); however, the relatively short read lengths can also be notoriously unreliable for identifying large insertions/deletions (indels) as well as structural variants.

In addition, it can often be difficult to phase the variants using short reads without considerable additional experimentation. Thus many clinical applications require or could benefit from long sequencing.

Currently, there are technologies that can generate long reads that have low accuracy, low throughput, and are costly. Therefore, they are not viable options for whole genome sequencing. Finally, other sequencing technologies do not provide detailed sequence information.

To address these issues, the methods, compositions, systems and kits described herein are provided to produce very long reads, i.e., mega base range, as well as accurately identify many, if not all, genetic variants (e.g., single nucleotide polymorphisms, insertions/deletions, polyploidy, transpositions, repeats and/or structural variants) and phase any identified variant to the appropriate homologous chromosome.

SUMMARY OF THE INVENTION

An aspect of the present disclosure provides a method for making a modified surface, comprising: (a) providing a surface; (b) covalently bonding initiator species to said surface; (c) conducting surface initiated polymerization of a polymer from said initiator species, thereby producing a polymer coating comprising a plurality of polymer chains; and (d) coupling markers to said polymer coating.

In some embodiments of aspects provided herein, said surface is selected from the group consisting of glass, silica, titanium oxide, aluminum oxide, indium tin oxide (ITO), silicon, polydimethylsiloxane (PDMS), polystyrene, polycyclicolefins, polymethylmethacrylate (PMMA), titanium, and gold. In some embodiments of aspects provided herein, said surface comprises glass. In some embodiments of aspects provided herein, said surface comprises silicon. In some embodiments of aspects provided herein, said surface is selected from the group consisting of flow cells, sequencing flow cells, flow channels, microfluidic channels, capillary tubes, piezoelectric surfaces, wells, microwells, microwell arrays, microarrays, chips, wafers, non-magnetic beads, magnetic beads, ferromagnetic beads, paramagnetic beads, superparamagnetic beads, and polymer gels. In some embodiments of aspects provided herein, said initiator species comprises an organosilane. In some embodiments of aspects provided herein, said initiator species comprises the molecule shown in FIG. 40. In some embodiments of aspects provided herein, said polymer species comprises polyacrylamide. In some embodiments of aspects provided herein, said polymer species comprises PMMA. In some embodiments of aspects provided herein, said polymer species comprises polystyrene. In some embodiments of aspects provided herein, said conducting surface initiated polymerization comprises atom-transfer radical polymerization (ATRP). In some embodiments of aspects provided herein, said conducting surface initiated polymerization comprises reversible addition fragmentation chain-transfer (RAFT). In some embodiments of aspects provided herein, said markers comprise oligonucleotides. In some embodiments of aspects provided herein, said markers comprise 5' acrydite modified oligonucleotides.

An aspect of the present disclosure provides a composition for transferring an array, comprising: (a) a substrate; (b) a coating coupled to said substrate; and (c) a plurality of first recipient oligonucleotides coupled to said coating, wherein each of said plurality of first recipient oligonucleotides comprises sequence complementary to a first adaptor sequence appended to each of a plurality of template oligonucleotides, wherein the plurality of template oligonucleotides is present on an array to be transferred.

In some embodiments of aspects provided herein, the method further comprises: (d) a plurality of second recipient oligonucleotides coupled to said coating, wherein each of said plurality of second recipient oligonucleotides comprises sequence complementary to a second adaptor sequence of template oligonucleotides to be transferred. In some embodiments of aspects provided herein, said first adaptor sequence is located at or near the 3' end of said template oligonucleotides to be transferred. In some embodiments of aspects provided herein, said first adaptor sequence is located at or near the 5' end of said template oligonucleotides to be transferred. In some embodiments of aspects provided herein, said second adaptor sequence is located at or near the 3' end of said template oligonucleotides to be transferred. In some embodiments of aspects provided herein, said second adaptor sequence is located at or near the 5' end of said template oligonucleotides to be transferred. In some embodiments of aspects provided herein, said coating comprises a polymer gel or coating. In some embodiments of aspects provided herein, said coating comprises an acrylamide or polyacrylamide gel or coating.

An aspect of the present disclosure provides a method for transferring an array, comprising: (a) providing a substrate and providing a plurality of first recipient oligonucleotides coupled to said substrate, each of said plurality of first recipient oligonucleotides comprising sequence complementary to a first adaptor sequence appended to a plurality of template oligonucleotides; (b) applying reaction mix comprising enzyme and dNTPs to the surface of said substrate; (c) contacting said substrate with an array comprising said template oligonucleotides; and (d) conducting extension reactions of said plurality of first recipient oligonucleotides using said plurality of template oligonucleotides as templates.

In some embodiments of aspects provided herein, said first adaptor sequence is located at or near the 3' end of said template oligonucleotides. In some embodiments of aspects provided herein, said first adaptor sequence is located at or near the 5' end of said template oligonucleotides. In some embodiments of aspects provided herein, said substrate comprises polymer. In some embodiments of aspects provided herein, said substrate comprises acrylamide or polyacrylamide.

An aspect of the present disclosure provides a method for generating an array comprising: providing a template array comprising at least 1,000 different oligonucleotides coupled thereto, coupling said template array to a recipient array having a plurality of oligonucleotides complementary to portions of the at least 1,000 different oligonucleotides, and performing an enzymatic reaction while the template array and the enzymatic array are coupled to one another, thereby generating a recipient array comprising recipient oligonucleotides, wherein at least 40% of the recipient oligonucleotides are complementary or identical to a full-length oligonucleotide from the at least 1,000 different oligonucleotides.

In some embodiments of aspects provided herein, the template array comprises at least 100 spots. In some embodiments of aspects provided herein, the template array comprises spots at most about 500 µm in size. In some embodiments of aspects provided herein, the directionality of the recipient oligonucleotides relative to the recipient array is the same as the directionality of the template oligonucleotides relative to the template array. In some embodiments of aspects provided herein, the directionality of the recipient oligonucleotides relative to the recipient array is the opposite of the directionality of the template oligonucleotides relative to the template array. In some embodiments of aspects provided herein, a plurality of recipient arrays are generated. In some embodiments of aspects provided herein, the plurality of recipient oligonucleotides are on average at least 99% identical between one recipient array and another. In some embodiments of aspects provided herein, the recipient oligonucleotides are at least 99% identical between one recipient array and another.

An aspect of the present disclosure provides a method for generating an array comprising: using a template array comprising template oligonucleotides to synthesize a recipient array comprising recipient oligonucleotides wherein the recipient array is coupled to the template array during the synthesis.

In some embodiments of aspects provided herein, at least 40% of the recipient oligonucleotides comprise full-length products. In some embodiments of aspects provided herein, at least 50% of the recipient oligonucleotides comprise full-length products. In some embodiments of aspects provided herein, at least 60% of the recipient oligonucleotides comprise full-length products. In some embodiments of aspects provided herein, the directionality of the recipient oligonucleotides relative to the recipient array is the same as the directionality of the template oligonucleotides relative to the template array. In some embodiments of aspects provided herein, the directionality of the recipient oligonucleotides relative to the recipient array is the opposite of the directionality of the template oligonucleotides relative to the template array. In some embodiments of aspects provided herein, a plurality of recipient arrays are generated. In some embodiments of aspects provided herein, the plurality of recipient oligonucleotides are on average at least 99% identical between one recipient array and another. In some embodiments of aspects provided herein, the recipient oligonucleotides are at least 99% identical between one recipient array and another.

An aspect of the present disclosure provides a method for sequencing a template nucleic acid molecule, comprising: (a) introducing one or more primer-binding sites into the template nucleic acid molecule to generate a primed template nucleic acid molecule; (b) contacting said primed template nucleic acid molecule with a substrate comprising primers immobilized thereon, each primer comprising: (i) a region complementary to a primer-binding site, and (ii) a barcode sequence indicative of a physical position of the primer on the substrate; (c) conducting extension reactions using said primers and template nucleic acid molecule as a template, thereby generating extension products, each extension product comprises (i) sequence of a fragment of the template nucleic acid or complement of the fragment, and (ii) sequence of the barcode sequence or a complement thereof; (d) sequencing said extension products to determine sequences of the fragments or complements thereof and barcode sequences or complements thereof; and (e) assembling the sequences of the fragments using the barcode sequence to thereby determine sequence of the template nucleic acid molecule.

In some embodiments of aspects provided herein, the method further comprises stretching the nucleic acid molecule prior to step (b). In some embodiments of aspects provided herein, said stretching is performed by molecular combing. In some embodiments of aspects provided herein, said stretching is performed by molecular threading. In some embodiments of aspects provided herein, said stretching is performed by transfer printing. In some embodiments of aspects provided herein, said stretching is performed in nanochannels. In some embodiments of aspects provided herein, said stretching is performed by magnetic tweezers. In some embodiments of aspects provided herein, said stretching is performed by optical tweezers. In some embodiments of aspects provided herein, said substrate comprises glass. In some embodiments of aspects provided herein, said substrate comprises hydrophobic glass. In some embodiments of aspects provided herein, said substrate comprises a polymer coating.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8B illustrates a schematic of enzymatic transfer resulting in a different orientation of the nucleic acids relative to the substrate.

FIG. 8C illustrates a schematic of enzymatic transfer resulting in the transfer of full-length strands.

FIG. 28 illustrates gel images with 10×2S 2 bin (left) and 10×0.5s 10 bin (right).

shows enzymatic cleavage of the double stranded target polynucleotide followed by end-repair in step d). Step e) shows appending of an adapter to the fragmented double stranded target polynucleotide followed by release of the double stranded target polynucleotide from the oligo array for sequencing in step f).

Figure 39:
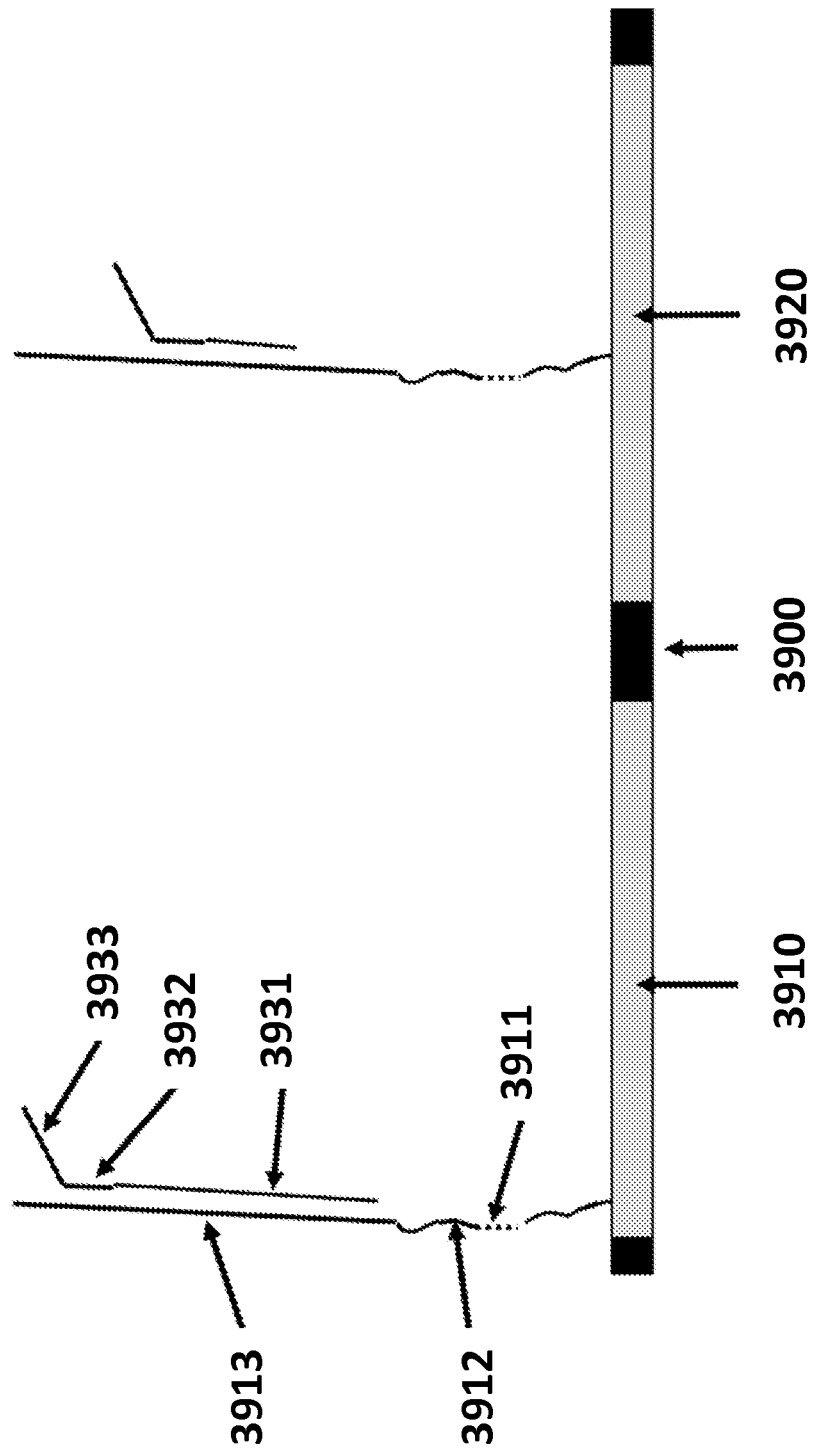

FIG. 39 illustrates a schematic of preparing an on-chip library with random primers.

Figure 40:
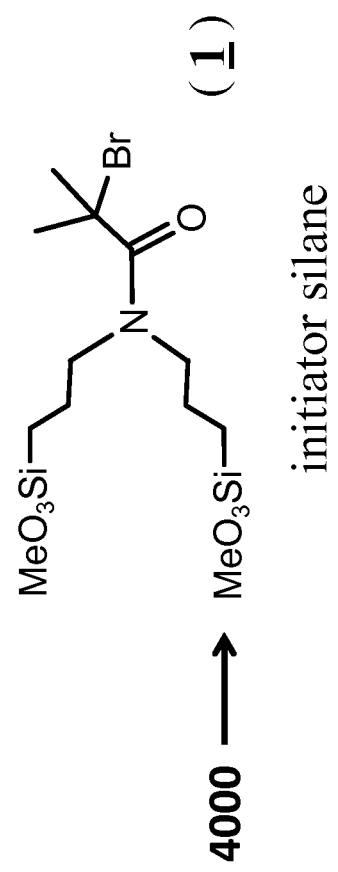

FIG. 40 illustrates an example of an initiator silane.

Figure 41:
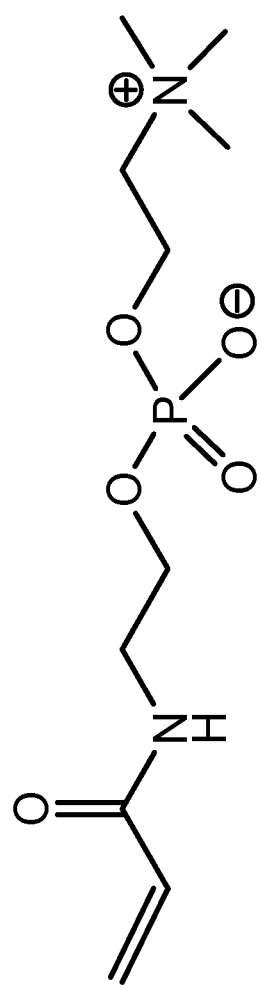

FIG. 41 illustrates an example of a phosphorylcholine-acrylamide monomer.

Figure 42:
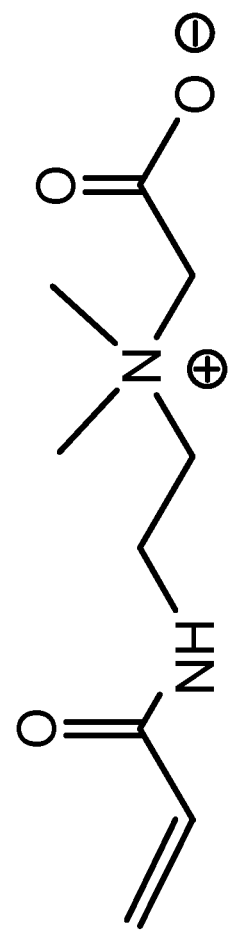

FIG. 42 illustrates an example of a betaine-acrylamide monomer.

Figure 43:
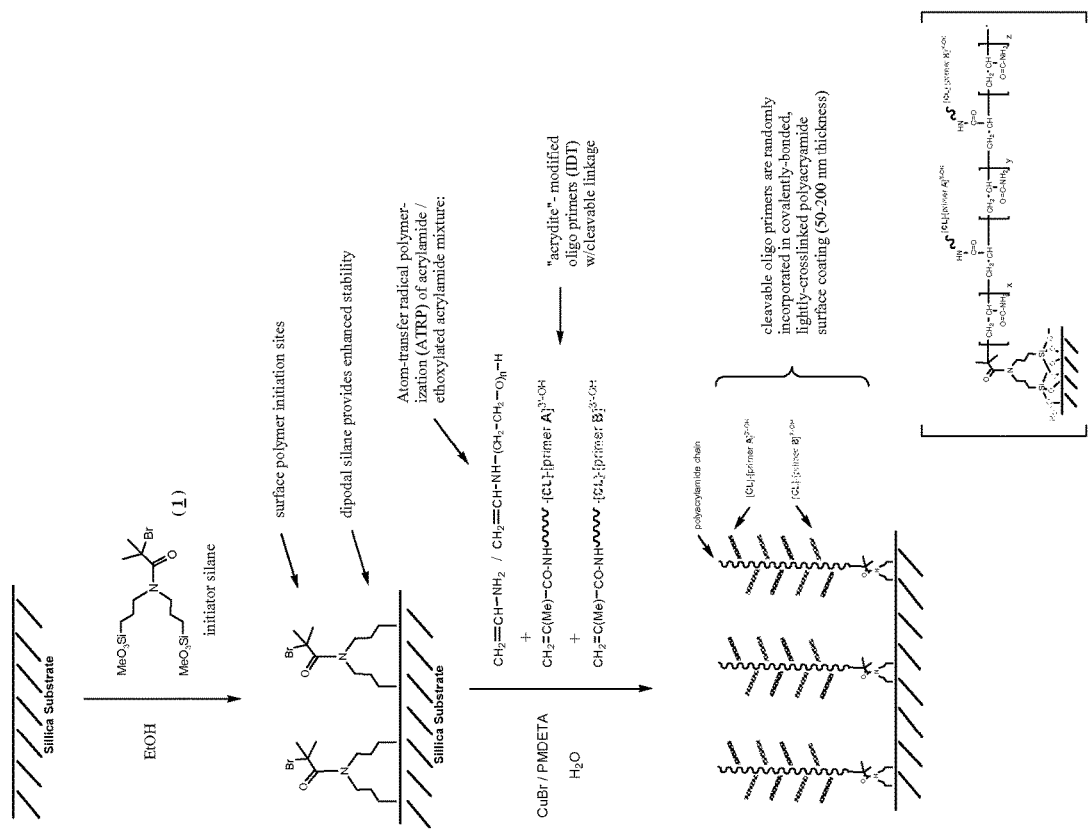

FIG. 43 illustrates an example of a process for producing a polyacrylamide surface coating with oligonucleotides.

DETAILED DESCRIPTION OF THE INVENTION

Overview

Provided herein are methods, compositions, and kits for fabricating DNA chips, controlling orientation of oligonucleotides on arrays, stretching nucleic acids, preparing sequencing libraries, and sequencing nucleic acids that can be hundreds of kilobases to megabases in length. Methods of the invention integrate several technologies to address limitations of current next generation sequencing (NGS). While NGS has progressed far enough that exome or whole genome sequencing is available to researchers at any institution, interpreting the results can be extremely challenging. Phased haplotype information for sequence variants and mutations is critical information that is missing from current whole genome sequencing strategies, and could significantly aid the analysis and interpretation of genome sequence data.

This disclosure provides methods and compositions for improved polymer coatings on surfaces that can be used for arrays. The polymer coatings can be generated via surface-initiated polymerization (SIP) via initiator species bound to a surface. The polymer coatings can incorporate modified monomers to modulate physicochemical properties of the coatings. The polymer coatings can incorporate oligonucleotides.

Provided herein are methods for generating arrays comprising oligonucleotides ("oligos"), where each oligo comprises a barcode that marks a position or address on the array (i.e., positional barcodes). In some cases, provided herein are oligo array ("chip") fabrication methods that are optimized to (a) reduce feature ("spot") size and pitch, (b) optionally, reverse the orientation of the oligos on the arrays to make the 3' end of each oligo on the array free for extension (e.g., enzymatic addition of nucleotide bases), and (c) increase the length and accuracy of the oligo synthesis. Projection lithography and photo-acid generating polymer films can be used to synthesize oligo arrays at high feature ("spot") density ($>10^8/cm^2$). At a feature size of 1 μm, barcoded oligos on the arrays can localize sequence reads obtained through the methods provided herein to about a 2000 bp region of genomic DNA. The oligos in each spot of the array can comprise the same barcode sequence and oligos in different array spots can comprise different barcode sequences.

To generate copies of an array with a desired orientation (e.g., 5' end attached to array substrate) a face-to-face gel transfer process may be employed. The face-to-face gel transfer process can significantly reduce the unit cost of fabrication while simultaneously flipping the oligo orientation such that the 5' end is immobilized, which can have assay advantages as described herein. Moreover, the selective transfer of full length oligos and subsequent amplification of the full length oligo can allow the oligo arrays to contain very long oligos (50+ bases) without suffering from low yield or partial length products as described herein. The transfer can comprise generation of nucleic acid sequences complementary to the template oligo sequences. The transfer process can occur by enzymatic replication or by non-enzymatic physical transfer of array components between the surfaces. Transfer can comprise fabrication of complementary sequences which are already attached to a recipient/transfer array. For example, primers bound to a recipient/transfer array are complementary to adaptors on the template array and can be extended using the template array sequences as templates to thereby generate a full length or partial length transfer array. Transfer can comprise fabrication of complementary sequences from a template array followed by attachment of the complementary sequences to a transfer array.

Transfer can preserve the orientation of a nucleic acid relative to its coupled array surface (e.g., the 3' end of the template nucleic acid is bound to the template array and the 3' end of the transferred nucleic acid complement is bound to the transfer array). Transfer can reverse the orientation of a nucleic acid relative to its coupled array surface (e.g., the 3' end of the template nucleic acid is bound to the template array and the 5' end of the transferred nucleic acid complement is bound to the transfer array).

In some cases, the array transfer methods described herein are useful in generating transfer or recipient arrays having an increased or enriched amount or percentage of oligonucleotides coupled to the transfer or recipient array surface that are 100% of the length (i.e., a same or identical length) of the respective oligonucleotides on the array used as a template (i.e., template array) for the transfer procedure. The transfer procedure can be a face-to-face enzymatic transfer as provided herein. The face-to-face enzymatic transfer method can also be referred to as enzymatic transfer by synthesis or ETS. Array transfer can result in a transfer or recipient array comprising at least, at most, more than, less than, or about 30%, 40%, 50%, 55%, 60%, 65%, 70%, 75%, 80%, 85%, 90%, 95%, 96%, 97%, 98%, 99%, or 99.9% transferred oligonucleotides that are the same or identical or 100% of the length of the respective oligonucleotide on a template array used to generate the transfer or recipient array. A transferred oligonucleotide that is 100% of the length (i.e., the same or identical length) of a template oligonucleotide can be referred to as full-length product (e.g., full-length product oligo). A template array fabricated by methods known in that art (e.g. spotting or in situ synthesis) can comprise about 20% oligonucleotides that are a desired length (i.e., full-length oligonucleotides) and about 80% oligonucleotides that are not a desired length (i.e., partial-length oligonucleotides). Transfer of the array generated by methods known in the art comprising about 20% full-length oligonucleotides and about 80% partial-length oligonucleotides using array transfer methods as provided herein (e.g., ETS) can result in the generation of transfer or recipient arrays comprising at most about 20% full-length product oligos. A transfer array comprising primers complementary to a sequence at the unbound end of the full-length oligonucleotide on the template array can be used to conduct transfer; Many or all of the partial-length products on the template array comprising about 20% full-length oligonucleotides and about 80% partial-length oligonucleotides lack the unbound end portion of sequence used in array transfer (e.g., ETS) as provided herein and so cannot be transferred. In some cases, an array fabricated according to the methods herein has a greater percentage of oligonucleotides of a desired length (i.e., full length oligos) such that transfer of an array fabricated according to the methods herein using array transfer methods provided herein (i.e., ETS) results in the generation of transfer or recipient arrays with a higher percentage of full-length product oligos as compared to fabrication and transfer methods known in the art. A full-length oligo on an array (e.g., template array) fabricated using the methods provided herein can be about, at most, or at least 10, 15, 20, 25, 30, 35, 40, 45, 50, 55, 60, 65, 70, 75, 80, 85, 90, 95, or 100 bases long. A full length product oligo on a transfer or recipient array transferred using array transfer methods provided herein (i.e., ETS) can be about, at most, or at least 10, 15, 20, 25, 30, 35, 40, 45, 50, 55, 60, 65, 70, 75, 80, 85, 90, 95, or 100 bases long.

Array transfer as provided herein can be performed multiple times. In some cases, a template array (e.g., oligo array) is subjected to an array transfer process a plurality of times. A template array can be subjected to an array transfer process at least, at most, more than, less than or about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000 times. The array transfer process can be a face-to-face enzymatic transfer method as provided herein. A plurality of transfer or recipient arrays can be generated from multiple array transfers using the same template array. Each transfer or recipient array generated from a single template array using an array transfer method as provided herein can be at least, at most, more than, less than, or about 30%, 40%, 50%, 55%, 60%, 65%, 70%, 75%, 80%, 85%, 90%, 95%, 96%, 97%, 98%, 99%, or 99.9% identical to the template array and/or each other transfer or recipient array generated from the template array. Array transfer can be performed multiple times in a series of transfers, using the transfer array from one array transfer as the template array for a subsequent transfer. For example, a first transfer can be performed from a template array with oligos bound to the array at their 3' ends to a first transfer array with complementary oligos bound to the array at their 5' ends, and a second transfer can be performed from the first transfer array (now serving as a template array) to a second transfer array. In some cases, each progressive transfer or recipient array in a series of array transfer reactions as provided herein generate recipient or transfer arrays with an enriched percentage of full-length product oligos (i.e., a transferred oligonucleotide that is 100% of the length of a template oligonucleotide) and sequences matching the original template array.

In some cases, array transfer can be aided by the use of adaptor sequences on the oligos on the template oligo array. Oligos can comprise a desired final sequence with the addition of one or more adaptor sequences. The one or more adaptor sequences can be on the 5' or 3' end of the oligos on the template array. In some cases, the one or more adaptor sequences are on the 3'end of the oligos on the template array. In some cases, the one or more adaptor sequences are on the 5'end of the oligos on the template array. Primers on a recipient/transfer array can be complementary to adaptor sequences, allowing hybridization between the primers and the oligos (via hybridization to all or a portion of the adaptor sequences) on the template array. Such hybridization can aid in the transfer from one array to another. Some or all adaptor sequences can be removed from transfer array oligos after transfer, for example by enzymatic cleavage, digestion, or restriction.

In some cases, array transfer can be aided by the flexibility or deformability of the array or of a surface coating on the array. For example, an array comprising a polyacrylamide gel coating with coupled oligonucleotides can be used in array transfer. The deformability of the gel coating can allow for array components to contact each other despite surface roughness. The deformability can permit enzymes required in enzymatic array transfer methods (e.g., ETS as provided herein) more effective contact with reaction components as compared to arrays that do not comprise a polyacrylamide gel The more effective contact can permit a higher number of enzymatic transfers as compared to arrays that do not comprise a polyacrylamide gel. The more effective contact can permit the generation of a higher percentage of transfer or recipient arrays comprising oligos that are 100% of the length of the oligos on a template array used in the array transfer method.

Array components can be amplified or regenerated by enzymatic reactions. For example, bridge amplification can be conducted on array component oligonucleotides via hybridization between adaptor sequences on the array components and surface-bound oligonucleotide primers, followed by enzymatic extension or amplification. Amplification can be used to recover lost array component density or to increase density of array components beyond their original density.

Figure 1:
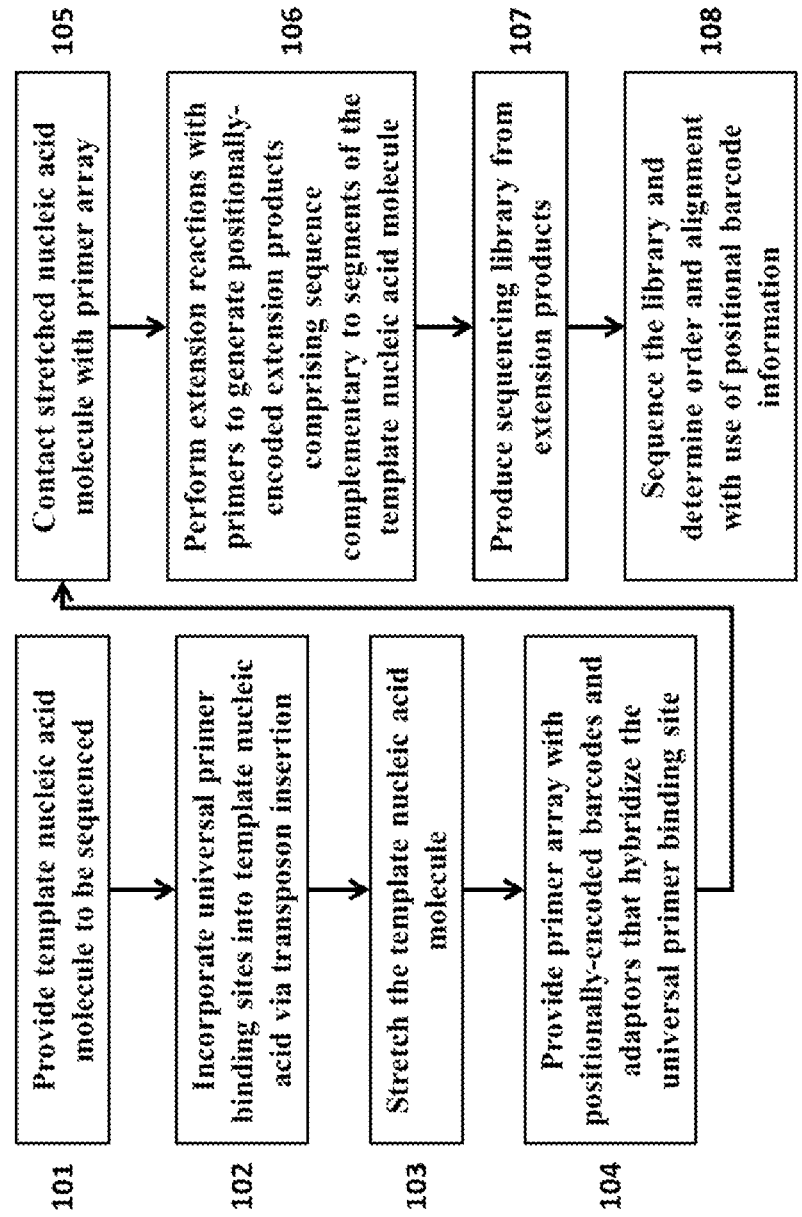
FIG. 1 illustrates a flow chart of a process for sequencing a nucleic acid molecule.
Figure 2:
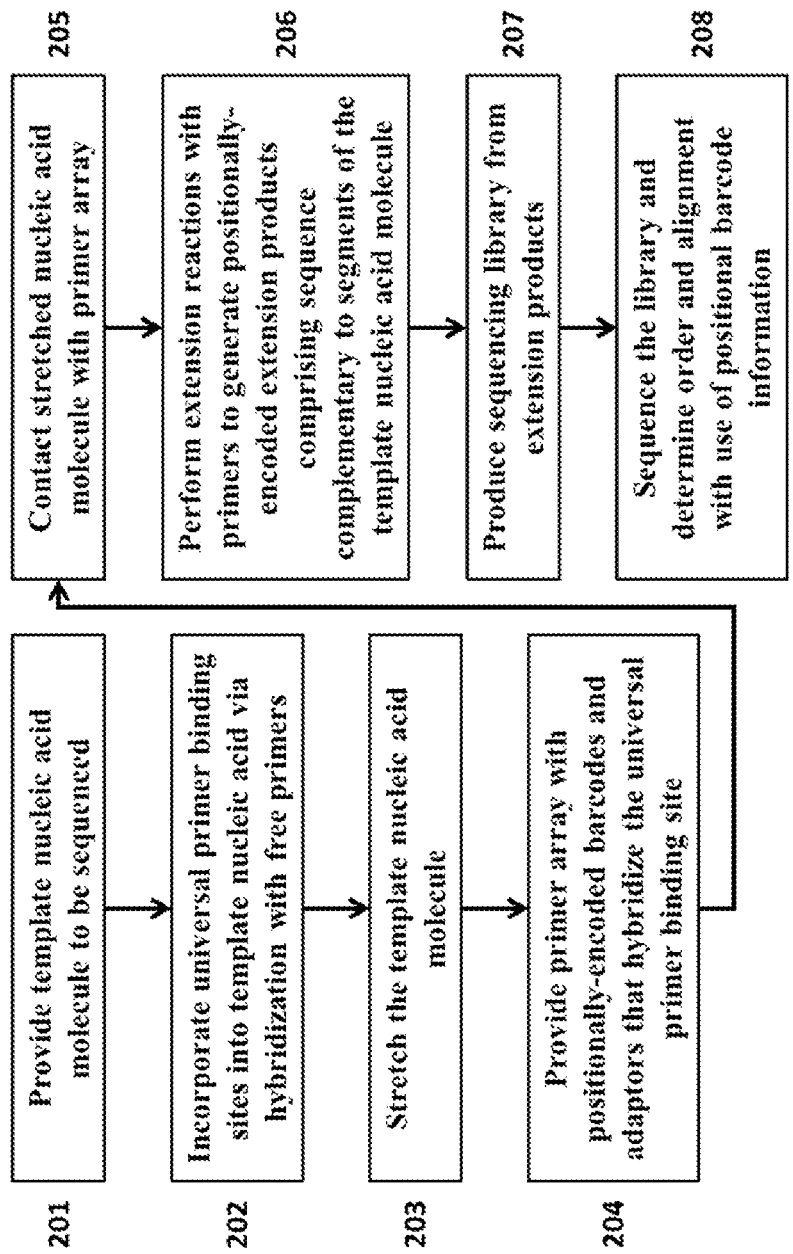
FIG. 2 illustrates a flow chart of a process for sequencing a nucleic acid molecule.

Template nucleic acid molecules can be prepared for stretching across a barcoded oligo array produced by a method as provided herein. A template nucleic acid molecule can be processed to incorporate sequences complementary to those present in oligos on a barcoded oligo array. Example processes are shown in FIG. 1 and FIG. 2. A template nucleic acid molecule to be sequenced can be provided 101, 201. Universal primer binding sites can be incorporated into the template nucleic acid molecule, by transposon insertion 102 or by hybridization with free primers 202. The template nucleic acid molecule can be stretched 103, 203. The nucleic acid stretching can be performed using a method as provided herein. A primer/oligo array with positionally-encoded barcodes and adaptors that hybridize the primer binding sites can be provided 104, 204. The stretched template nucleic acid molecule can be contacted with the primer/oligo array 105, 205. Extension reactions can be performed with the primers, generating positionally-encoded extension products that comprise sequence complementary to segments of the template nucleic acid molecule 106, 206, and barcodes such that the barcodes associated with a given template nucleic acid segment correspond to the array spot which it contacted.

Figure 3:
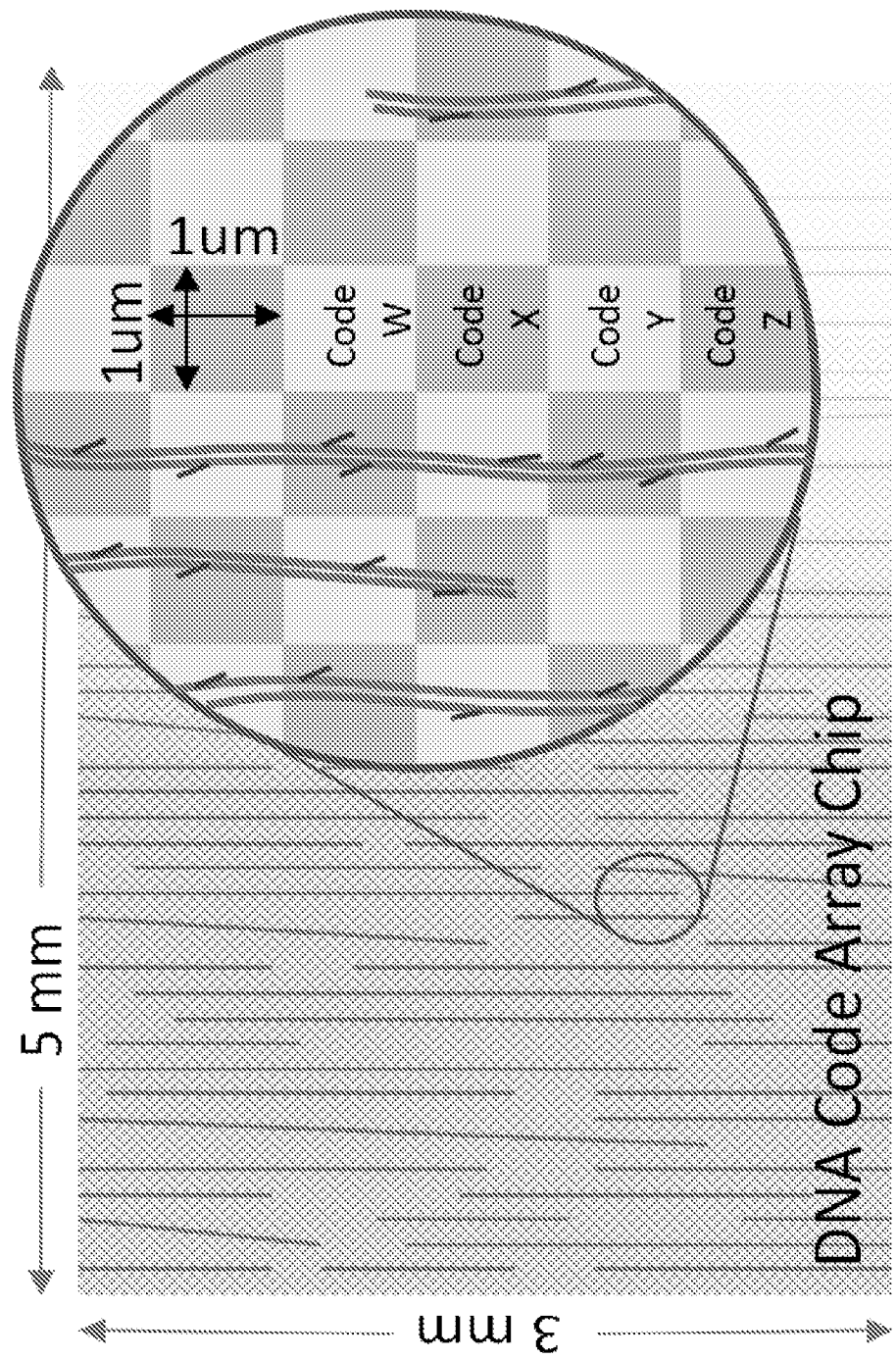
FIG. 3 illustrates a high-feature array prepared using the face-to-face enzymatic transfer methods described herein. The checkerboard DNA array was enzymatically transferred by Bst onto a 10 μm thin acrylamide gel coated second surface.

Stretched nucleic acid molecules can be used to generate sequencing libraries which can then be sequenced with the aid of positional barcodes as shown in FIGS. 1 and 2. In some cases, a plurality of template nucleic acid molecules (e.g., DNA) are stretched on a barcoded oligo array surface (for example, 30-40× diploid genome coverage) generated using the methods provided herein. Oligos on the array surface can prime the stretched nucleic acid molecules (e.g., DNA), which can then serve as templates for the generation of Next Generation Sequencing (NGS) libraries (as shown in FIG. 3). The NGS libraries can then be sequenced using any NGS platform as described herein or any other suitable sequence read out technology (e.g., Illumina HiSeq). Since the oligos used to generate the sequencing library are barcoded, positional information for assembling the short NGS reads is obtained. Using barcodes, the short reads can be linked into long strings corresponding to the stretched DNA molecules from which they were derived. The long strings can allow for de novo assembly, nucleotide variant detection, structure variant detection, and resolution of haplotypes from diploid samples. The long strings can be more than or about 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, or 10,000 bases.

The methods provided herein are especially useful for determining the sequence of long nucleic acid molecules, for example nucleic acid molecules with more than 100,000 bases. These processes are also useful for sequencing nucleic acid molecules or regions thereof with insertions, deletions, transpositions, repeat regions, telomeres, SNPs, cancer cell genomes, viral cell genomes, and methicillin resistance regions (mec regions). The positional information conveyed by the barcode sequences can be useful for assembling or aligning nucleic acid molecule reads from at least 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, or 10,000 template nucleic acid fragments or extension products.

Nucleic Acids and Sources Thereof

A "nucleic acid molecule" or "nucleic acid" as referred to herein can be deoxyribonucleic acid (DNA) or ribonucleic acid (RNA) including known analogs or a combination thereof unless otherwise indicated. Nucleic acid molecules to be sequenced herein can be obtained from any source of nucleic acid. The nucleic acid molecule can be single-stranded or double-stranded. In some cases, the nucleic acid molecule is DNA. The DNA can be obtained and purified using standard techniques in the art and include DNA in purified or unpurified form. The DNA can be mitochondrial DNA, cell-free DNA, complementary DNA (cDNA), or genomic DNA. In some cases, the nucleic acid molecule is genomic DNA (gDNA). The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can derived from one or more of chromosome 1, 2, 3, 4, 5, 6, 7, 8, 9, 10, 11, 12, 13, 14, 15, 16, 17, 18, 19, 20, 21, 22, X, or Y. The RNA can be obtained and purified using standard techniques in the art and include RNAs in purified or unpurified form, which include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs, siRNAs, piRNAs and long nc RNAs.

The source of nucleic acid for use in the methods and compositions described herein can be a sample comprising the nucleic acid. The nucleic acid can be isolated from the sample and purified by any of the methods known in the art for purifying the nucleic acid from the sample. The sample can be derived from a non-cellular entity comprising polynucleotides (e.g., a virus) or from a cell-based organism (e.g., member of archaea, bacteria, or eukarya domains). In some cases, the sample is obtained from a swab of a surface, such as a door or bench top.

The sample can be from a subject, e.g., a plant, fungi, eubacteria, archeabacteria, protest, or animal. The subject can be an organism, either a single-celled or multi-cellular organism. The subject can be cultured cells, which can be primary cells or cells from an established cell line, among others. The sample can be isolated initially from a multicellular organism in any suitable form. The animal can be a fish, e.g., a zebrafish. The animal can be a mammal. The mammal can be, e.g., a dog, cat, horse, cow, mouse, rat, or pig. The mammal can be a primate, e.g., a human, chimpanzee, orangutan, or gorilla. The human can be a male or female. The sample can be from a human embryo or human fetus. The human can be an infant, child, teenager, adult, or elderly person. The female can be pregnant, suspected of being pregnant, or planning to become pregnant. In some cases, the sample is a single or individual cell from a subject and the polynucleotides are derived from the single or individual cell. In some cases, the sample is an individual micro-organism, or a population of micro-organisms, or a mixture of micro-organisms and host cellular or cell free nucleic acids.

The sample can be from a subject (e.g., human subject) who is healthy. In some cases, the sample is taken from a subject (e.g., an expectant mother) at at least 4, 5, 6, 7, 8, 9, 10, 11, 12, 13, 14, 15, 16, 17, 18, 19, 20, 21, 22, 23, 24, 25, or 26 weeks of gestation. In some cases, the subject is affected by a genetic disease, a carrier for a genetic disease or at risk for developing or passing down a genetic disease, where a genetic disease is any disease that can be linked to a genetic variation such as mutations, insertions, additions, deletions, translocation, point mutation, trinucleotide repeat disorders and/or single nucleotide polymorphisms (SNPs).

The sample can be from a subject who has a specific disease, disorder, or condition, or is suspected of having (or at risk of having) a specific disease, disorder or condition. For example, the sample can be from a cancer patient, a patient suspected of having cancer, or a patient at risk of having cancer. The cancer can be, e.g., acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chromic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom Macroglobulinemia, or Wilms Tumor. The sample can be from the cancer and/or normal tissue from the cancer patient.

The sample can be aqueous humour, vitreous humour, bile, whole blood, blood serum, blood plasma, breast milk, cerebrospinal fluid, cerumen, enolymph, perilymph, gastric juice, mucus, peritoneal fluid, saliva, sebum, semen, sweat, tears, vaginal secretion, vomit, feces, or urine. The sample can be obtained from a hospital, laboratory, clinical or medical laboratory. The sample can be taken from a subject.

The sample can be an environmental sample comprising medium such as water, soil, air, and the like. The sample can be a forensic sample (e.g., hair, blood, semen, saliva, etc.). The sample can comprise an agent used in a bioterrorist attack (e.g., influenza, anthrax, smallpox).

The sample can comprise nucleic acid. The sample can comprise cell-free nucleic acid. The sample can be a cell line, genomic DNA, cell-free plasma, formalin fixed paraffin embedded (FFPE) sample, or flash frozen sample. A formalin fixed paraffin embedded sample can be deparaffinized before nucleic acid is extracted. The sample can be from an organ, e.g., heart, skin, liver, lung, breast, stomach, pancreas, bladder, colon, gall bladder, brain, etc. Nucleic acids can be extracted from a sample by means available to one of ordinary skill in the art.

The sample can be processed to render it competent for fragmentation, ligation, denaturation, amplification, stretching, and/or sequencing or any of the methods provided herein. Exemplary sample processing can include lysing cells of the sample to release nucleic acid, purifying the sample (e.g., to isolate nucleic acid from other sample components, which can inhibit enzymatic reactions), diluting/concentrating the sample, and/or combining the sample with reagents for further nucleic acid processing. In some examples, the sample can be combined with a restriction enzyme, reverse transcriptase, or any other enzyme of nucleic acid processing.

The methods described herein can be used for sequencing one or more target nucleic acids or polynucleotides. The term polynucleotide, or grammatical equivalents, can refer to at least two nucleotides covalently linked together. A polynucleotide described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469, 863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-O atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some cases. The nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

A "nucleic acid molecule" or "nucleic acid" as referred to herein can be an "oligonucleotide" "aptamer" or a "polynucleotide". The term "oligonucleotide" can refer to a nucleotide chain, typically less than 200 residues long, e.g., between 15 and 100 nucleotides long. The oligonucleotide can comprise at least or about 1, 2, 3, 4, 5, 6, 7, 8, 9, 10, 15, 20, 25, 30, 35, 40, 45, or 50 bases. The oligonucleotides can be from about 3 to about 5 bases, from about 1 to about 50 bases, from about 8 to about 12 bases, from about 15 to about 25 bases, from about 25 to about 35 bases, from about 35 to about 45 bases, or from about 45 to about 55 bases. The oligonucleotide (also referred to as "oligo") can be any type of oligo (e.g., primer). In some cases, the oligos are 5'-acrydite-modified oligos. The oligos can be coupled to the polymer coatings as provided herein on surfaces as provided herein. The oligonucleotides can comprise cleavable linkages. Cleavable linkages can be enzymatically cleavable. Oligonucleotides can be single- or double-stranded. The terms "primer" and "oligonucleotide primer" can refer to an oligonucleotide capable of hybridizing to a complementary nucleotide sequence. The term "oligonucleotide" can be used interchangeably with the terms "primer," "adapter," and "probe." The term "polynucleotide" can refer to a nucleotide chain typically greater than 200 residues long. Polynucleotides can be single- or double-stranded.

The term "hybridization"/"hybridizing" and "annealing" can be used interchangeably and can refer to the pairing of complementary nucleic acids.

The term "primer" can refer to an oligonucleotide, generally with a free 3' hydroxyl group, that is capable of hybridizing with a template nucleic acid or nucleic acid molecule (such as a target polynucleotide, target DNA, target RNA or a primer extension product) and is also capable of promoting polymerization of a polynucleotide complementary to the template. A primer can contain a non-hybridizing sequence that constitutes a tail of the primer. A primer can still be hybridizing to a target even though its sequences may not be fully complementary to the target.

Primers can be oligonucleotides that can be employed in an extension reaction by a polymerase along a polynucleotide template, such as in PCR or cDNA synthesis, for example. The oligonucleotide primer can be a synthetic polynucleotide that is single stranded, containing a sequence at its 3'-end that is capable of hybridizing with a sequence of the target polynucleotide. Normally, the 3' region of the primer that hybridizes with the target nucleic acid has at least 80%, 90%, 95%, or 100%, complementarity to a sequence or primer binding site.

Primers can be designed according to known parameters for avoiding secondary structures and self-hybridization. Different primer pairs can anneal and melt at about the same temperatures, for example, within about 1, 2, 3, 4, 5, 6, 7, 8, 9 or 10° C. of another primer pair. In some cases, greater than about 1, 2, 3, 4, 5, 6, 7, 8, 9, 10, 15, 20, 25, 30, 35, 40, 45, 50, 100, 200, 500, 1000, 5000, 10,000 or more primers are initially used. Such primers may be able to hybridize to the genetic targets described herein. In some cases, about 2 to about 10,000, about 2 to about 5,000, about 2 to about 2,500, about 2 to about 1,000, about 2 to about 500, about 2 to about 100, about 2 to about 50, about 2 to about 20, about 2 to about 10, or about 2 to about 6 primers are used.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Integrated DNA Technologies, Operon Technologies, Amersham Pharmacia Biotech, Sigma, and Life Technologies. The primers can have an identical melting temperature. The melting temperature of a primer can be about, more than, less than, or at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, or 85° C. In some cases, the melting temperature of the primer is about 30 to about 85° C., about 30 to about 80° C., about 30 to about 75° C., about 30 to about 70° C., about 30 to about 65° C., about 30 to about 60° C., about 30 to about 55° C., about 30 to about 50° C., about 40 to about 85° C., about 40 to about 80° C., about 40 to about 75° C., about 40 to about 70° C., about 40 to about 65° C., about 40 to about 60° C., about 40 to about 55° C., about 40 to about 50° C., about 50 to about 85° C., about 50 to about 80° C., about 50 to about 75° C., about 50 to about 70° C., about 50 to about 65° C., about 50 to about 60° C., about 50 to about 55° C., about 52 to about 60° C., about 52 to about 58° C., about 52 to about 56° C., or about 52 to about 54° C.

The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The $T_M$ (melting or annealing temperature) of each primer can be calculated using software programs such as Net Primer (free web based program at http://www.premierbiosoft.com/netprimer/index.html). The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest; thus the $T_M$ can be recalculated based on both the sequences of the 5' half and the 3' half of each primer.

The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest, thus the TM can be recalculated based on both the sequences of the 5' half and the 3' half of each primer.

"Complementary" can refer to complementarity to all or only to a portion of a sequence (e.g., template nucleic acid). The number of nucleotides in the hybridizable sequence of a specific oligonucleotide primer should be such that stringency conditions used to hybridize the oligonucleotide primer will prevent excessive random non-specific hybridization. Usually, the number of nucleotides in the hybridizing portion of the oligonucleotide primer will be at least as great as the defined sequence on the target polynucleotide (e.g., template nucleic acid) that the oligonucleotide primer hybridizes to, namely, at least 5, at least 6, at least 7, at least 8, at least 9, at least 10, at least 11, at least 12, at least 13, at least 14, at least 15, at least about 20, and generally from about 6 to about 10 or 6 to about 12 of 12 to about 200 nucleotides, usually about 10 to about 50 nucleotides. A target polynucleotide can be larger than an oligonucleotide primer or primers as described previously.

The term "about" as used herein refers to +/−10%, 9%, 8%, 7%, 6%, 5%, 4%, 3%, 2%, or 1% of the designated amount.

The term "longer DNA", "long DNA", "longer nucleic acid", or "long nucleic acid" as used herein can include nucleic acids, (e.g., DNA) that are more than, at least, or about, 100, 200, 300, 400, 500, 600, 700, 800, 900 kb or more than, at least, or about, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 Mb. Upper limits of long nucleic acids can include, e.g., 100, 90, 80, 70, 60, 50, 40, 30, 20, 10, 9, 8, 7, 6, 5, or 4.5 Mb. Long nucleic acids can be in the range of 100 kb to 4.6 Mb. Long nucleic acids can be in the range of 100 kb to 10 Mb. In some cases, long nucleic acids can be in the range of 100 kb to 20 Mb. Long nucleic acids can be in the range of 100 kb to 30 Mb. Long nucleic acids can be in the range of 100 kb to 40 Mb. Long nucleic acids can be in the range of 100 kb to 50 Mb. In some instances, a large nucleic acid consists of an entire genome of an organism (e.g., *E. coli*). It should be understood that the methods, compositions, systems and kits provided herein are not limited to DNA but can include other nucleic acid molecules as described herein and can be sequenced using the same methods as described below.

In some cases, a set of barcodes is provided. The term "barcode" can refer to a known nucleic acid sequence that allows some feature of a nucleic acid (e.g., oligo) with which the barcode is associated to be identified. In some cases, the feature of the nucleic acid to be identified is the spatial position of each nucleic acid (e.g., oligo) on an array or chip. The barcodes can be designed for precision sequence performance, e.g., GC content between 40% and 60%, no homo-polymer runs longer than two, no self-complementary stretches longer than 3, and be comprised of sequences not present in a human genome reference. A barcode sequence can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. A barcode sequence can be at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. A barcode sequence can be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. An oligonucleotide (e.g., primer or adapter) can comprise about, more than, less than, or at least 1, 2, 3, 4, 5, 6, 7, 8, 9, or 10 different barcodes. Barcodes can be of sufficient length and comprise sequences that can be sufficiently different to allow the identification of the spatial position of each nucleic acid (e.g., oligo) based on barcode (s) with which each nucleic acid is associated. In some cases, each barcode is, for example, four deletions or insertions or substitutions away from any other barcode in an array. The oligos in each array spot on the barcoded oligo array can comprise the same barcode sequence and oligos in different array spots can comprise different barcode sequences. The barcode sequence used in one array spot can be different from the barcode sequence in any other array spot. Alternatively, the barcode sequence used in one array spot can be the same as the barcode sequence used in another array spot, as long as the two array spots are not adjacent. Barcode sequences corresponding to particular array spots can be known from the controlled synthesis of the array. Alternatively, barcode sequences corresponding to particular array spots can be known by retrieving and sequencing material from particular array spots. A candidate set of barcodes containing 1.5 million 18 base barcodes was designed as an example.

Enzymes

RNA-dependent DNA polymerases for use in the methods and compositions provided herein can be capable of effecting extension of a primer according to the methods provided herein. Accordingly, an RNA-dependent DNA polymerase can be one that is capable of extending a nucleic acid primer along a nucleic acid template that is comprised at least predominantly of ribonucleotides. Suitable RNA-dependent DNA polymerases for use in the methods, compositions, and kits provided herein include reverse transcriptases (RTs). RTs are well known in the art. Examples of RTs include, but are not limited to, Moloney murine leukemia virus (M-MLV) reverse transcriptase, human immunodeficiency virus (HIV) reverse transcriptase, rous sarcoma virus (RSV) reverse transcriptase, avian myeloblastosis virus (AMV) reverse transcriptase, rous associated virus (RAV) reverse transcriptase, and myeloblastosis associated virus (MAV) reverse transcriptase or other avian sarcoma-leukosis virus (ASLV) reverse transcriptases, and modified RTs derived therefrom. See e.g. U.S. Pat. No. 7,056,716. Many reverse transcriptases, such as those from avian myeoloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a RT which lacks or has substantially reduced RNase H activity. RTs devoid of RNase H activity are known in the art, including those comprising a mutation of the wild type reverse transcriptase where the mutation eliminates the RNase H activity. Examples of RTs having reduced RNase H activity are described in US20100203597. In these cases, the addition of an RNase H from other sources, such as that isolated from *E. coli*, can be employed for the degradation of the starting RNA sample and the formation of the double stranded cDNA. Combinations of RTs can also contemplated, including combinations of different non-mutant RTs, combinations of different mutant RTs, and combinations of one or more non-mutant RT with one or more mutant RT.

DNA-dependent DNA polymerases for use in the methods and compositions provided herein can be capable of effecting extension of a primer according to the methods provided herein. Accordingly, a DNA-dependent DNA polymerase can be one that is capable of extending a nucleic acid primer along a first strand cDNA in the presence of the RNA template or after selective removal of the RNA template. Exemplary DNA dependent DNA polymerases suitable for the methods provided herein include but are not limited to Klenow polymerase, with or without 3'-exonuclease, Bst DNA polymerase, Bca polymerase, .phi.29 DNA polymerase, Vent polymerase, Deep Vent polymerase, Taq polymerase, T4 polymerase, and *E. coli* DNA polymerase 1, derivatives thereof, or mixture of polymerases. In some cases, the polymerase does not comprise a 5'-exonuclease activity. In other cases, the polymerase comprises 5' exonuclease activity. In some cases, the primer extension can be performed using a polymerase comprising strong strand displacement activity such as for example Bst polymerase. In other cases, the primer extension can be performed using a polymerase comprising weak or no strand displacement activity. One skilled in the art can recognize the advantages and disadvantages of the use of strand displacement activity during the primer extension step, and which polymerases can be expected to provide strand displacement activity (see e.g., New England Biolabs Polymerases). For example, strand displacement activity can be useful in ensuring whole transcriptome coverage during the random priming and extension step. Strand displacement activity can further be useful in the generation of double stranded amplification products during the priming and extension step. Alternatively, a polymerase which comprises weak or no strand displacement activity can be useful in the generation of single stranded nucleic acid products during primer hybridization and extension that can be hybridized to the template nucleic acid.

In some cases, any double stranded product generated by the methods described herein can be end repaired to produce blunt ends for the adapter ligation applications described herein. Generation of the blunt ends on the double stranded products can be generated by the use of a single strand specific DNA exonuclease such as for example exonuclease 1, exonuclease 7 or a combination thereof to degrade overhanging single stranded ends of the double stranded products. Alternatively, any double stranded products generated by methods provided herein can be blunt ended by the use of a single stranded specific DNA endonuclease for example but not limited to mung bean endonuclease or 51 endonuclease. Alternatively, any double stranded products generated by methods provided herein can be blunt ended by the use of a polymerase that comprises single stranded exonuclease activity such as for example T4 DNA polymerase, any other polymerase comprising single stranded exonuclease activity or a combination thereof to degrade the overhanging single stranded ends of the double stranded products. In some cases, the polymerase comprising single stranded exonuclease activity can be incubated in a reaction mixture that does or does not comprise one or more dNTPs. In other cases, a combination of single stranded nucleic acid specific exonucleases and one or more polymerases can be used to blunt end the double stranded products of the primer extension reaction. In still other cases, the products of the extension reaction can be made blunt ended by filling in the overhanging single stranded ends of the double stranded products. For example, the fragments can be incubated with a polymerase such as T4 DNA polymerase or Klenow polymerase or a combination thereof in the presence of one or more dNTPs to fill in the single stranded portions of the double stranded products. Alternatively, any double stranded products generated by methods provided herein can be made blunt by a combination of a single stranded overhang degradation reaction using exonucleases and/or polymerases, and a fill-in reaction using one or more polymerases in the presence of one or more dNTPs.

In another embodiment, the adapter ligation applications described herein can leave a gap between a non-ligation strand of the adapters and a strand of the double stranded product. In these instances, a gap repair or fill-in reaction can be used to append the double stranded product with the sequence complementary to the ligation strand of the adapter. Gap repair can be performed with any number of DNA dependent DNA polymerase described herein. In some cases, gap repair can be performed with a DNA dependent DNA polymerase with strand displacement activity. In some cases, gap repair can be performed using a DNA dependent DNA polymerase with weak or no strand displacement activity. In some cases, the ligation strand of the adapter can serve as the template for the gap repair or fill-in reaction. In some cases, gap repair can be performed using Taq DNA polymerase.

Various ligation processes and reagents are known in the art and can be useful for carrying out the methods provided herein. For example, blunt ligation can be employed. Similarly, a single dA nucleotide can be added to the 3'-end of the double-stranded DNA product, by a polymerase lacking 3'-exonuclease activity and can anneal to an adapter comprising a dT overhang (or the reverse). This design allows the hybridized components to be subsequently ligated (e.g., by T4 DNA ligase). Other ligation strategies and the corresponding reagents and known in the art and kits and reagents for carrying out efficient ligation reactions are commercially available (e.g, from New England Biolabs, Roche).

The terms "joining," "appending" and "ligation" as used herein, with respect to two polynucleotides, such as a stem-loop adaptor/primer oligonucleotide and a target polynucleotide, refers to the covalent attachment of two separate polynucleotides to produce a single larger polynucleotide with a contiguous backbone. Methods for joining two polynucleotides are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adaptor oligonucleotide is joined to a target polynucleotide by a ligase, for example a DNA ligase or RNA ligase. Multiple ligases, each having characterized reaction conditions, are known in the art, and include, without limitation $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Ligation can be between polynucleotides having hybridizable sequences, such as complementary overhangs. Ligation can also be between two blunt ends. Generally, a 5' phosphate is utilized in a ligation reaction. The 5' phosphate can be provided by the target polynucleotide, the adaptor oligonucleotide, or both. 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases.

Methods of Amplification

The methods, compositions and kits described herein can be useful to generate amplification-ready products for downstream applications such as massively parallel sequencing (i.e. next generation sequencing methods) or hybridization platforms. Methods of amplification are well known in the art. Examples of PCR techniques that can be used include, but are not limited to, quantitative PCR, quantitative fluorescent PCR (QF-PCR), multiplex fluorescent PCR (MF-PCR), real time PCR(RT-PCR), single cell PCR, restriction fragment length polymorphism PCR (PCR-RFLP), PCR-RFLP/RT-PCR-RFLP, hot start PCR, nested PCR, in situ polony PCR, in situ rolling circle amplification (RCA), bridge PCR, picotiter PCR, digital PCR, droplet digital PCR, and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA), single primer isothermal amplification (SPIA, see e.g. U.S. Pat. No. 6,251,639), Ribo-SPIA, or a combination thereof. Other amplification methods that can be used herein include those described in U.S. Pat. Nos. 5,242,794; 5,494,810; 4,988,617; and 6,582, 938. Amplification of target nucleic acids can occur on a bead. In other embodiments, amplification does not occur on a bead. Amplification can be by isothermal amplification, e.g., isothermal linear amplification. A hot start PCR can be performed wherein the reaction is heated to 95° C. for two minutes prior to addition of the polymerase or the polymerase can be kept inactive until the first heating step in cycle 1. Hot start PCR can be used to minimize nonspecific amplification. Other strategies for and aspects of amplification are described in U.S. Patent Application Publication No. 2010/0173394 A1, published Jul. 8, 2010, which is incorporated herein by reference. In some cases, the amplification methods can be performed under limiting conditions such that only a few rounds of amplification (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.), such as for example as is commonly done for cDNA generation. The number of rounds of amplification can be about 1-30, 1-20, 1-15, 1-10, 5-30, 10-30, 15-30, 20-30, 10-30, 15-30, 20-30, or 25-30.

Techniques for amplification of target and reference sequences are known in the art and include the methods described in U.S. Pat. No. 7,048,481. Briefly, the techniques can include methods and compositions that separate samples into small droplets, in some instances with each containing on average less than about 5, 4, 3, 2, or one target nucleic acid molecule (polynucleotide) per droplet, amplifying the nucleic acid sequence in each droplet and detecting the presence of a target nucleic acid sequence. In some cases, the sequence that is amplified is present on a probe to the genomic DNA, rather than the genomic DNA itself. In some cases, at least 200, 175, 150, 125, 100, 90, 80, 70, 60, 50, 40, 30, 20, 10, or 0 droplets have zero copies of a target nucleic acid.

PCR can involve in vitro amplification based on repeated cycles of denaturation, oligonucleotide primer annealing, and primer extension by thermophilic template dependent polynucleotide polymerase, which can result in the exponential increase in copies of the desired sequence of the polynucleotide analyte flanked by the primers. In some cases, two different PCR primers, which anneal to opposite strands of the DNA, can be positioned so that the polymerase catalyzed extension product of one primer can serve as a template strand for the other, leading to the accumulation of a discrete double stranded fragment whose length is defined by the distance between the 5' ends of the oligonucleotide primers.

LCR uses a ligase enzyme to join pairs of preformed nucleic acid probes. The probes can hybridize with each complementary strand of the nucleic acid analyte, if present, and ligase can be employed to bind each pair of probes together resulting in two templates that can serve in the next cycle to reiterate the particular nucleic acid sequence.

SDA (Westin et al 2000, Nature Biotechnology, 18, 199-202; Walker et al 1992, Nucleic Acids Research, 20, 7, 1691-1696), can involve isothermal amplification based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

In some cases, the amplification is exponential, e.g. in the enzymatic amplification of specific double stranded sequences of DNA by a polymerase chain reaction (PCR).

Preparation of Surfaces for Generation of Oligonucleotide Arrays

The methods and compositions provided in this disclosure can comprise preparing a surface for generating an array. In some cases, the array is an array of oligonucleotides (oligonucleotide array or oligo array). The preparation of the surface can comprise creating a polymer coating on the surface. The surface can comprise glass, silica, titanium oxide, aluminum oxide, indium tin oxide (ITO), silicon, polydimethylsiloxane (PDMS), polystyrene, polycyclicolefins, polymethylmethacrylate (PMMA), cyclic olefin copolymer (COC), other plastics, titanium, gold, other metals, or other suitable materials. The surface can be flat or round, continuous or non-continuous, smooth or rough. Examples of surfaces include flow cells, sequencing flow cells, flow channels, microfluidic channels, capillary tubes, piezoelectric surfaces, wells, microwells, microwell arrays, microarrays, chips, wafers, non-magnetic beads, magnetic beads, ferromagnetic beads, paramagnetic beads, superparamagnetic beads, and polymer gels.

Initiator Species Attachment

In some cases, preparation of surfaces as described herein for the generation of oligonucleotide arrays as provided herein comprises bonding initiator species to the surface. In some cases, the initiator species comprises at least one organosilane. In some cases, the initiator species comprises one or more surface bonding groups. In some cases, the initiator species comprises at least one organosilane and the at least one organosilane comprises one or more surface bonding groups. The organosilane can comprise one surface-bonding group, resulting in a mono-pedal structure. The organosilane can comprise two surface-bonding groups, resulting in a bi-pedal structure. The organosilane can comprise three surface-bonding groups, resulting in a tri-pedal structure. The surface bonding group can comprise $MeO_3Si$, $(MeO)_3Si$, $(EtO)_3Si$, $(AcO)_3Si$, $(Me_2N)_3Si$, and/or $(HO)_3Si$. In some cases, the surface bonding group comprises $MeO_3Si$ (e.g. see 4000 in FIG. 40). In some cases, the surface bonding group comprises $(MeO)_3Si$. In some cases, the surface bonding group comprises $(EtO)_3Si$. In some cases, the surface bonding group comprises $(AcO)_3Si$. In some cases, the surface bonding group comprises $(Me_2N)_3Si$. In some cases, the surface bonding group comprises $(HO)_3Si$. In some cases, the organosilane comprises multiple surface bonding groups. The multiple surface bonding groups can be the same or can be different. The organosilane can comprise the silane reagent shown in FIG. 40. In some cases, the initiator species comprises at least one organophosphonic acid, wherein the surface bonding group comprises $(HO)_2P(=O)$. The organophosphonic acid can comprise one surface-bonding group, resulting in a mono-pedal structure. The organophosphonic acid can comprise two surface-bonding groups, resulting in a bi-pedal structure. The organophosphonic acid can comprise three surface-bonding groups, resulting in a tri-pedal structure.

Surface-Initiated Polymerization (SIP)

In some cases, a surface as provided herein comprises a surface-bound initiator species as provided herein for the generation of oligo arrays comprises a surface coating or functionalization. The surface coating or functionalization can be hydrophobic or hydrophilic. The surface coating can comprise a polymer coating or polymer brush, such as polyacrylamide or modified polyacrylamide. The surface coating can comprise a gel, such as a polyacrylamide gel or modified polyacrylamide gel. The surface coating can comprise metal, such as patterned electrodes or circuitry. The surface coating or functionalization can comprise a binding agent, such as streptavidin, avidin, antibodies, antibody fragments, or aptamers. The surface coating or functionalization can comprise multiple elements, for example a polymer or gel coating and a binding agent. In some cases, preparation of surfaces as described herein for the generation of oligonucleotide arrays as provided herein comprises forming a polymer coating on the surface-bound initiator species. The surface bound initiator species can be any surface bound initiator species known in the art. In some cases, the surface bound initiator species comprises an organosilane as provided herein. The organosilane can comprise one or more surface bonding groups as described herein. In some cases, the organosilane comprises at least two surface bonding groups. The presence of two or more surface bonding groups can serve to increase the stability of an initiator species-polymer coating complex. The one or more surface bonding groups can be any surface bonding group as provided herein. The resulting polymer coatings can comprise linear chains. The resulting polymer coatings can comprise chains that are branched. The branched chains can be lightly branched. A lightly branched chain can comprise less than or about 1, 2, 3, 4, 5, 6, 7, 8, 9, or 10 branches. The polymer coatings can form polymer brush thin-films. The polymer coatings can include some cross-linking. The polymer coatings can form a graft structure. The polymer coatings can form a network structure. The polymer coatings can form a branched structure. The polymers can comprise homogenous polymers. The polymers can comprise block copolymers. The polymers can comprise gradient copolymers. The polymers can comprise periodic copolymers. The polymers can comprise statistical copolymers.

In some cases, the polymer coating formed on the surface bound initiator species comprises polyacrylamide (PA). The polymer can comprise polymethylmethacrylate (PMMA). The polymer can comprise polystyrene (PS). The polymer can comprise polyethylene glycol (PEG). The polymer can comprise polyacrylonitrile (PAN). The polymer can comprise poly(styrene-r-acrylonitrile) (PSAN). The polymer can comprise a single type of polymer. The polymer can comprise multiple types of polymer. The polymer can comprise polymers as described in Ayres, N. (2010). Polymer brushes: Applications in biomaterials and nanotechnology *Polymer Chemistry*, 1(6), 769-777, or polymers as described in Barbey, R., Lavanant, L., Paripovic, D., Schüwer, N., Sugnaux, C., Tugulu, S., & Klok, H. A. (2009) Polymer brushes via surface-initiated controlled radical polymerization: synthesis, characterization, properties, and applications. *Chemical reviews*, 109(11), 5437-5527, the disclosure of each of which is herein incorporated by reference in its entirety.

Polymerization of the polymer coating on the surface bound initiator species can comprise methods to control polymer chain length, coating uniformity, or other properties. The polymerization can comprise controlled radical polymerization (CRP), atom-transfer radical polymerization (ATRP), or reversible addition fragmentation chain-transfer (RAFT). The polymerization can comprise living polymerization processes as described in Ayres, N. (2010). Polymer brushes: Applications in biomaterials and nanotechnology *Polymer Chemistry*, 1(6), 769-777, or as described in Barbey, R., Lavanant, L., Paripovic, D., Schüwer, N., Sugnaux, C., Tugulu, S., & Klok, H. A. (2009) Polymer brushes via surface-initiated controlled radical polymerization: synthesis, characterization, properties, and applications. *Chemical reviews*, 109(11), 5437-5527, the disclosure of each of which is herein incorporated by reference in its entirety.

The polymer coating formed on a surface bound initiator species as provided herein can be of uniform thickness over the entire area of the polymer coating. The polymer coating formed on a surface bound initiator species as provided herein can be of varying thickness across the area of the polymer coating. The polymer coating can be at least 1 µm, 2 µm, 3 µm, 4 µm, 5 µm, 7 µm, 8 µm, 9 µm, 10 µm, 15 µm, 20 µm, 25 µm, 30 µm, 40 µm thick. The polymer coating may be at least 50 µm thick. The polymer coating may be at least 75 µm thick. The polymer coating may be at least 100 µm thick. The polymer coating may be at least 150 µm thick. The polymer coating may be at least 200 µm thick. The polymer coating may be at least 300 µm thick. The polymer coating may be at least 400 µm thick. The polymer coating may be at least 500 µm thick. The polymer coating may be between about 1 µm and about 10 µm thick. The polymer coating may be between about 5 µm and about 15 µm thick. The polymer coating may be between about 10 µm and about 20 µm thick. The polymer coating may be between about 30 µm and about 50 µm thick. The polymer coating may be between about 10 µm and about 50 µm thick. The polymer coating may be between about 10 µm and about 100 µm thick. The polymer coating may be between about 50 µm and about 100 µm thick. The polymer coating may be between about 50 µm and about 200 µm thick. The polymer coating may be between about 100 µm and about 30 µm thick. The polymer coating may be between about 100 µm and about 500 µm thick.

Modification of Physicochemical Characteristics of Polymer Coating

In some cases, physiochemical properties of the polymer coatings herein are modified. The modification can be achieved by incorporating modified acrylamide monomers during the polymerization process. In some cases, ethoxylated acrylamide monomers are incorporated during the polymerization process. The ethoxylated acrylamide monomers can comprise monomers of the form $CH_2=CH-CO-NH(-CH_2-CH2-O-)_nH$. The ethoxylated acrylamide monomers can comprise hydroxyethyl acrylamide monomers. The ethoxylated acrylamide monomers can comprise ethylene glycol acrylamide monomers. The ethoxylated acrylamide monomers can comprise hydroxyethylmethacrylate (HEMA). The incorporation of ethoxylated acrylamide monomers can result in a more hydrophobic polyacrylamide surface coating. In some cases, phosphorylcholine acrylamide monomers are incorporated during the polymerization process. The phosphorylcholine acrylamide monomers can comprise monomers of the structure shown in FIG. 41. The phosphorylcholine acrylamide monomers can comprise other phosphorylcholine acrylamide monomers. In some cases, betaine acrylamide monomers are incorporated during the polymerization process. The betaine acrylamide monomers can comprise monomers of the structure shown in FIG. 42. The betaine acrylamide monomers can comprise other betaine acrylamide monomers.

Generation of Oligonucleotide Arrays on Prepared Surfaces

In some cases, a surface as provided herein treated using a method as provided herein to comprise a polymer coating as provided herein is used to generate an oligonucleotide array. In some cases, the oligonucleotide or oligo arrays are generated on surfaces comprising polymer coatings as provided herein formed on surface bound initiator species as provided herein. The oligo arrays can be high density oligonucleotide arrays. The oligo array can comprise at least 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 oligos coupled to a surface as provided herein. The oligo array can comprise at most 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 oligos coupled to a surface as provided herein. The oligo array can comprise about 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 oligos coupled to a surface as provided herein. An oligo array as provided herein can have oligos arranged on it at a density of at least 10, 20, 50, 100, 200, 500, 1,000, 2,000, 5,000, 10,000, 20,000, 50,000, 100,000, 200,000, 500,000, 1,000,000, 2,000,000, 5,000,000, 10,000, 000, 20,000,000, 100,000,000, 200,000,000, 500,000,000 or 1,000,000,000 oligos per square millimeter. The oligos on an oligo array as provided herein can be organized into spots (features), regions, or pixels. Oligos in each spot (feature) or region can be identical to each other or related to each other (e.g., all or substantially all include a consensus or common sequence). Oligos in each spot or region can be greater than 55, 60, 65, 70, 75, 80, 85, 90, 95, 99, or 99.9% identical to each other. An oligo array as provided herein can comprise at least 1, 2, 3, 4, 5, 6, 7, 8, 9, 10, 100, 1000, 10,000, 50,000, 100,000, 200,000, 500,000, 1,000,000, 2,000,000, 5,000, 000, 10,000,000, 20,000,000, 100,000,000, 200,000,000, 500,000,000 or 1,000,000,000 spots (features) or regions. Each spot or region can have a size of at most about 1 cm, 1 mm, 500 µm, 200 µm, 100 µm, 10 µm, 9 µm, 8 µm, 7 µm, 6 µm, 5 µm, 4 µm, 3 µm, 2 µm, 1 µm, 800 nm, 500 nm, 300 nm, 100 nm, 50 nm, or 10 nm. In some cases, the oligos are coupled to the polymer coating on the surface. The polymer coating can be a polyacrylamide coating as provided herein. In some cases, a composition as provided herein comprises a surface, a polyacrylamide coating covalently bound to said surface; and at least one oligonucleotide coupled to said polyacrylamide coating.

In some cases, the oligos are incorporated into the polymer coatings (e.g., polyacrylamide coating) during the polymerization process. For example, 5'-acrydite-modified oligonucleotides chains can be added during the acrylamide polymerization process to allow the incorporation of the oligonucleotides into the polymerizing polyacrylamide structure. In some cases, the oligonucleotides are coupled to the polymer coating (e.g., polyacrylamide coating) at the 5' end. In some cases, the oligonucleotides are coupled to the polymer coating (e.g., polyacrylamide coating) at the 3' end. In some cases, some oligonucleotides are coupled to the polymer coating (e.g., polyacrylamide coating) at the 3' end and some oligonucleotides are coupled to the polymer coating (e.g., polyacrylamide coating) at the 5' end.

In some cases, the oligos are incorporated into the polymer coatings (e.g., polyacrylamide coating) after the polymerization process. For example, reactive sites can be added to the polymer (e.g., polyacrylamide) structure during the polymerization process. Oligos can then be incorporated at the reactive sites subsequent to the polymerization of the polymer (e.g., polyacrylamide). The reactive sites can comprise bromoacetyl site, azide sites, or sites that are compatible with azide-alkyne Huisgen cycloaddition. In some cases, the reactive sites comprise bromoacetyl sites. In some cases, the reactive sites comprise azides. In some cases, the reactive sites comprise sites compatible with azide-alkyne Huisgen cycloaddition.

In some cases, the oligos are incorporated into the polymer coatings (e.g., polyacrylamide coating) in a controlled manner, with particular oligos located at particular regions of the polymer coatings (e.g., polyacrylamide coating). Oligos can be incorporated into the polymer coatings (e.g., polyacrylamide coating) at random, with particular oligos randomly distributed throughout the polymer coatings (e.g., polyacrylamide coating).

Oligonucleotide arrays ("oligo") arrays can be fabricated on surfaces prepared as provided herein by various means. The surfaces can comprise surface bound initiator species as provided herein. The surfaces can comprise surface bound initiator species as provided herein with polymer coatings (e.g., polyacrylamide coating) formed on said surface bound initiator species as provided herein. The means can include, but are not limited to, in situ synthesis (e.g., photo-directed synthesis), printing (e.g., ink jet printing), spotting, transfer, bridge amplification, or recombinase polymerase amplification.

In some cases, oligo arrays for use in the methods provided herein are synthesized by in situ synthesis. Oligo regions can be fabricated by in situ synthesis, for example as described in Gao et al., 2004, *Biopolymers*, 73(5):579-596, the disclosure of which is herein incorporated by reference in its entirety. In situ synthesis of oligos on the array surface can be performed by printing; for example, ink jet or other printing techniques which can deliver A, C, G, or T phosphoramidites to specific array regions and thereby control the synthesis at each region. In situ synthesis can be performed by electroreaction; for example, array regions can be contained in individually addressable electroreaction cells, and synthesis at each region can be controlled electrically.

In some cases, oligo arrays for use in the methods provided herein are synthesized by spotting. Spotting can be as described in Gao et al., 2004, *Biopolymers*, 73(5):579-596, the disclosure of which is herein incorporated by reference in its entirety. Noncontact or contact printing methods (e.g., robotic pins, piezoelectric ink jet printers) can be used to deposit pre-synthesized oligos onto oligo or primer regions of the array. Oligos can then be linked or immobilized to the surface, for example by chemical attachment via a functional group. In some cases, the functional group can be bound to the 5' end of the oligo, resulting in oligos with 3' ends away from the surface.

In some cases, in situ synthesis can be performed by photolithography. Photolithography can be performed with or without a mask. In some cases, photolabile protecting groups are used to control synthesis at each array region and patterned with a photomask or with a maskless lithography system.

Figure 4:
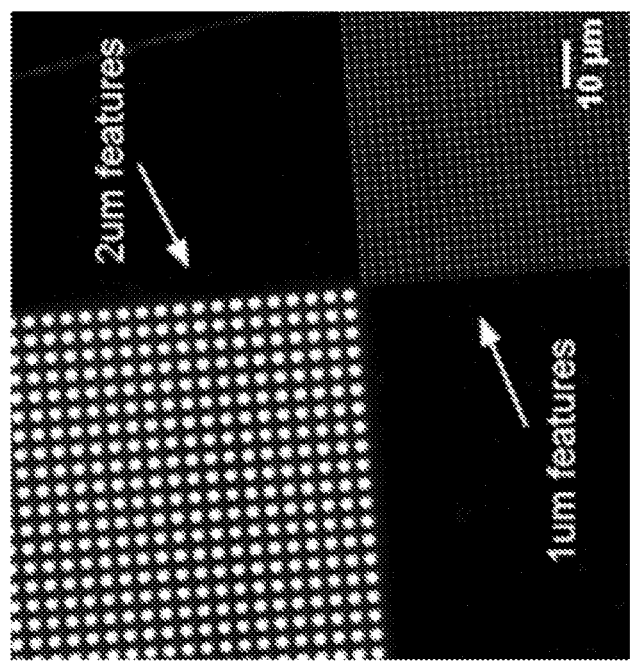
FIG. 4 illustrates a 20-mer oligo array generated using conventional contact lithography stepwise misalignment using photolytic protecting group chemistry.

In some cases, projection lithography and contrast enhancing photo-acid generating polymer films are used in combination to synthesize oligo arrays for use in the methods provided herein. Currently, high-density oligonucleotide ("oligo") arrays of probe lengths up to 60 bp are commercially available from Affymetrix, NimbleGen, and Agilent (i.e., SurePrint Technology) as described in Fodor, S. P. et al. Light-directed, spatially addressable parallel chemical synthesis. Science 251, 767-773, (1991), McGall, G. H. & Christians, F. C. High-density genechip oligonucleotide probe arrays. Adv Biochem Eng Biotechnol 77, 21-42, (2002), and Nuwaysir, E. F. et al. Gene expression analysis using oligonucleotide arrays produced by maskless photolithography. Genome Res 12, 1749-1755, (2002), the disclosure of each of which is herein incorporated by reference in its entirety. However, the smallest feature pitch fabricated in these arrays is 5 µm, 13 µm, and 30 µm respectively. FIG. 4 depicts a 20-mer oligo array generated using conventional contact lithography stepwise misalignment using photolytic protecting group chemistry. As shown in FIG. 4, using conventional contact lithography stepwise misalignment with photolytic protecting group chemistry limited the achievable minimum feature size of the generated oligo arrays to 1 µm to 2 µm. In the methods provided herein, the combined use of projection lithography and contrast enhancing photo-acid generating polymer films can allow resolution at or smaller than 1 μm. This can be beneficial for close packing of barcode features while minimizing cross-talk error. In some cases, oligo arrays generated by combined use of projection lithography and contrast enhancing photoacid generating polymer films comprise 15 million features, each 1 μm×1 μm in size, with a total array size of 3 mm×5 mm. Each oligo on the oligo array can be ~60 bases with an ~20 base barcode, flanked by two ~20 base universal adaptors. Established steppers (e.g. ASML PAS5500) can be used to generate the oligo arrays. Established steppers (e.g. ASML PAS5500) routinely print 5× reduced patterns in the sub-micron range with ±0.060 um placement accuracy The barcode regions can be ≤1 μm, such that each feature ("spot") spans a 2000 bp section of template nucleic acid (e.g., DNA) stretched using a method provided herein across the array. The universal adaptors can comprise a top adaptor and a bottom adaptor. The top adaptor can be used to prime the stretched nucleic acid (e.g., DNA), while the bottom adaptor can serve as the first adaptor for NGS library preparation. The barcode can be a set of oligonucleotide barcodes. The set of barcodes can uniquely identify the spatial position of each oligo on the oligo array or chip. Barcodes can be designed for precision sequence performance, e.g., GC content between 40% and 60%, no homopolymer runs longer than two, no self-complimentary stretches longer than 3, not present in human genome reference. In some cases, to error-proof addressability, each barcode is four deletions or insertions or substitutions away from any other barcode in the array. In some cases, multi-exposure contact lithography with computer assisted overlay alignment is used to reach 1 μm feature resolution using proven photolytic protecting group chemistry.

In some cases, oligo arrays are generated using bridge amplification or recombinase polymerase amplification, for example as described herein as well as in U.S. Provisional Application No. 61/979,448 or 62/012,238, the disclosure of each of which is herein incorporated by reference in its entirety. A substrate for the array can comprise bound adaptors or oligos capable of binding to a region on a separate oligo, permitting bridge amplification or recombinase polymerase amplification of the separate oligo on the substrate. The substrate can be seeded with oligos (i.e., primers) with known barcode sequences, followed by amplification to generate oligo regions. Alternatively, the oligo substrate can be seeded with oligos with random or unknown barcode sequences, followed by amplification to generate oligo regions and sequencing of oligos from each oligo region to determine the barcode sequence corresponding to each oligo region. The substrate can be prepared for the generation of oligo arrays as provided herein.

Figure 5:
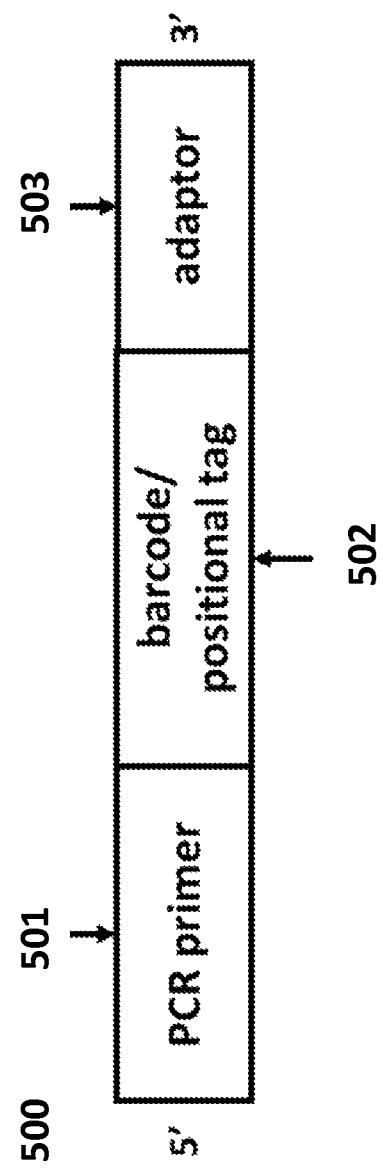
FIG. 5 illustrates a schematic of an oligo 500 that comprises, from 5' to 3', a PCR primer sequence 501, a barcode sequence 502, and a defined sequence (e.g., an adaptor or universal) 503 for binding to a sequence complementary to the defined sequence on a target polynucleotide (i.e., template nucleic acid).

Oligos on an oligo array generated using any of the methods provided herein (e.g., template and/or recipient array) can comprise multiple segments or sequences, such as a PCR or extension reaction primer sequence, a barcode sequence, and an adaptor or universal sequence. For example, FIG. 5 shows a schematic of an oligo 500 that comprises, from 5' to 3', a PCR primer sequence 501, a barcode sequence 502, and a defined sequence for binding 503. The defined sequence (503) can be an adaptor sequence, universal sequence, or a sequence complementary to a specific region of a random primer or a primer binding site introduced into a target polynucleotide by the methods provided herein (e.g., transposon insertion). The 5' end of the oligo can be bound to the array. Oligos on an oligo array as provided herein (e.g., template and/or recipient array) can comprise individual or single segments or sequences. The individual segments can be a PCR or extension reaction primer sequence, a barcode sequence, or an adaptor or universal sequence.

PCR primer sequences in an oligo comprising the PCR primer sequences can be sequences used in PCR reactions using polymerase enzymes, including but not limited to PolI, PolII, PolIII, Klenow, T4 DNA Pol, modified T7 DNA Pol, mutated modified T7 DNA Pol, TdT, Bst, Taq, Tth, Pfu, Pow, Vent, Pab, and Phi-29. For example, reactions can be conducted using Bst polymerase by incubating the template nucleic acid and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20). PCR primer sequences can be used to prime an extension reaction. PCR primer sequences can be used to prime a PCR reaction. Extension products generated from oligos comprising a PCR primer sequence can be amplified with PCR to increase their concentration or quantity prior to sequencing. PCR primer sequences can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bp. PCR primer sequences can be at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases.

Adaptor or universal sequences in an oligo on an oligo array can comprise an adaptor or universal sequence capable of hybridizing to a template or target nucleic acid, either directly (e.g., by hybridizing to a sequence within the template nucleic acid), or indirectly (e.g., by hybridizing to a free primer which is hybridized to a sequence within the template nucleic acid). Adaptor or universal sequences can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. Adaptor or universal sequences can be at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases.

Figure 6B:
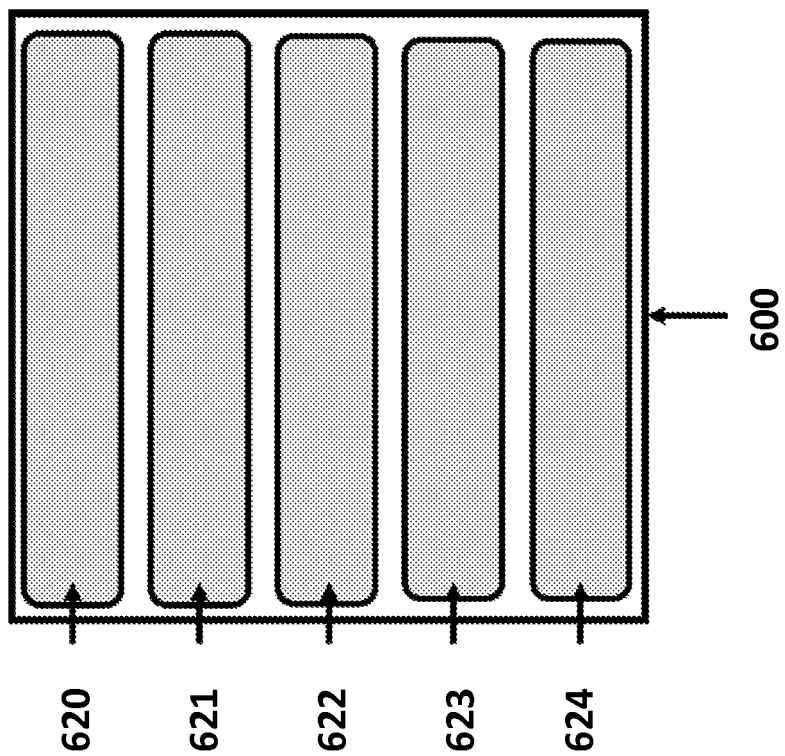
FIG. 6B illustrates a schematic of a substrate with spatially-encoded rows or columns.
Figure 6A:
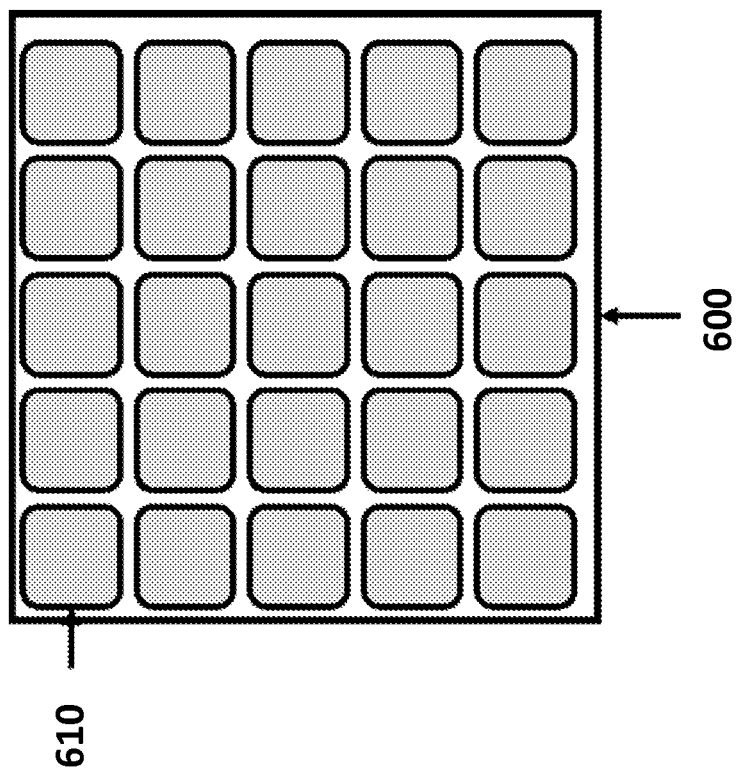
FIG. 6A illustrates a schematic of a substrate with a spatially-encoded array.
Figure 6C:
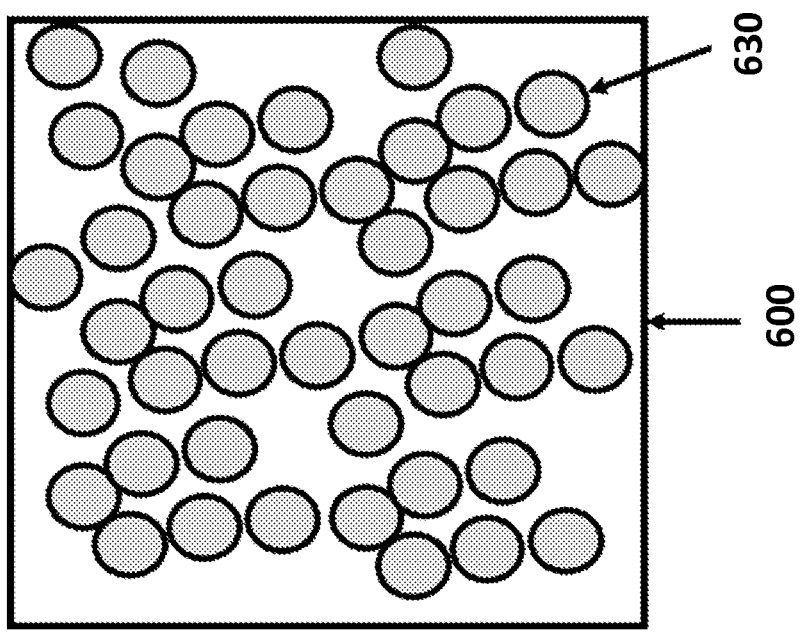
FIG. 6C illustrates a schematic of a substrate with spatially-encoded clusters.

Oligo regions on an oligo array (e.g., template and/or recipient oligo array) can be organized in different arrangements on the oligo array 600. Oligo regions can be arranged on the oligo array in a two-dimensional array of oligo regions 610, for example as shown in FIG. 6A. Oligo regions can be arranged on the oligo array in rows or columns 620, 621, 622, 623, 624 that extend across the oligo array in one direction, for example as shown in FIG. 6B. Oligo regions can be arranged on the oligo array 600 in clusters 630, for example as shown in FIG. 6C.

Oligonucleotides (oligos) can be arranged on the array surface in 5' to 3' orientation or in 3' to 5' orientation. Individual array spots or regions can have dimensions of up to about 15 μm, up to about 14 μm, up to about 13 μm, up to about 12 μm, up to about 11 μm, up to about 10 μm, up to about 5 μm, up to about 3 μm, up to about 1 μm, up to about 0.3 μm, or up to about 0.1 μm. The primer regions can be arranged on the substrate at a density of at least 100, 1,000, 10,000, 100,000, 500,000, 1,000,000, 2,000,000, 5,000,000, 10,000,000, 20,000,000, 50,000,000, 100,000,000, 200,000,000, or 500,000,000 regions per $cm^2$.

Transfer Techniques for Generating Transfer or Recipient Arrays

Figure 7:
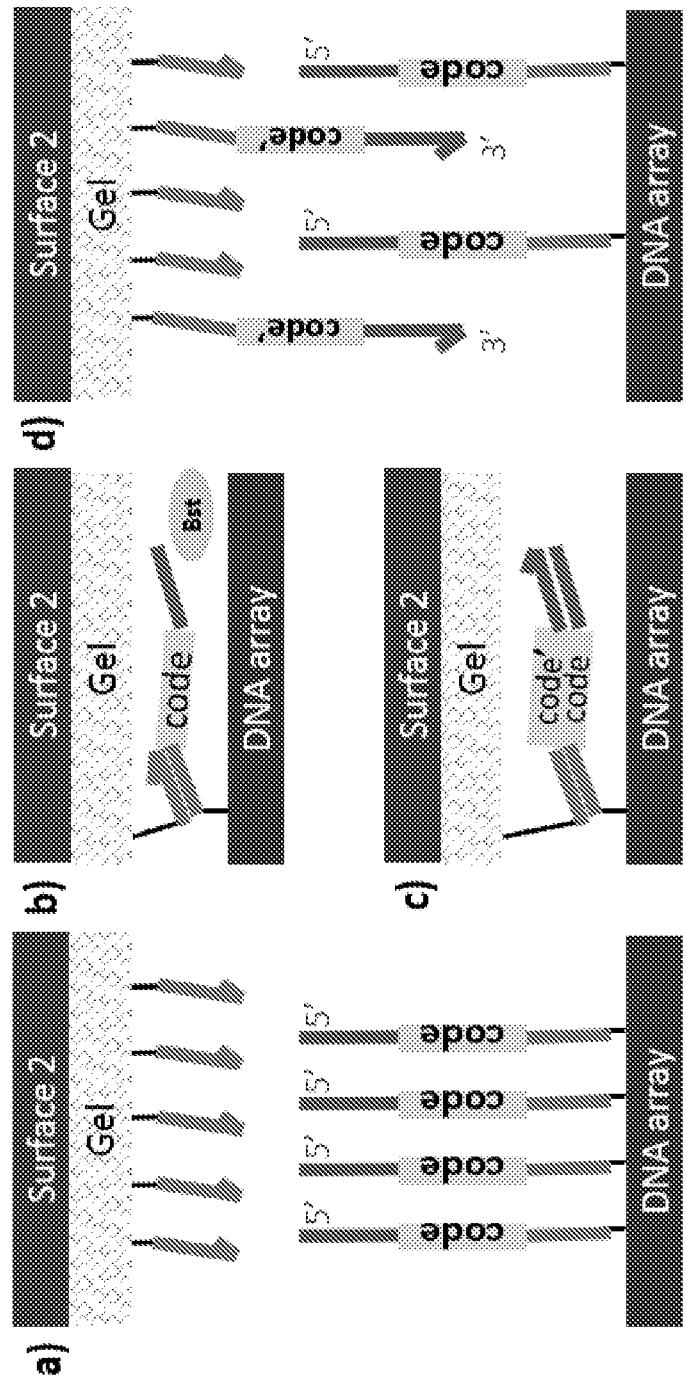
FIG. 7 illustrates a face-to-face enzymatic transfer method used to copy a template nucleic acid (e.g., DNA) array onto a second surface (i.e., recipient array). Synthesized array (5'-up) is pressed against a second, gel covered surface FIG. 7A containing a uniform spread of immobilized primers and the reaction mix. Upon heating, the primers hybridize to the complementary bottom adapters FIG. 7B and are extended via Bst polymerization FIG. 7C. Separating the surfaces produces a 3'-up copy of the original oligo array FIG. 7D.
Figure 8A:
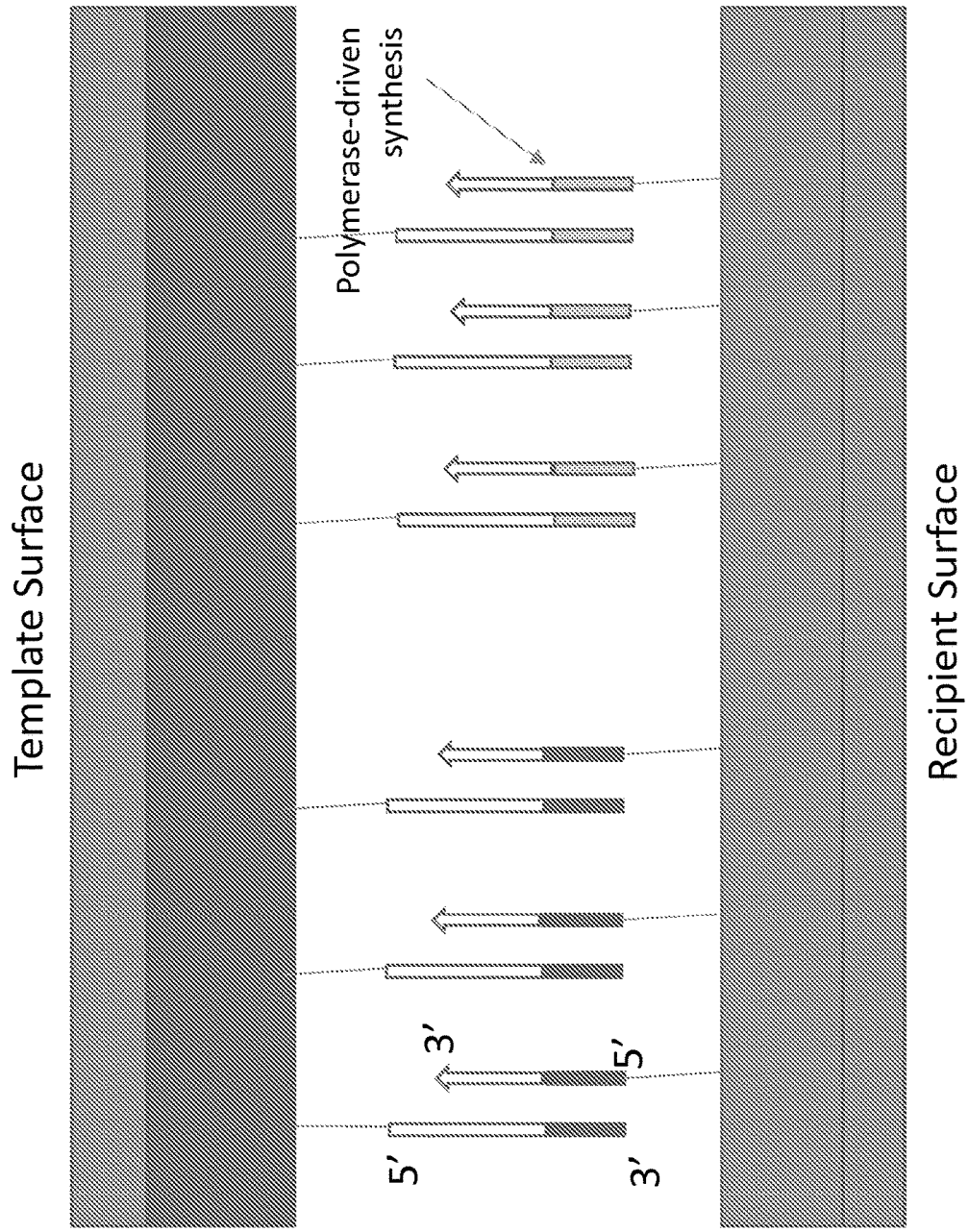
FIG. 8A illustrates a general schematic of enzymatic transfer by synthesis (ETS).
Figure 9:
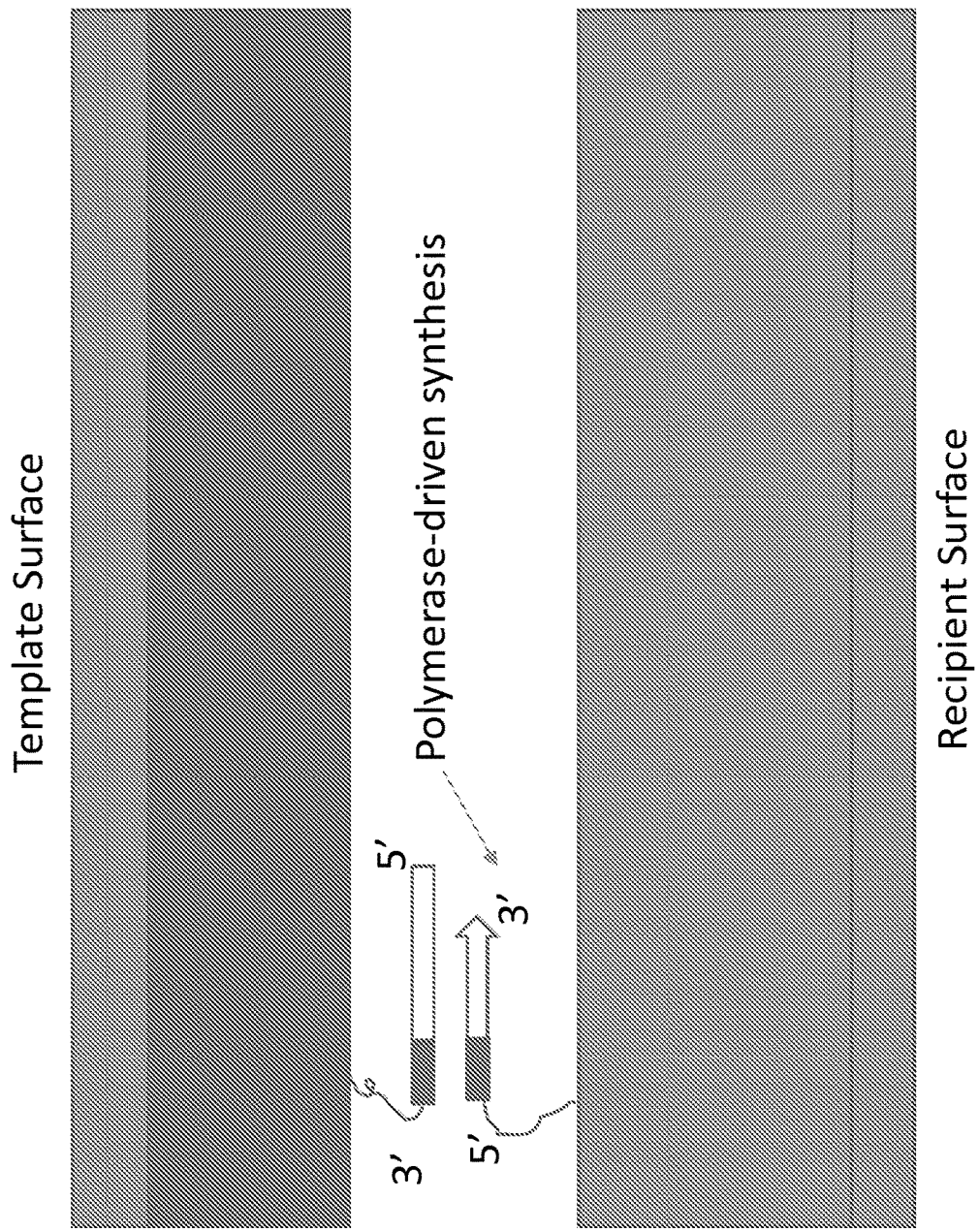
FIG. 9 illustrates a schematic of synthesis on the recipient surface from the template surface.

The methods herein can also be used to generate oligo arrays with a desired orientation. In some cases, the methods for generating oligo arrays as provided herein on surfaces prepared for generating oligo arrays as provided herein are used to generate oligo arrays that are used as templates (i.e., template arrays) for the generation of one or more oligo arrays comprising oligos coupled thereto that are complementary to oligos on the template array. The oligo arrays comprising oligos coupled thereto that are complementary to a template array can be referred to as a recipient array (or alternatively, transfer array). The transfer or recipient oligo arrays can comprise oligos with a desired orientation. The transfer or recipient arrays can be generated from the template array using an array transfer process. In some cases, template oligo arrays with a desired feature ("spot") density (e.g., feature or spot size of about 1 μm) are subjected to an array transfer process as provided herein in order to generate transfer or recipient oligo arrays with a desired orientation. The desired orientation can be a transfer or recipient oligo array that comprises oligos with the 5' end of each oligo of the array attached to the array substrate. A template oligo array for generating the transfer or recipient oligo array with oligos in a desired orientation (i.e., 5' end of each oligo of the array attached to the array substrate) can have the 3' end of each oligo of the template array attached to the substrate. The array transfer process can be a face-to-face transfer process. In some cases, the face-to-face transfer process occurs by enzymatic transfer or enzymatic transfer by synthesis (ETS). ETS is generally depicted in FIGS. 7, 8A, and 9. In some cases, the face-to-face transfer process occurs by a non-enzymatic transfer process. The non-enzymatic transfer process can be oligonucleotide immobilization transfer (OIT). OIT is generally depicted in FIGS. 4 and 5.

The face-to-face gel transfer process (e.g., ETS or OIT) can significantly reduce the unit cost of fabrication while simultaneously flipping the oligo orientation (5' immobilized) which can have assay advantages such as allowing for the enzymatic extension of the 3' ends of the array bound oligos. Moreover, ETS or OIT can result in the transfer of a greater number or higher percentage of oligos of a desired or defined length (i.e., full-length oligo) from the template array to the recipient array. Subsequent amplification (e.g., amplification feature regeneration or AFR as provided herein) of the transferred full length product oligos on the recipient oligo arrays can allow the recipient oligo arrays to contain oligos comprising greater than 50 nucleotide bases without suffering from low yield or partial length products.

In some cases, a template and/or recipient array comprises polymers. The polymers can be aptamers or oligos. In some cases, a template or recipient array comprises oligos. A template or recipient array can have coupled to it at least 10, 20, 50, 100, 200, 500, 1,000, 2,000, 5,000, 10,000, 20,000, 50,000 or 100,000, 200,000, 500,000, 1,000,000, 2,000,000, 5,000,000, 10,000,000, 20,000,000, 100,000,000, 200,000,000, 500,000,000, or 1 billion template polymers (e.g., oligos). A template array can have template polymers arranged on it at a density of at least 10, 20, 50, 100, 200, 500, 1,000, 2,000, 5,000, 10,000, 20,000, 50,000 or 100,000 polymers (e.g., oligos) per square millimeter. The polymers (e.g., oligos) on a template or recipient array can be organized into spots, regions, or pixels. Polymers (e.g., oligos) in each spot or region can be identical to each other or related to each other (e.g., all or substantially all include a consensus or common sequence). Polymers (e.g., oligos) in each spot or region can be greater than 55, 60, 65, 70, 75, 80, 85, 90, 95, 99, or 99.9% identical to each other. The template or recipient array can comprise at least 1, 2, 3, 4, 5, 6, 7, 8, 9, 10, 100, 1000, 10,000, 100,000, 1,000,000, or 10,000,000 spots or regions. Each spot or region can have a size of at most about 1 cm, 1 mm, 500 μm, 200 μm, 100 μm, 10 μm, 9 μm, 8 μm, 7 μm, 6 μm, 5 μm, 4 μm, 3 μm, 2 μm, 1 μm, 800 nm, 500 nm, 300 nm, 100 nm, 50 nm, or 10 nm.

A recipient or transfer array generated as provided herein can comprise oligos that are either fully complementary, fully identical, partially complementary, or partially identical in their sequence and/or number to oligos on the template array from which the recipient array was transferred. Partially complementary can refer to recipient arrays that have at least 40%, 45%, 50%, 55%, 60%, 65%, 70%, 75%, 80%, 85%, 90%, 95%, 96%, 97%, 98%, 99%, or 99.9% sequence complementarity. Partially identical can refer to recipient arrays that have at least 40%, 45%, 50%, 55%, 60%, 65%, 70%, 75%, 80%, 85%, 90%, 95%, 96%, 97%, 98%, 99%, or 99.9% sequence identity. A recipient array can have the same number of oligonucleotides as a template array and/or at least 40%, 45%, 50%, 55%, 60%, 65%, 70%, 75%, 80%, 85%, 90%, 95%, 96%, 97%, 98%, 99%, or 99.9% of the number of oligos as the template array from which the recipient array was transferred.

Array fabrication methods as provided herein can result in arrays having polymers (e.g. oligos) of the designed, desired, or intended length, which can be called full-length products. For example, a fabrication method intended to generate oligos with 10 bases can generate full-length oligos with 10 bases coupled to an array. Array fabrication processes can result in polymers (e.g. oligos) of less than the designed, desired, or intended length, which can be called partial-length products. The presence of partial-length oligos can be within a given feature (spot) or between features (spots). For example, a fabrication method intended to generate oligos with 10 bases can generate partial-length oligos with only 8 bases coupled to an array. That is, a synthesized oligo array can comprise many nucleic acids which are homologous or nearly homologous along their length, but which may vary in length from each other. Of these homologous or nearly homologous nucleic acids, those with the longest length can be considered full-length products. Nucleic acids with length shorter than the longest length can be considered partial-length products. Array fabrication methods provided herein can result in some full-length products (e.g., oligos) and some partial-length products (e.g., oligos) coupled to an array in a given feature (spot). Partial-length products coupled to a particular array or within a given feature can vary in length. Complementary nucleic acids generated from full-length products can also be considered full-length products. Complementary nucleic acids generated from partial-length products can also be considered partial-length products.

A transfer method as provided herein (e.g., ETS or OIT) can be used to increase or enrich the amount or percentage of full-length products (e.g., oligo) coupled to a recipient array surface. Array transfer (e.g., ETS or OIT) can result in a transfer or recipient array comprising at least, at most, more than, less than, or about 30%, 40%, 50%, 55%, 60%, 65%, 70%, 75%, 80%, 85%, 90%, 95%, 96%, 97%, 98%, 99%, or 99.9% transferred oligonucleotides that are 100% of the length of the respective oligonucleotide on a template array used to generate the transfer or recipient array. A transferred oligonucleotide that is 100% of the length (i.e., the same or identical length) of a template oligonucleotide can be referred to as full-length product (e.g., full-length product oligo). A template array fabricated by methods known in that art (e.g. spotting or in situ synthesis) can comprise about 20% oligonucleotides that are a desired length (i.e., full-length oligonucleotides) and about 80% oligonucleotides that are not a desired length (i.e., partial-length oligonucleotides). Transfer of the array generated by methods known in the art comprising about 20% full-length oligonucleotides and about 80% partial-length oligonucleotides using array transfer methods as provided herein can result in the generation of transfer or recipient arrays comprising at most about 20% full-length product oligos. In some cases, an array fabricated according to the methods herein has a greater percentage of oligonucleotides of a desired length (i.e., full length oligos) such that transfer of an array fabricated according to the methods herein using array transfer methods provided herein results in the generation of transfer or recipient arrays with a higher percentage of full-length product oligos as compared to fabrication and transfer methods known in the art.

In some cases, a transfer method provided herein (e.g., ETS or OIT) comprises generation of nucleic acid (e.g., oligo) sequences complementary to the template sequences. The transfer can occur by enzymatic replication (e.g., ETS) or by non-enzymatic physical transfer (e.g., OIT) of array components between array surfaces. The array surfaces can be any array surface as provided herein. The substrate of the template array and of the recipient array can be the same or can be different. The transfer can comprise fabrication of complementary sequences which are already attached to a recipient array; for example, primers bound to a recipient array, and are complementary to adaptors on the template array, can be extended using the template array sequences as templates to thereby generate a full length or partial length recipient array. Transfer can comprise fabrication of complementary sequences from a template array followed by attachment of the complementary sequences to a recipient array.

A transfer method as provided herein (e.g., ETS or OIT) can generate a recipient array such that the orientation of a template nucleic acid (e.g., oligo) relative to its coupled recipient array surface is preserved (e.g., the 3' end of the template nucleic acid (e.g., oligo) is bound to the template array and the 3' end of the transferred nucleic acid (e.g., oligo) complement is bound to the recipient array). Transfer can reverse the orientation of a nucleic acid relative to its coupled array surface (e.g., the 3' end of the template nucleic acid is bound to the template array and the 5' end of the transferred nucleic acid complement is bound to the recipient array).

Array transfer (e.g., ETS or OIT) can be performed multiple times. Array transfer (e.g., ETS or OIT) can be performed multiple times using the same template array. A template array of template polymers bound to a template substrate can be used for the production of at least 1, 2, 3, 4, 5, 6, 7, 8, 9, 10, 20, 30, 40, 50, 60, 70, 80, 90, 100, 500, 1,000, 5,000, 10,000, 50,000, or 100,000 recipient arrays. Array transfer can be performed multiple times in a series of transfers, using the transfer array from one array transfer as the template array for a subsequent transfer. For example, a first transfer can be performed from a template array with oligonucleotides bound to the array at their 3' ends to a first transfer array with complementary oligonucleotides bound to the array at their 5' ends, and a second transfer can be performed from the first transfer array (now serving as a template array) to a second transfer array with a higher percentage of full-length products and sequences matching the original template array than in recipient arrays generated using transfer techniques commonly used in the art while preserving the 5'-surface bound orientation. In some cases, the full-length product oligos on a recipient array generated using the array transfer methods provided herein (e.g., ETS or OIT) are further enriched through amplification of the full-length product oligos on the recipient array. Amplification can be conducted using the methods provided herein. The array transfer method can be a face-to-face enzymatic transfer method (e.g., ETS) or non-enzymatic (e.g., OIT) as provided herein.

In some cases, array transfer by ETS or OIT can be aided by the use of adaptor sequences on the template polymers (e.g., oligos). Polymers (e.g., oligos) can comprise a desired final sequence with the addition of one or more adaptor sequences. For example, a template oligonucleotide can comprise, in order, a 3' end with a first adaptor sequence, a 5' end with a second adaptor sequence, and a desired final sequence in the middle. The first and second adaptor sequences can be the same or can be different. In some cases, oligonucleotides in the same array spot comprise identical first and second adaptor sequences and final sequences, and oligonucleotides in different array spots comprise identical first and second adaptor sequences but different final sequences. Primers on a transfer/recipient array can be complementary to adaptor sequences, allowing hybridization between the primers and the template polymers (e.g., oligos). Such hybridization can aid in the transfer from one array to another.

Figure 10:
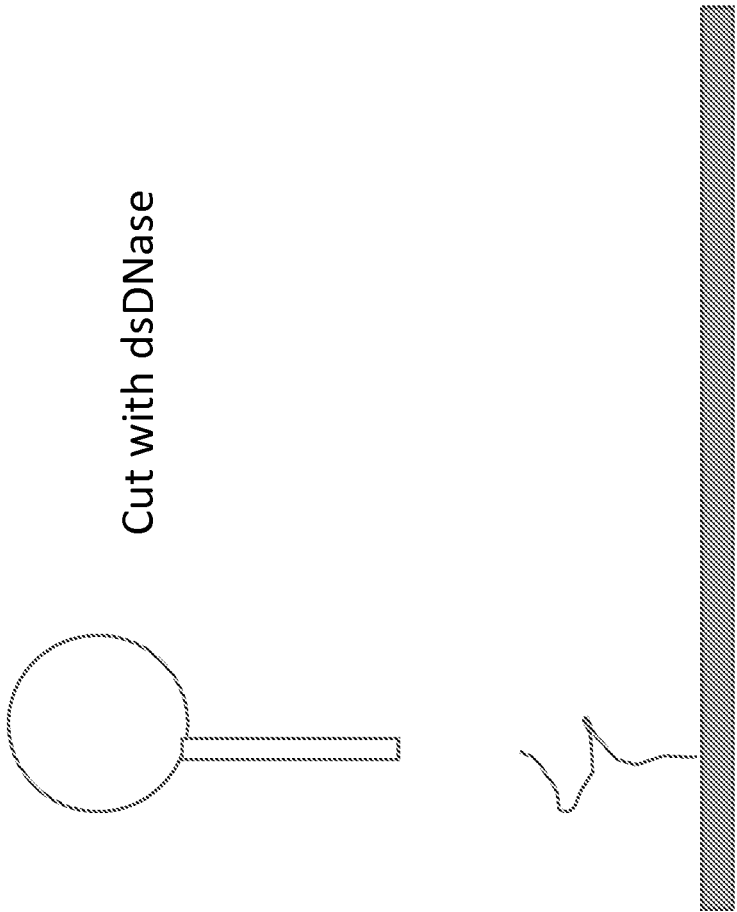
FIG. 10 illustrates a schematic of probe end clipping (PEC) to remove an adapter sequence.
Figure 11:
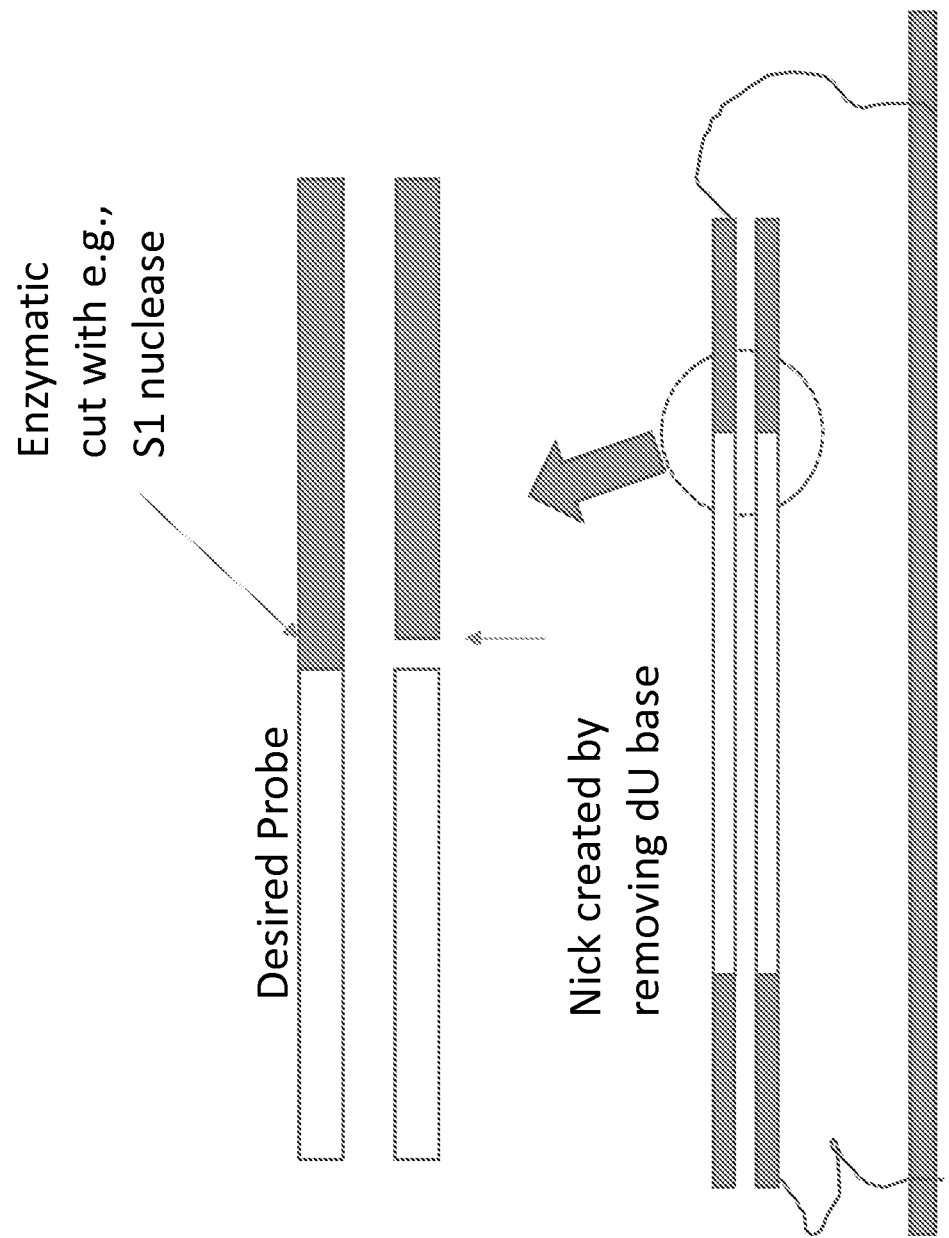
FIG. 11 illustrates a schematic of probe end clipping (PEC) at a nick site.

Some or all adaptor sequences can be removed from transfer/recipient array polymers (e.g. transferred oligonucleotides) after transfer, for example by enzymatic cleavage, digestion, or restriction. Some or all adaptor sequences can be removed from transfer/recipient array polymers (e.g. transferred oligonucleotides) after transfer, for example by enzymatic cleavage, digestion, or restriction. For example, oligonucleotide array components can have adaptors removed via probe end clipping (PEC) by double-strand DNAse. Oligonucleotides complementary to the adaptor sequence can be added and hybridized to the array components. DNAse specific to double-stranded DNA can then be used to digest the oligonucleotides (see FIG. 10). Alternatively, one or more cleavable base, such as a dU, can be incorporated into the primer of the strand to be removed. The primer can then be nicked at the position next to the 3'-most base of the probe, and the nick site can be cut by an appropriate enzyme, such as Mung bean S1 or P1 nuclease (see FIG. 11). Many restriction enzymes and their associated restriction sites can also be used, including but not limited to EcoRI, EcoRII, BamHI, HindIII, TaqI, NotI, HinFI, Sau3AI, PvuII, SmaI, HaeIII, HgaI, AluI, EcoRV, EcoP15I, KpnI, PstI, SacI, SalI, ScaI, SpeI, SphI, StuI, and XbaI. In some cases, the transfer process described above is repeated from the second surface (recipient surface) to a new, third surface containing primers (e.g., oligo) complementary to the top adaptor. Because only the full length oligos can have a complete top adaptor, only these can be copied onto the third array surface (i.e., new or third recipient or transfer array). The process can purify or enrich the full length oligos from the partial products, thus creating a high feature density, high quality full length oligo array. Purification or enrichment can mean the generation of a recipient array such that said recipient array has a greater percentage or number of oligos of a desired length (i.e. full-length) than the array used as a template for the generation of said recipient array. The full-length oligos can be oligos that contain all the desired features (e.g., adaptor(s), barcode(s), target nucleic acid or complement thereof, and/or universal sequence(s), etc.).

In some cases, array transfer can be aided by the flexibility or deformability of the array (e.g., template array) or of a surface coating on the array (e.g., template array). For example, an array (e.g., template array) comprising a polyacrylamide gel coating with coupled oligonucleotides can be used in array transfer (e.g., ETS, OIT). The deformability of the gel coating can allow for array components (oligos, reagents (e.g., enzymes)) to contact each other despite surface roughness. Surface roughness can be variability in the topography of the surface.

Array components can be amplified or regenerated by enzymatic reactions termed as amplification feature regeneration (AFR). AFR can be performed on template arrays and/or recipient arrays. AFR can be used to regenerate full-length oligos on an array (e.g., template and/or recipient) in order to ensure that each oligo in a feature (spot) on an array (e.g., template and/or recipient array) comprises desired components (e.g., adaptor(s), barcode(s), target nucleic acid or complement thereof, and/or universal sequence(s), etc.). AFR can be conducted on oligos comprising adaptor and/or primer binding sites (PBS) such that the oligos each comprise a first adaptor (or first PBS), probe sequence, and second adaptor (or second PBS). Preferably, the oligos in each feature on an array (e.g., template and/or recipient array) comprise two or more primer binding sites (or adaptor sequence). AFR can be performed used nucleic amplification techniques known in the art. The amplification techniques can include, but are not limited to, isothermal bridge amplification or PCR. For example, bridge amplification can be conducted on array (e.g., template and/or recipient array) component oligonucleotides via hybridization between adaptor sequences on the array (e.g., template and/or recipient array) components and surface-bound oligonucleotide primers, followed by enzymatic extension or amplification. Amplification can be used to recover lost array (e.g., template and/or recipient array) component density or to increase density of array (e.g., template and/or recipient array) components beyond their original density.

Immobilized oligos, nucleotides, or primers on an array as provided herein (e.g., template and/or recipient array) can be equal in length to each other or can have varying lengths. Immobilized oligos, nucleotides, or primers can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 bases. In some cases, immobilized oligos, nucleotides, or primers are 71 bases long (71-mer).

The recipient surface of the transfer array can be brought into close proximity or contact with the template surface of the template array. In some cases, contact between the template array and the transfer array can be aided by the presence of a deformable coating, such as a polymer gel (e.g., polyacrylamide). The deformability of the coating can allow coupled polymers (e.g. oligonucleotides or primers) to come into close enough contact for hybridization to occur. The deformability of the coating can help overcome gaps due to surface roughness (e.g., surface topography variability) or other features that would otherwise prevent close enough contact for hybridization. An additional benefit of the deformable coating is that it can be pre-loaded with enzymatic reaction reagents, and thus serve as a reservoir for the interfacial reaction of enzymatic transfer by synthesis (ETS). One or both of the arrays can comprise a substrate with a gel coating with polymer molecules coupled to it. For example, the transfer array can comprise a substrate coupled to a polyacrylamide gel with oligonucleotide primers coupled to the gel. Surfaces and coatings are further discussed elsewhere in this disclosure.

Enzymatic Transfer by Synthesis (ETS)

ETS can comprise a face-to-face polymerase extension reaction as depicted in FIGS. 7, 8A, and 9 to copy one or more template oligos (e.g., DNA oligo) from a template oligo array onto a second surface (e.g., recipient array). A second surface (e.g., recipient array) with uniform coverage of immobilized primers complimentary to sequence on an oligo in the template oligo array (e.g., the bottom adaptor sequence in oligo arrays comprising adaptor sequence) can be pressed into contact with the template oligo (e.g., DNA oligo) array. A recipient array surface can comprise surface immobilized oligomers (oligos), nucleotides, or primers that are complementary, at least in part, to template nucleic acids or oligos on the template oligo array. In some cases, a transfer or recipient array comprises oligos that selectively hybridize or bind to aptamers on a template array. Immobilized oligos, nucleotides, or primers on a transfer or recipient array can be complementary to adaptor regions on template polymers (e.g. oligos).

An Example of an ETS array transfer process as provided herein is illustrated in FIGS. 8A-C. The template nucleic acids (oligos) can hybridize with the immobilized primers or probes on the recipient surface, also called recipient primers or probes or transfer primers or probes. The hybridized complex (e.g., duplex) can be extended enzymatically (see FIG. 8A) such as, e.g., by DNA polymerase including but not limited to PolI, PolII, PolIII, Klenow, T4 DNA Pol, modified T7 DNA Pol, mutated modified T7 DNA Pol, TdT, Bst, Taq, Tth, Pfu, Pow, Vent, Pab, and pyrophage.

The transfer process can preserve the orientation of the oligonucleotides, i.e. if the 5' end is bound to the template surface, the 5' end of the synthesized oligonucleotide will be bound to the recipient surface, or vice versa. As shown in FIG. 8A, transfer primers bound at their 5' ends can bind to the template nucleic acids at their 3' ends, followed by enzymatic extension to produce nucleic acids complementary to the template oligos and bound to the recipient array surface at their 5' ends.

In some cases, only full-length template nucleic acid products are used to generate complements on the recipient array. FIG. 8C shows an example of enzymatic transfer (i.e., ETS) using only full-length template nucleic acid products, which comprise a first adaptor region A, a middle region B, and a second adaptor region C. In FIG. 8C, the recipient array surface comprises primers that are complementary to the second adaptor sequence C at the end of the template nucleic acid. Full-length products on the template array comprise the whole sequence (i.e., first adaptor A-middle region B-second adaptor C) and partial-length products do not (i.e., first adaptor A-middle region B). In FIG. 8C, partial-length products on the template array are not transferred because they lack the second adaptor C and thus cannot be bound by the primer (oligo) on the recipient array that comprises sequence complementary to second adaptor C. In some cases, at least 30%, 40%, 50%, 60%, 70%, 80%, 90%, 95%, 96%, 97%, 98%, 99%, 99.9% or 100% of template nucleic acid oligos on the template array are full-length products (oligos). In some cases, at least 30%, 40%, 50%, 60%, 70%, 80%, 90%, 95%, 96%, 97%, 98%, 99%, 99.9% or 100% of transfer or recipient nucleic acid products (oligos) generated on the recipient array are full-length products. The generation of partial-length products on the recipient array during ETS can be due to incomplete extension of full-length template oligos during polymerase-driven synthesis. The generation of full-length products on the recipient arrays can be accomplished using AFR as provided herein.

In some cases, the recipient array includes on it primers that hybridize a portion of the template polymers (e.g., oligos) such that extension reactions occur until all of the template polymers (e.g., oligos) are used as templates for synthesis of a complementary recipient oligos on a complementary array (or recipient array). In some instances, synthesis of the recipient array occurs such that on average at least 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, or 50% of the template polymers (e.g., oligos) are used to generate complementary sequences on the recipient array. Stated differently, a recipient array, post-transfer, can comprise recipient nucleotides (e.g., oligos) synthesized using at least 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, or 50% of the template oligonucleotides as templates.

The array transfer process (e.g., ETS) can invert the orientation of the template nucleic acids (see FIG. 8B, FIG. 9). That is, if the 5' end is bound to the template surface, the 3' end of the synthesized oligonucleotide will be bound to the recipient surface, or vice versa. For example, FIG. 8B shows an enzymatic transfer (i.e., ETS) of template nucleic acids (e.g., oligos) on the surface of a template array which can comprise some or all of a first adaptor region A, a middle region B, and a second adaptor region C. In FIG. 8B recipient surface primers (A') that are complementary to an adaptor sequence located at the substrate end of the template nucleic acids and is designated A are used to conduct enzymatic transfer. In this case, both partial-length and full-length complementary products (oligos) are transferred, and their orientation relative to the substrate surface of the template array is reversed.

As shown in FIG. 9, template nucleic acids (e.g., oligos) bound to the template array surface (template surface) at their 3' ends can hybridize to transfer primers on the recipient array bound to the recipient array surface at their 5' ends. Enzymatic extension of the transfer primers produces nucleic acids (e.g., oligos) complementary to the template nucleic acids (e.g., oligos) and bound to the recipient array surface at their 5' ends. In some cases, partial-length oligos in a feature (spot) of the template array) are utilized to generate complementary partial length oligos on a recipient array. In some cases, full-length oligos in a feature (spot) of the template array are utilized to generate complementary full-length oligos on a recipient array.

The template and recipient surfaces can be biocompatible, such as polyacrylamide gels, modified polyacrylamide gels, PDMS, silica, silicon, COC, metals such as gold, chrome, or chromium, or any other biocompatible surface. If the surface comprises a polymer gel layer, the thickness can affect its deformability or flexibility. The deformability or flexibility of a gel layer can make it useful in maintaining contact between surfaces despite surface roughness. Details of the surfaces are further discussed herein.

Reagents and other compounds including enzymes, buffers, and nucleotides can be placed on the surface or embedded in a compatible gel layer. The enzymes can be polymerases, nucleases, phosphatases, kinases, helicases, ligases, recombinases, transcriptases, or reverse transcriptases. In some cases, the enzymes on the surface or embedded in a compatible gel layer comprise a polymerase. Polymerases can include, but are not limited to, PolI, PolII, PolIII, Klenow, T4 DNA Pol, modified T7 DNA Pol, mutated modified T7 DNA Pol, TdT, Bst, Taq, Tth, Pfu, Pow, Vent, Pab, Phusion, pyrophage and others. Details of the surfaces are further discussed herein. In some cases, the enzymes on the surface or embedded in a compatible gel layer comprise a ligase. Ligases can include, but are not limited to, $E.$ $coli$ ligase, T4 ligase, mammalian ligases (e.g., DNA ligase I, DNA ligase II, DNA ligase III, DNA ligase IV), thermostable ligases, and fast ligases.

Figure 12:
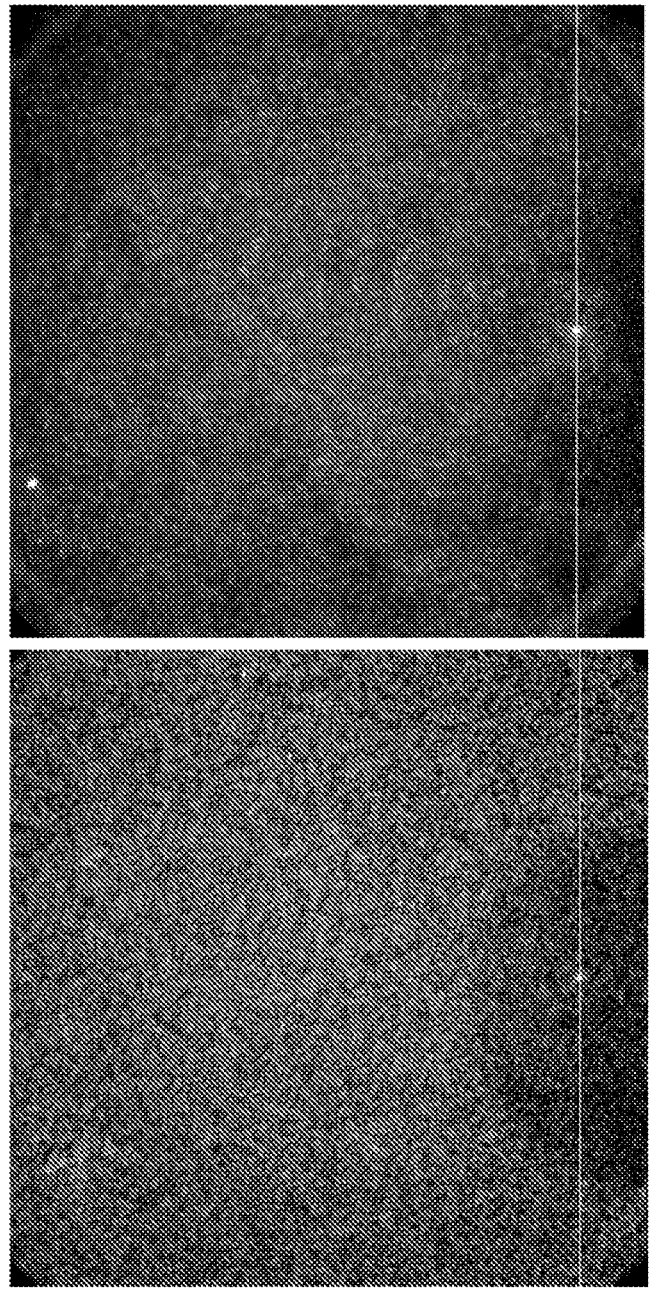
FIG. 12 illustrates template slide (left) and gel chip (right) with clusters transferred via enzymatic extension.
Figure 13:
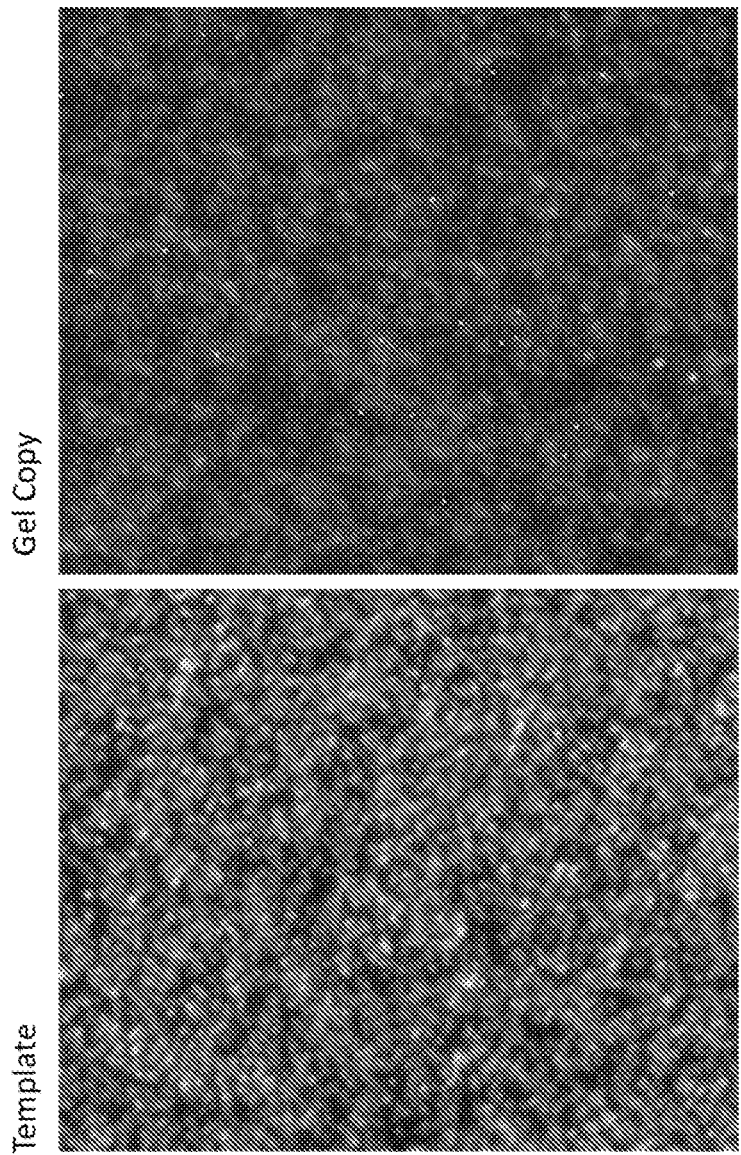
FIG. 13 illustrates zoomed in image of the template (left) and gel copy (right) from FIG. 12.
Figure 14:
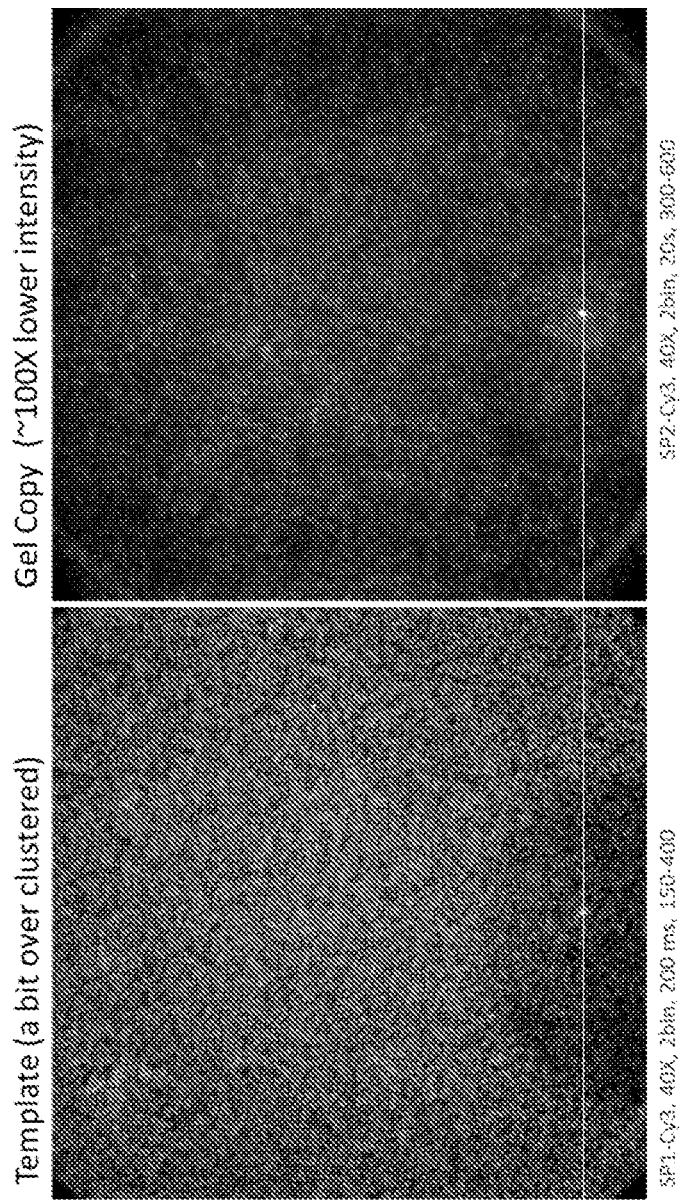
FIG. 14 illustrates a comparison in intensity of a template (left) and gel copy (right), the latter having ~100× lower intensity than the former.
Figure 15:
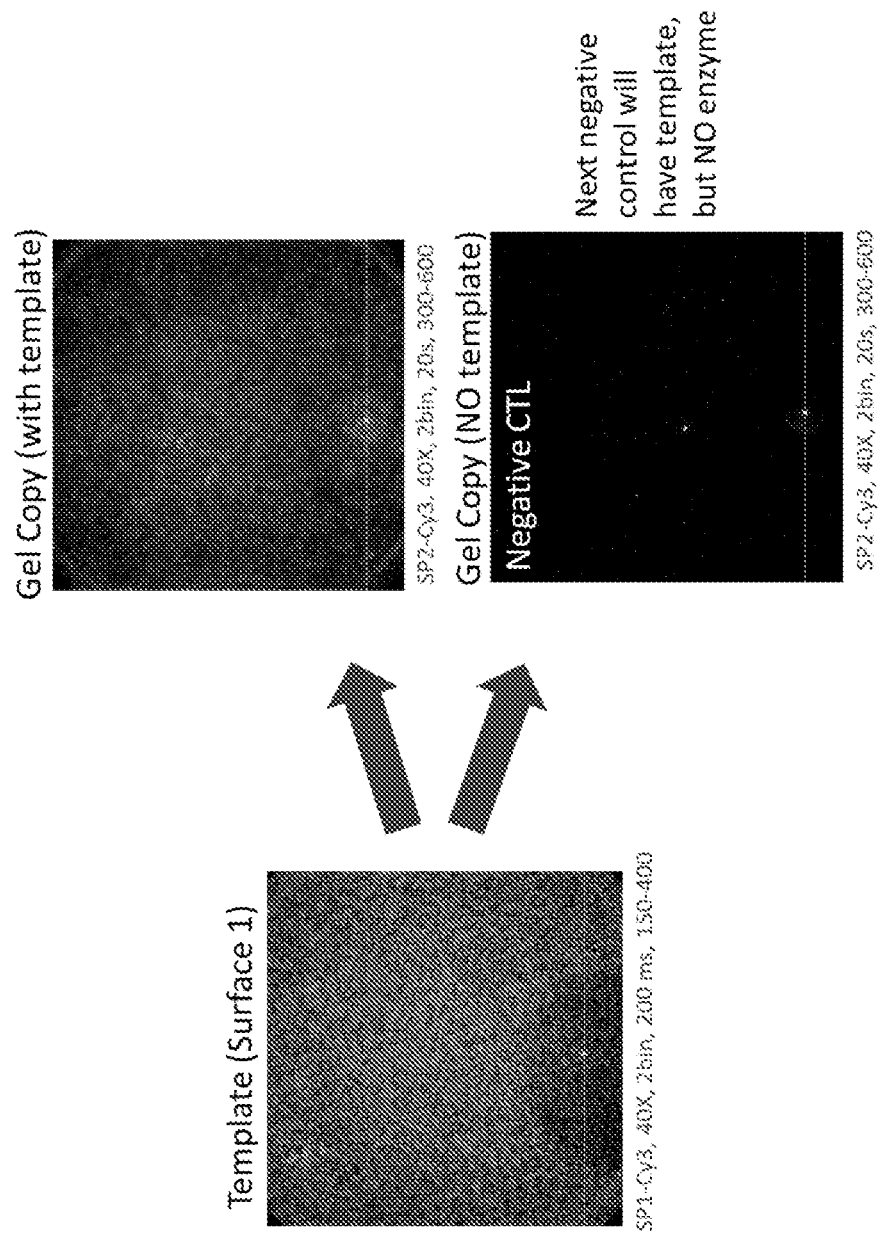
FIG. 15 illustrates enzymatic transfer to a gel copy compared to a negative control surface with no template present.
Figure 16:
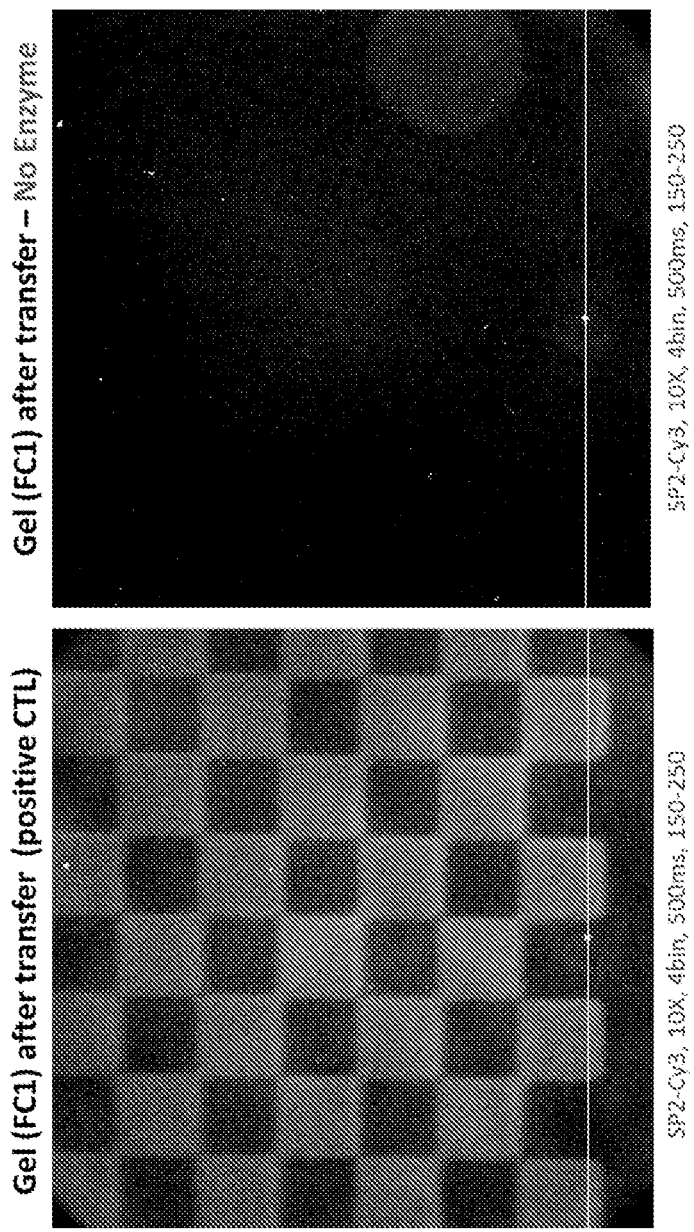
FIG. 16 illustrates enzymatic transfer to a gel copy (left) compared to a negative control surface with no enzyme present (right).

A template surface and a post-transfer recipient surface generated by enzymatic extension are shown in FIGS. 12, 13, and 14. The surface of the recipient array can be a gel formed on top of the template array. FIG. 15 shows an example of an enzymatic extension reaction as described herein from a template array surface to a recipient surface (i.e., Gel Copy (with template)) in the presence of a reaction mixture (e.g., primers, enzymes, buffers as outlined herein) and template as well as a negative control where a template array is subjected to an enzymatic extension reaction as described herein to a recipient surface (Gel Copy (NO template)) in the presence of a reaction mixture (e.g., primers, enzymes, buffers as outlined herein) but no template nucleic acids. The lack of fluorescence in the negative control (i.e., Gel Copy (NO template)) demonstrates a lack of product generated in the absence of template nucleic acids. FIG. 16 shows results from an additional control experiment, wherein a template array surface (left) was contacted with a recipient transfer surface in the presence of a reaction mixture (i.e., primers, buffers) (right) but in the absence of enzyme. The lack of fluorescence on the recipient array (right) in FIG. 16 demonstrates a lack of transfer. The reaction mixture can be placed on the surface of the recipient array or embedded in a recipient surface. In some cases, the reaction mixture is placed on the surface of the recipient array. In some cases, the reaction mixture is embedded in the recipient surface. The recipient surface can be a compatible gel layer. The reaction mixture can comprise any reagent necessary to conduct enzymatic transfer by synthesis (ETS). The reagents can comprise Enzymatic transfer of a template array by ETS can be conducted as follows: 1.) enzyme mix is prepared (e.g., 37 µL H$_2$O, 5 µL 10× Thermopol buffer, 5 µL of 10 mg/mL BSA, 1 µL of 10 mM dNTPs, and 2 µL of 8 U/µL Bst enzyme); 2.) enzyme mix is applied to a recipient array (e.g., an acrylamide gel coated glass slide with coupled oligonucleotide primers prepared as described elsewhere in this disclosure); 3.) a template array is placed face-to-face with the and allowed to react (e.g., clamped together in a humidity chamber for 2 hours at 55° C.); 4.) the template and recipient arrays are separated (e.g., loosened by application of 4×SSC buffer and pulled apart with the aid of a razor blade); 5.) the template array is rinsed (e.g., in DI water) and dried (e.g., with N$_2$); and 6.) the recipient array is rinsed (e.g., with 4×SSC buffer and 2×SSC buffer). In some cases, the oligos on the template array comprise adaptors, such that a bottom adaptor is located proximal to the template array surface, while a top adaptor is located distal from the template array surface. While the sandwich is heated to 55° C., Bst polymerase in Thermopol PCR buffer can extend the primers from the recipient array hybridized to the bottom adaptor of the template array, which can create a dsDNA molecular bridge between the template and recipient array surfaces. Upon physical separation, the second surface (i.e., recipient array) can contain the complementary ssDNA barcode array with the 5' end of the oligos attached to the surface and the 3' end available for polymerase extension. Since both the uniformly dispersed primer on the template array and the barcode oligos on the recipient array can be tethered to their respective surfaces, the relative locations of the transferred features can be maintained (in mirror image). To achieve intimate contact and thus uniform transfer over the full chip area, a broad range of surface materials (PDMS, Polyacrylamide), thicknesses, and process conditions can be used. FIG. 3 shows an example of a face-to-face enzymatic transfer process as described herein on a large (~150 µm) feature array. The efficiency of face-to-face transfers can result in reduced density of oligos within each copied array feature. One of skill in the art can appreciate that the transfer conditions can be optimized by, for example, varying the gel transfer conditions, e.g. choice of enzyme, process temperature and time, length of primers, or surface material properties. Alternatively, post-transfer surface amplification via solid-phase PCR (e.g. bridge-PCR) can be used increase the barcode density to the desired level as described herein.

Oligonucleotide Immobilization Transfer (OIT)

Figure 17:
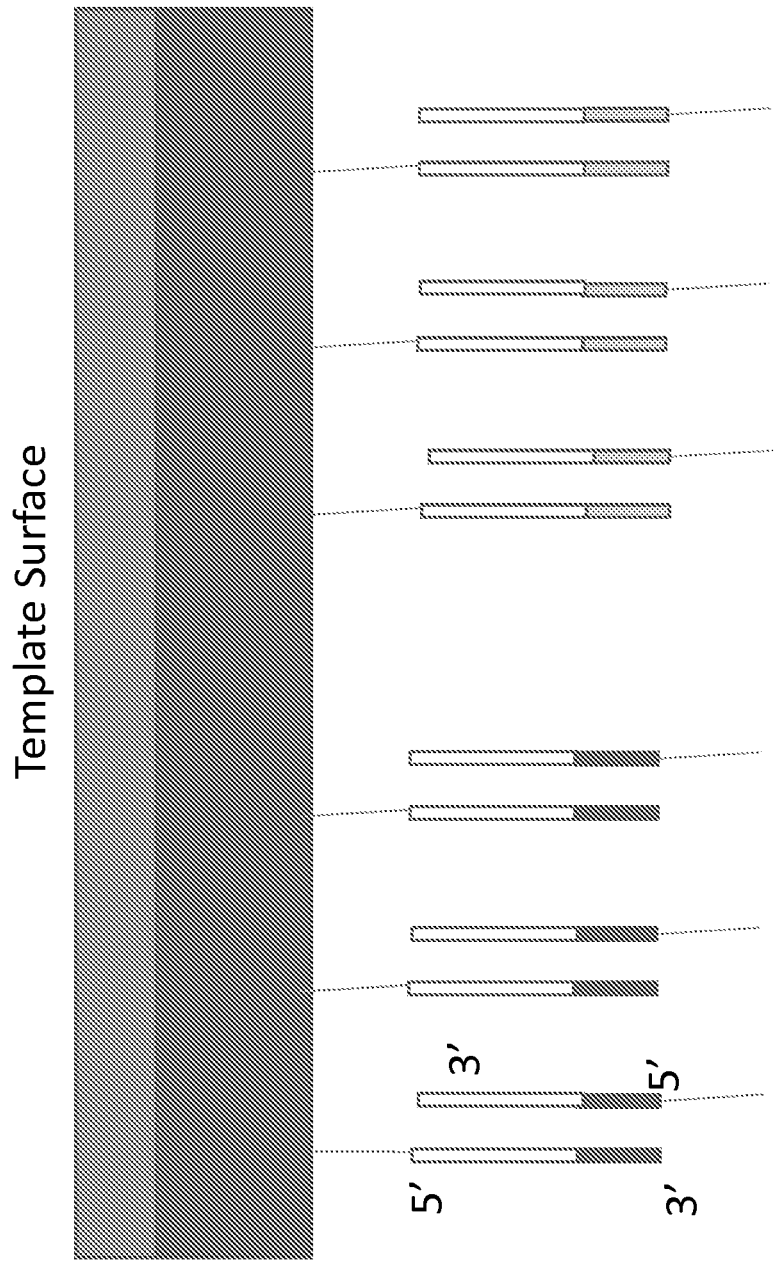
FIG. 17 illustrates a schematic of a first stage of oligonucleotide immobilization transfer (OIT).
Figure 18:
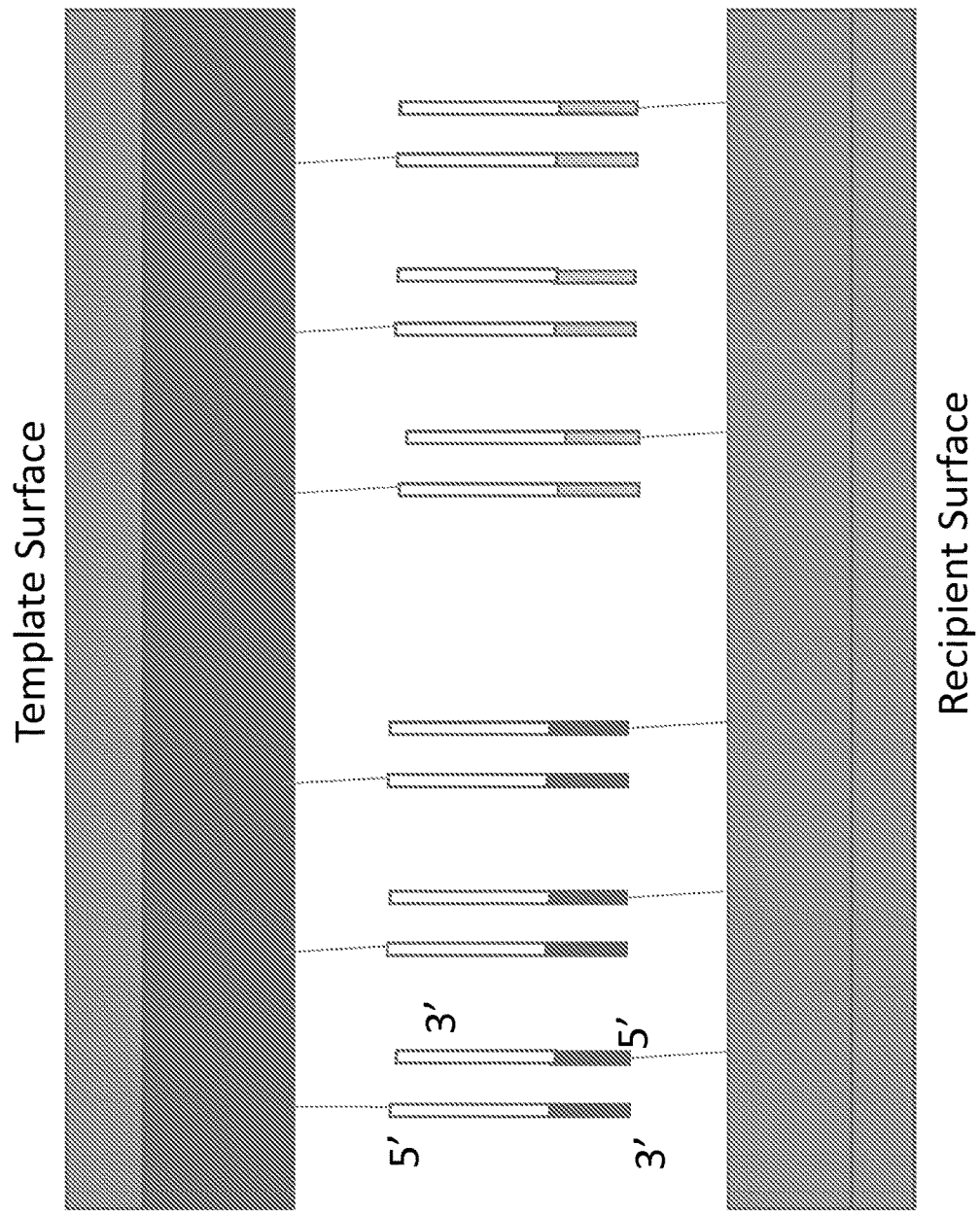
FIG. 18 illustrates a schematic of a second stage of oligonucleotide immobilization transfer (OIT).

In some instances, the generation of a recipient array is performed by non-enzymatic transfer. One form of non-enzymatic transfer is oligonucleotide immobilization transfer (OIT). In OIT, the template nucleic acids (e.g., oligo) on a template array can be single-stranded. Primers comprising sequence complementary to a portion of the template oligos can hybridize to the template oligos and be extended by primer extension in order to generate and can be made double-stranded template oligos on the template array. The primers used for primer extension can be in solution. Many polymerases can be used for OIT, including PolI, PolII, PolIII, Klenow, T4 DNA Pol, modified T7 DNA Pol, mutated modified T7 DNA Pol, TdT, Bst, Taq, Tth, Pfu, Pow, Vent, Pab, Phusion and others. In some cases, the primers used for primer extension comprise linkers that are used to immobilize or bind strand of the double-stranded template oligo generated by primer extension (see FIG. 17) on a surface of a recipient array. The recipient array surface can be a planar surface, a bead, or a gel as provided herein. In some cases, the recipient array surface is a polyacrylamide gel formed during OIT (as shown in FIG. 18). In some cases, subsequent to extension, the linkers can be bound to a recipient array surface. The recipient array surface can be any array surface as provided herein such as a polymer gel or modified glass surface. In OIT, the template and recipient array surfaces can be then be separated. The DNA (i.e., double-stranded template oligos) can be melted prior to separation.

Figure 19:
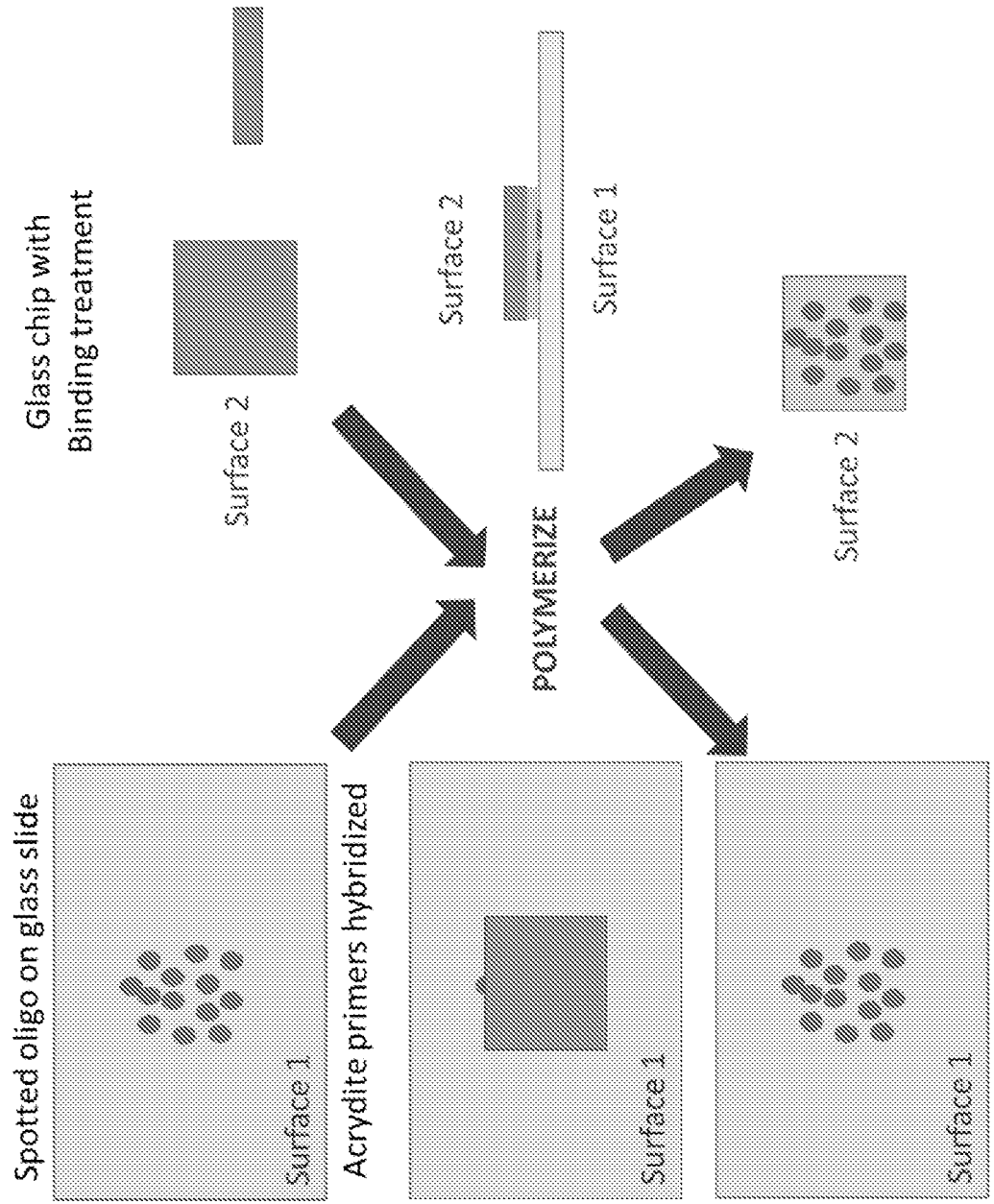
FIG. 19 illustrates a schematic of non-enzymatic gel transfers.
Figure 20:
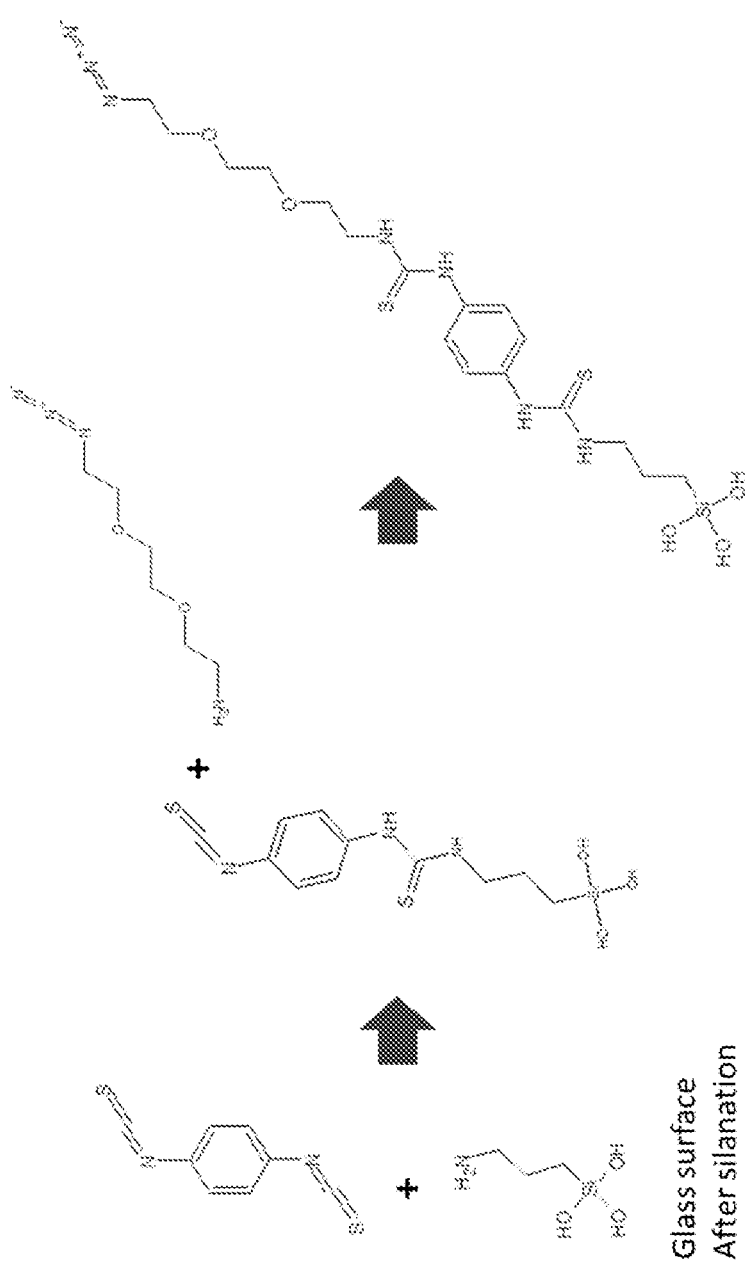
FIG. 20 illustrates a schematic of the first stage of the attachment of oligonucleotides to a glass surface after silanation using the cross-linker 1,4-Phenylene Diisothiocyanate (PDITC).
Figure 21:
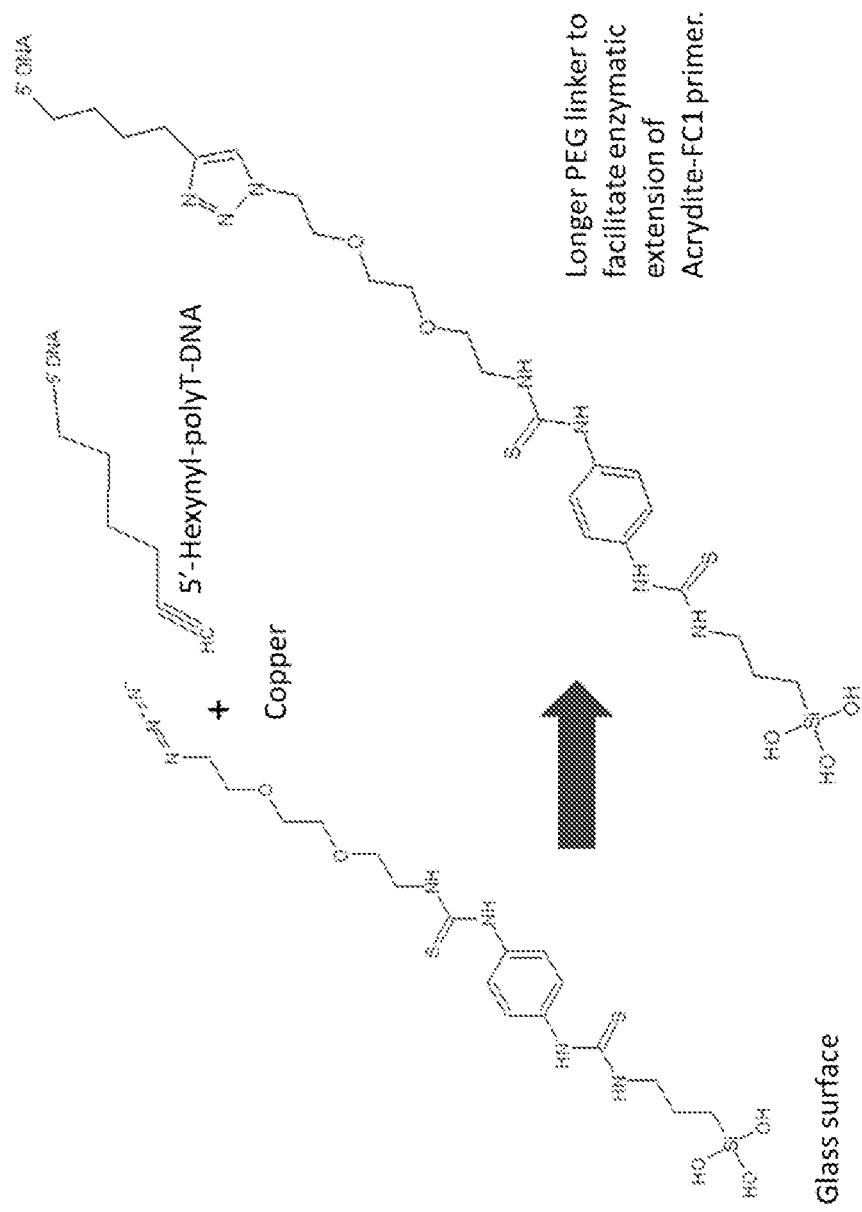
FIG. 21 illustrates a schematic of the second stage of the attachment of oligonucleotides to a glass surface after silanation using PDITC.
Figure 22:
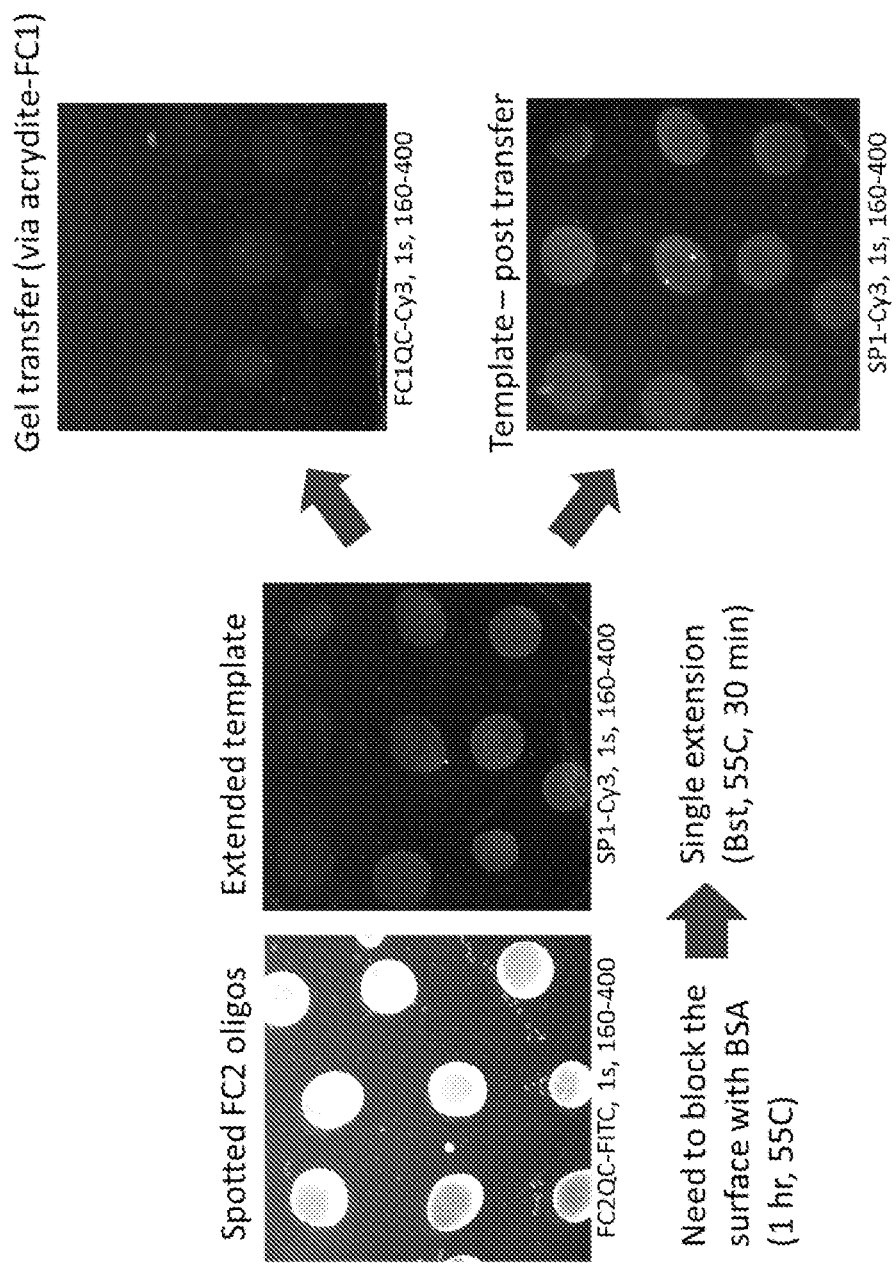
FIG. 22 illustrates gel transfer of oligonucleotides attached to a silanated glass surface using PDITC as illustrated in FIGS. 20-21.
Figure 23:
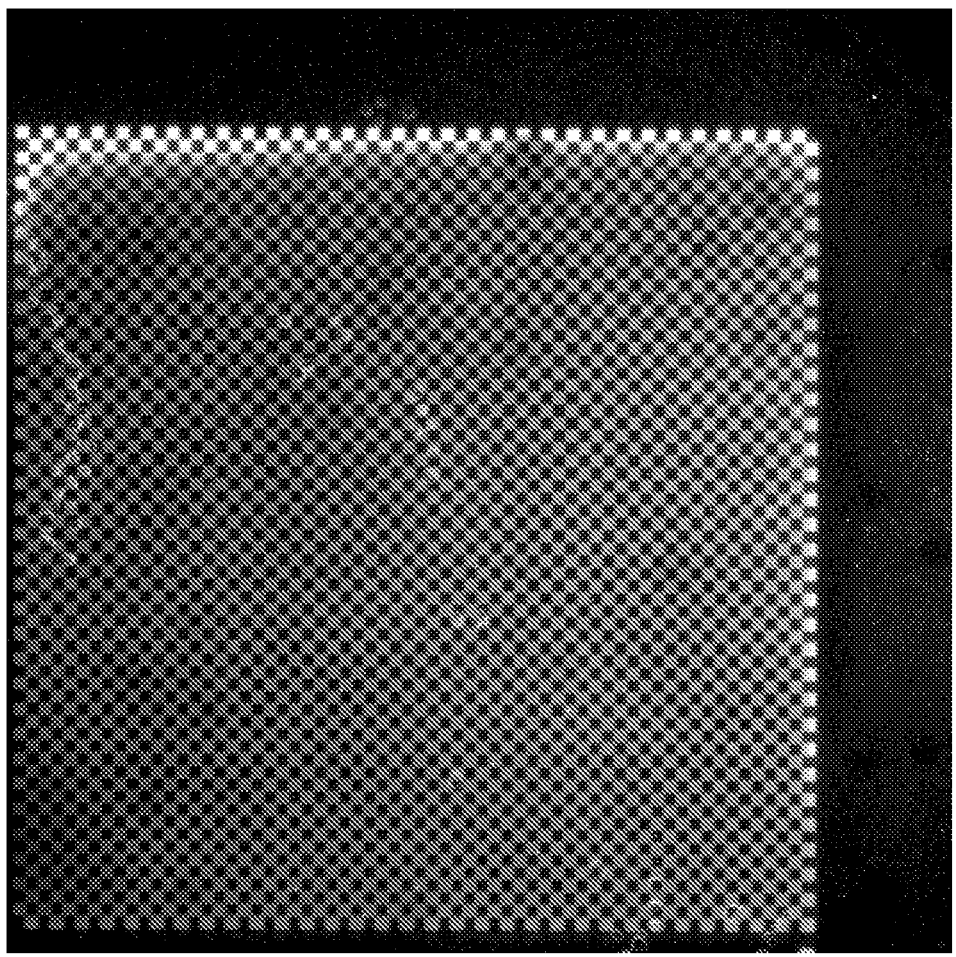
FIG. 23 illustrates a template array comprising fluorescently labeled oligos attached to the surface in a checkerboard pattern.

In some cases, the primers used in OIT are 5'-acrydite modified primers. The 5'-acrydite modified primers can be capable of incorporation into a polymer gel (e.g., polyacrylamide) during polymerization as provided herein. Extension products from the template nucleic acids (e.g., oligos) can then be generated with the acrydite primers, contacted with a substrate with a binding treatment (e.g., unpolymerized polyacrylamide coating precursor), incorporated during polymerization, and separated (see FIG. 19 for an illustration). The primers can be 5'-hexynyl-polyT-DNA. In some cases, primer extension products from the template nucleic acids are generated via binding and extension of complementary 5'-hexynyl-polyT-DNA primers. Following extension, the 5'hexynyl-polyT-DNA primers can be: 1.) contacted with a substrate with a binding treatment (such as glass treated with silane), 2.) linked to a cross-linker such as, for example, a homobifunctional linker such as 1,4-Phenylene Diisothiocyanate (PDITC), 3.) linked to an N3 bonding group with a PEG linker, (e.g., FIG. 20), 4.) bonded to the substrate at the N3 group (e.g., FIG. 21), and 5.) separated during a second stage of OIT (FIG. 18). Examples of PDITC-N3 attachment of nucleic acids are shown in FIGS. 22 and 23. The surfaces can be any of the surfaces as discussed herein. Other cross-linkers that can be used in place of PDITC can include dimethyl suberimidate (DMS), disuccimidyl carbonate (DSC) and/or disuccimidyl oxylate (DSO). This process can preserve the orientation of the oligonucleotides, i.e. if the 5' end is bound to the template array surface, the 5' end of the synthesized oligonucleotide will be bound to the recipient array surface, or vice versa. While enzymatic extension can be used prior to the transfer, the transfer itself can be conducted without enzymatic reactions.

Figure 24:
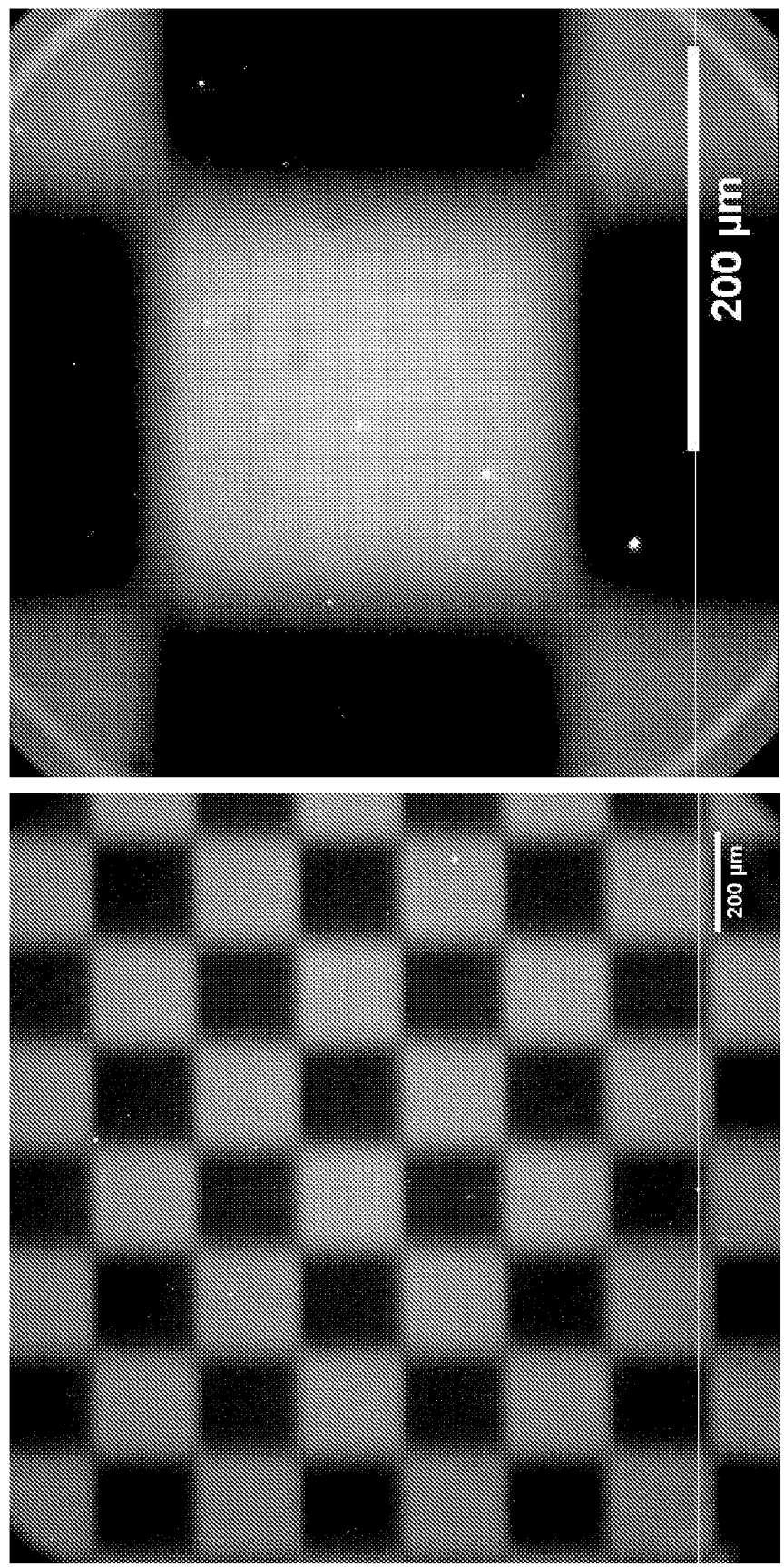
FIG. 24 illustrates zoomed in views of the surface in FIG. 23.
Figure 25:
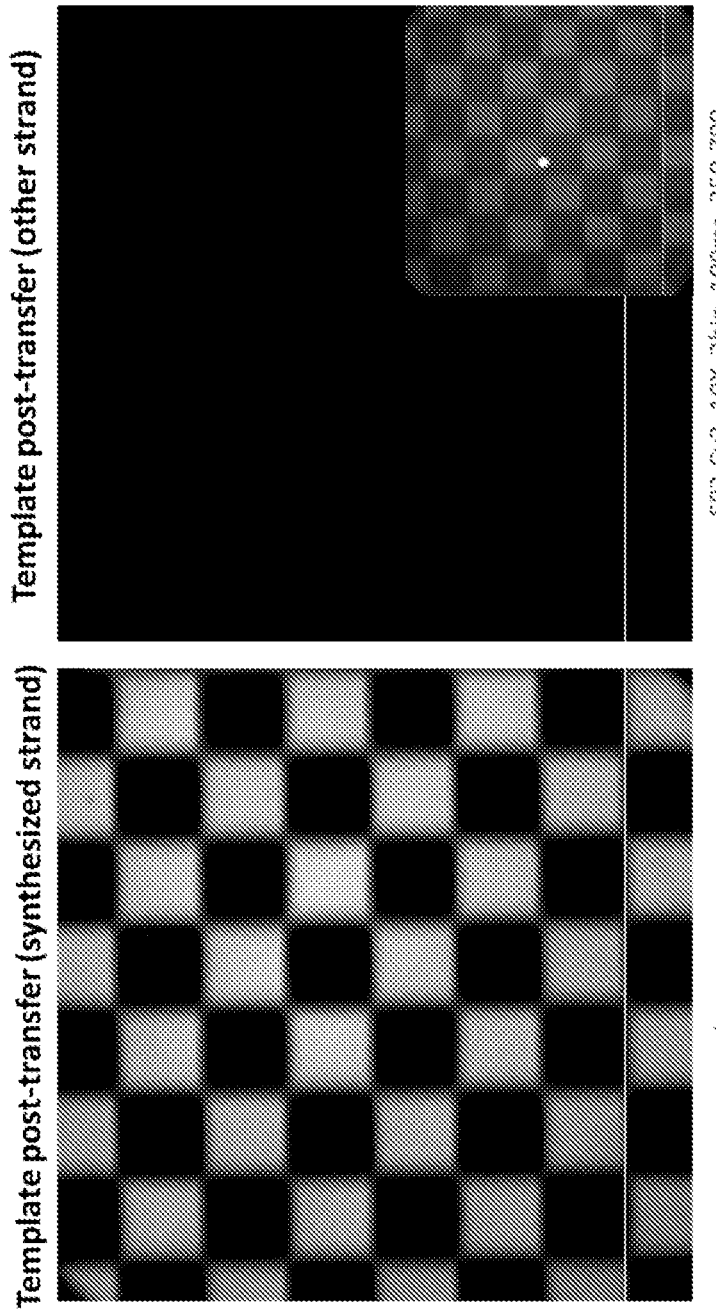
FIG. 25 illustrates a template after non-enzymatic gel transfer, with signal from the synthesized strand (left) and the other strand (right).
Figure 26:
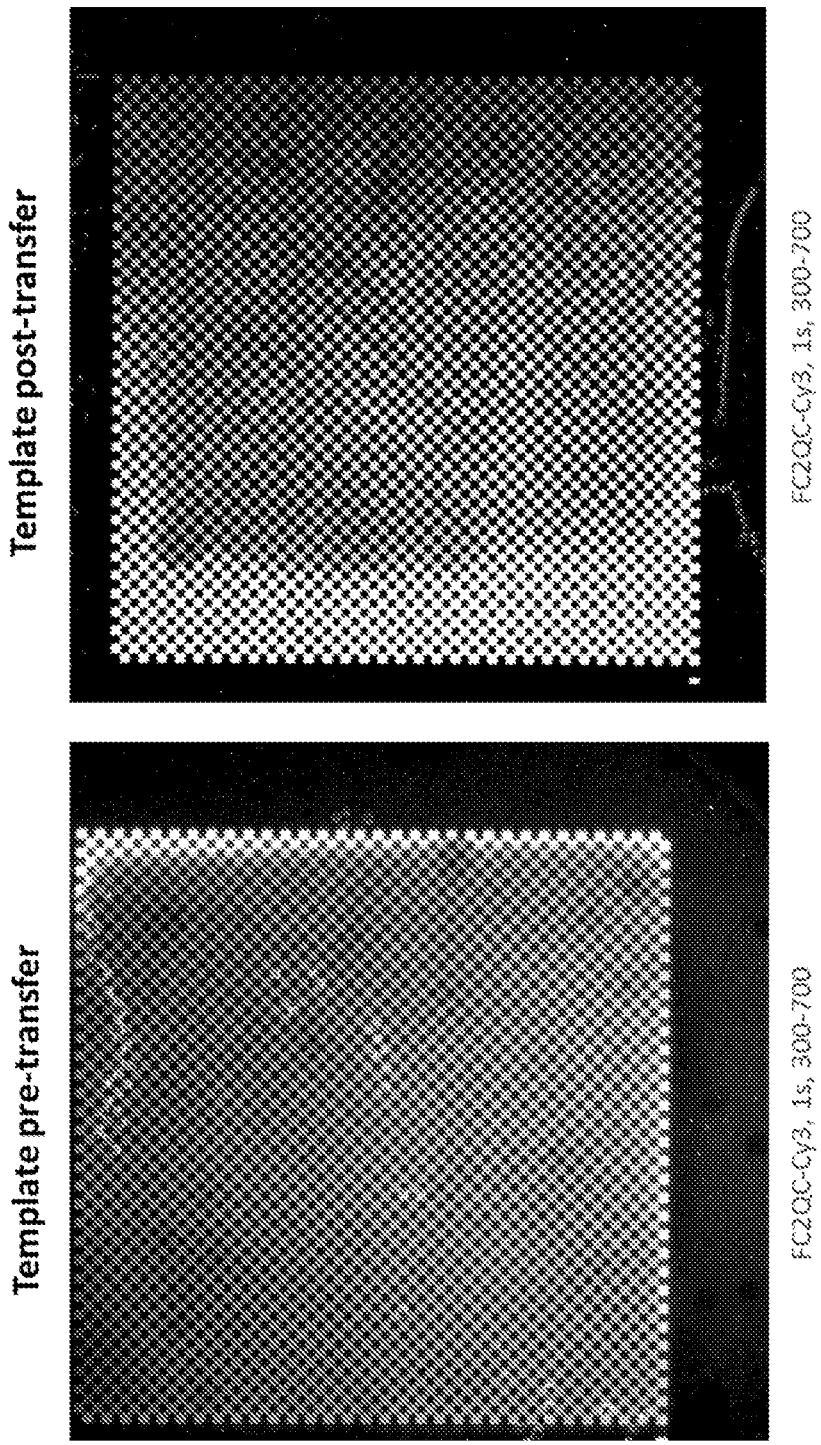
FIG. 26 illustrates a template pre- (left) and post- (right) non-enzymatic gel transfer.
Figure 27:
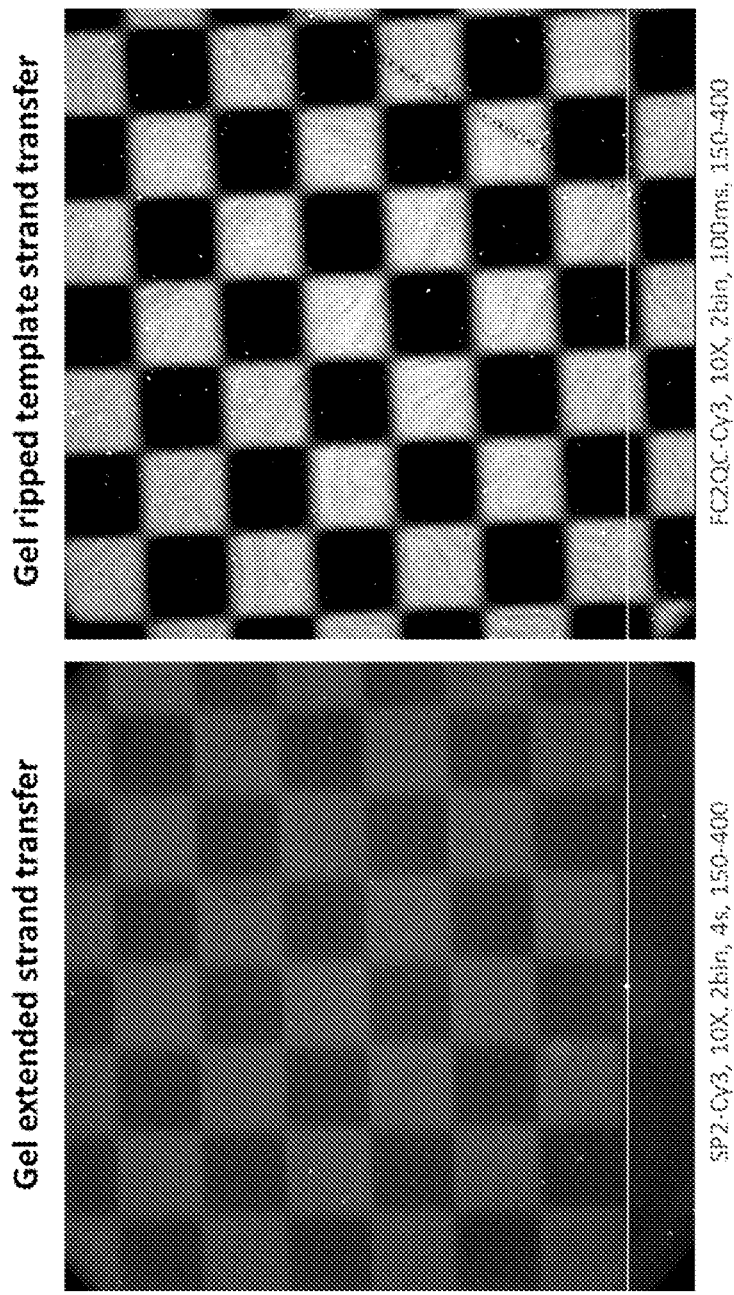
FIG. 27 illustrates copies from gel extended strand transfer (left) and gel ripped template strand transfer (right).

FIG. 23 shows a picture of a fluorescently labeled template array, with template molecules having the structure 5' CAGAAGACGGCATACGAGAT_GACTGGAGTTCA-GACGTGTGCTCTTCC_GTGTAGATCTCGGTG-GTCGCCGTA-3'T*-(HEG)$_2$-(substrate surface). Prior to imaging, the array was allowed to hybridize with 500 nM of QC FC2-Cy3 in 4×SSC buffer at 55° C. for 60 minutes. FIG. 24 shows zoomed in views of regions of the same template array. FIG. 25 shows the same template array as well as a recipient transfer array after a non-enzymatic transfer. The template nucleic acids were hybridized with Acr-FC1 (e.g., 5'Acrydite-TTTTTTTTTTAATGATACGGCGACCAC-CGAGAUCTACAC) primers and extended with Bst polymerase, then incorporated into a polymer gel on a recipient transfer array substrate and separated from the template array. The template array shows no appreciable decrease in signal post-transfer, while the transfer array shows a small signal under 10× exposure. FIG. 26 shows a side-by-side comparison of a template array pre- and post-transfer. As can be seen, the template array shows no appreciable decrease in signal post-transfer. FIG. 27 shows the receiving gel surface after non-enzymatic transfer (OIT). On the left, the desired strand obtained by hybridization to template, extension and subsequent immobilization is probed for on the gel surface. Alternatively, on the right, the template strand also was transferred to the receiving gel surface during OIT, presumably by physical detachment from the template array. Notably, the physical transfer of template strands is stronger than the immobilization of the extended primer. FIG. 28 shows a comparison in exposure settings between gel images, one with 10×2S 2 bin and one with 10×0.5s 1 bin.

In some cases, an oligo array with 5' to 3' orientation can be generated without enzymatic transfer. For example, the unbound end of the synthesized nucleic acid sequences on a template oligo array can comprise a linker sequence complementary to a sequence at or near the array-bound end of the oligo, allowing the oligo to circularize. The oligo can further comprise a restriction sequence at the same end. Digestion of the restriction sequence on circularized oligos serve to flip the full-length oligos containing the linker sequence and cut loose any partial-length oligo products on the array which lack the linker sequence. Many restriction enzymes and their associated restriction sites can be used, including but not limited to EcoRI, EcoRII, BamHI, HindIII, TaqI, NotI, HinFI, Sau3AI, PvuII, SmaI, HaeIII, HgaI, AluI, EcoRV, EcoP15I, KpnI, PstI, SacI, SalI, ScaI, SpeI, SphI, StuI, and XbaI.

Surfaces for Oligo Array Transfer Methods

The surfaces used for the transfer methods as provided herein (e.g., template surface and/or the recipient surface) can comprise a range of possible materials. In some cases, the surface comprises a polymer gel on a substrate, such as a polyacrylamide gel or a PDMS gel. In some cases, the surface comprises a gel without a substrate support. In some cases, the surface comprises a thin coating on a substrate, such as sub-200 nm coatings of polymer. In some cases, the surface comprises an uncoated substrate, such as glass or silicon.

The coatings and/or gels can have a range of thicknesses or widths. The gel or coating can have a thickness or width of about 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The gel or coating can have a thickness or width of less than 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The gel or coating can have a thickness or width of more than 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The gel or coating can have a thickness or width of at least 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The gel or coating can have a thickness or width of at most 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The gel or coating can have a thickness or width of between 0.0001 and 200 mm, between 0.01 and 20 mm, between 0.1 and 2 mm, or between 1 and 10 mm. The gel or coating can have a thickness or width of from about 0.0001 to about 200 mm, about 0.01 to about 20 mm, about 0.1 to about 2 mm, or about 1 to about 10 mm. In some cases, the gel or coatings comprises a width or thickness of about 10 microns.

Gels and coatings can additionally comprise components to modify their physicochemical properties, for example, hydrophobicity. For example, a polyacrylamide gel or coating can comprise modified acrylamide monomers in its polymer structure such as ethoxylated acrylamide monomers, phosphorylcholine acrylamide monomers, and/or betaine acrylamide monomers.

Gels and coatings can additionally comprise markers or reactive sites to allow incorporation of markers. Markers can comprise oligonucleotides. For example, 5'-acrydite-modified oligonucleotides can be added during the polymerization process of a polyacrylamide gel or coating. Reactive sites for incorporation of markers can comprise bromoacetyl sites, azides, sites compatible with azide-alkyne Huisgen cycloaddition, or other reactive sites. Markers can be incorporated into the polymer coatings in a controlled manner, with particular markers located at particular regions of the polymer coatings. Markers can be incorporated into the polymer coatings at random, whereby particular markers can be randomly distributed throughout the polymer coatings.

In some cases, a surface with a gel coating can be prepared as follows: glass slides are cleaned (e.g., with NanoStrip solution), rinsed (e.g. with DI water), and dried (e.g. with $N_2$); the glass slide surface is functionalized with acrylamide monomers; a silanation solution is prepared (e.g., 5% by volume (3-acrylamidopropyl)trimethoxysilane in ethanol and water); the glass slide is submerged in the silanation solution (e.g. for 5 hours at room temperature), rinsed (e.g., with DI water), and dried (e.g. with $N_2$); a 12% acrylamide gel mix is prepared (e.g., 5 mL $H_2O$, 1 mg gelatin, 600 mg acrylamide, 32 mg bis-acrylamide); a 6% acrylamide gel mix is prepared (e.g., 50 µL 12% acrylamide gel mix, 45 µL DI water, 5 µL 5'-acrydite modified oligonucleotide primers (1 mM, vortexed to mix); 6% acrylamide gel mix is activated (e.g., 1.3 µL of 5% ammonium persulfate and 1.3 µL of 5% TEMED are each added per 100 µL of gel mix and vortexed); gel mix is applied to a surface (e.g. silanized functionalized glass slide surface), evenly spread (e.g. by pressing with a cover slip or by spin coating), and allowed to polymerize (e.g., 20 minutes at room temperature).

Oligo Array Amplification and Regeneration

Figure 29:
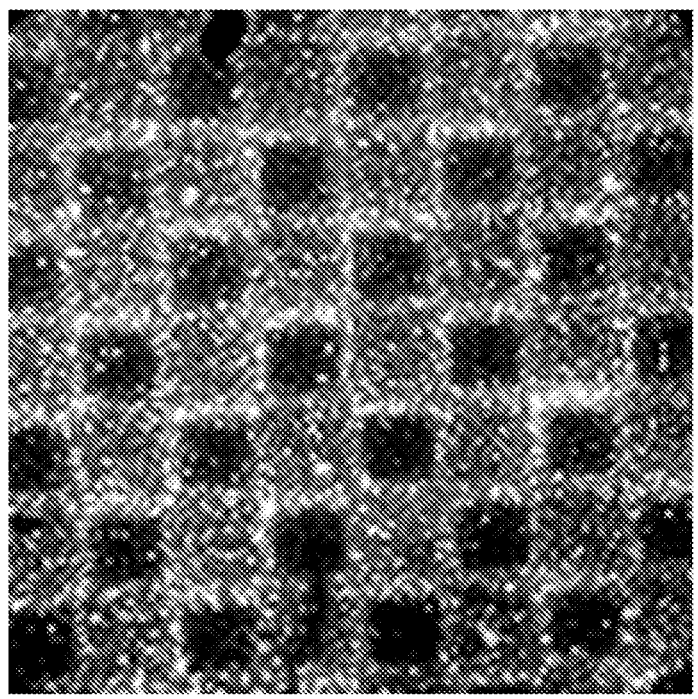
FIG. 29 illustrates cluster amplification after enzymatic transfer.

In some cases, the number of array components (e.g., nucleic acids, oligos) in each feature on an array (e.g., template and/or recipient) can be amplified or regenerated by a process referred to as amplification feature regeneration or AFR. AFR can be desirable for the template or recipient array if the array components on the template array have become depleted, for example from loss during transfers using array transfer methods as provided herein (e.g., ETS or OIT). Amplification can be desirable for the recipient array if the number of array components on the recipient array is low, for example due to a transfer from a template array with low density or a low number of array components. For example, FIG. 29 shows a template array used in enzymatic transfer and subsequently amplified with 50-70 cycles of amplification.

Amplification (e.g, by AFR) can be aided by the use of adaptor sequences on the template and/or recipient polymers (e.g., oligos). The template and/or recipient polymers (e.g., oligo) can comprise a desired final sequence in addition to one or more adaptor sequences. For example, a template and/or recipient oligo can comprise, in order, a 3' end with a first adaptor sequence, a 5' end with a second adaptor sequence, and a desired final sequence in the middle. The first and second adaptor sequences can be the same or can be different. In some cases, oligos in the same array spot comprise identical first and second adaptor sequences and final sequences, and oligos in different array spots comprise identical first and second adaptor sequences but different final sequences. Primers on a recipient array can be complementary to adaptor sequences, which can allow hybridization between the primers and the template polymers (e.g., oligos). Such hybridization can aid in amplification or regeneration of the array. Primers (e.g., oligo) coupled to an array can be generic e.g., universal or random primers, or target-specific primers.

Amplification (e.g, by AFR) of array (e.g., template or recipient) components can occur enzymatically. For example, if the array (e.g., template and/or recipient) components comprise oligos, amplification can occur by nucleic acid amplification reactions such as polymerase chain reaction (PCR), bridge amplification, bridge PCR, isothermal PCR, isothermal bridge amplification, isothermal bridge PCR, continuous flow PCR, recombinase polymerization amplification (RPA), or other reactions. The enzymes used can comprise a variety of enzymes, such as PolI, PolII, PolIII, Klenow, T4 DNA Pol, modified T7 DNA Pol, mutated modified T7 DNA Pol, TdT, Bst, Taq, Tth, Pfu, Pow, Vent, Pab or other polymerase enzymes; helicase; recombinase; or other enzymes.

The intensity or density of coupled polymers (e.g., nucleic acids, oligos) on an array (e.g., template and/or recipient) can be recovered by amplification. The intensity or density of coupled polymers (e.g., nucleic acids, oligos) on an array (e.g., template and/or recipient) can be increased beyond its initial value by amplification. Array (e.g., template and/or recipient) spots can grow during amplification. For example, bridge amplification or bridge PCR can lead to growth or walking of nucleic acid molecules by 50-100 nm during 28 cycles of amplification.

Array surfaces can comprise barriers to prevent amplification of array components beyond their individual feature borders. Barriers can comprise physical borders, reaction borders, or other borders. Borders can be fabricated by laser ablation of surface-coupled features (e.g. nucleic acids or other polymers). Borders can be fabricated by light-activated protective groups; for example, light-activated protective groups can be coupled to nucleic acids across an entire array, and then only desired areas can be deprotected.

Figure 30:
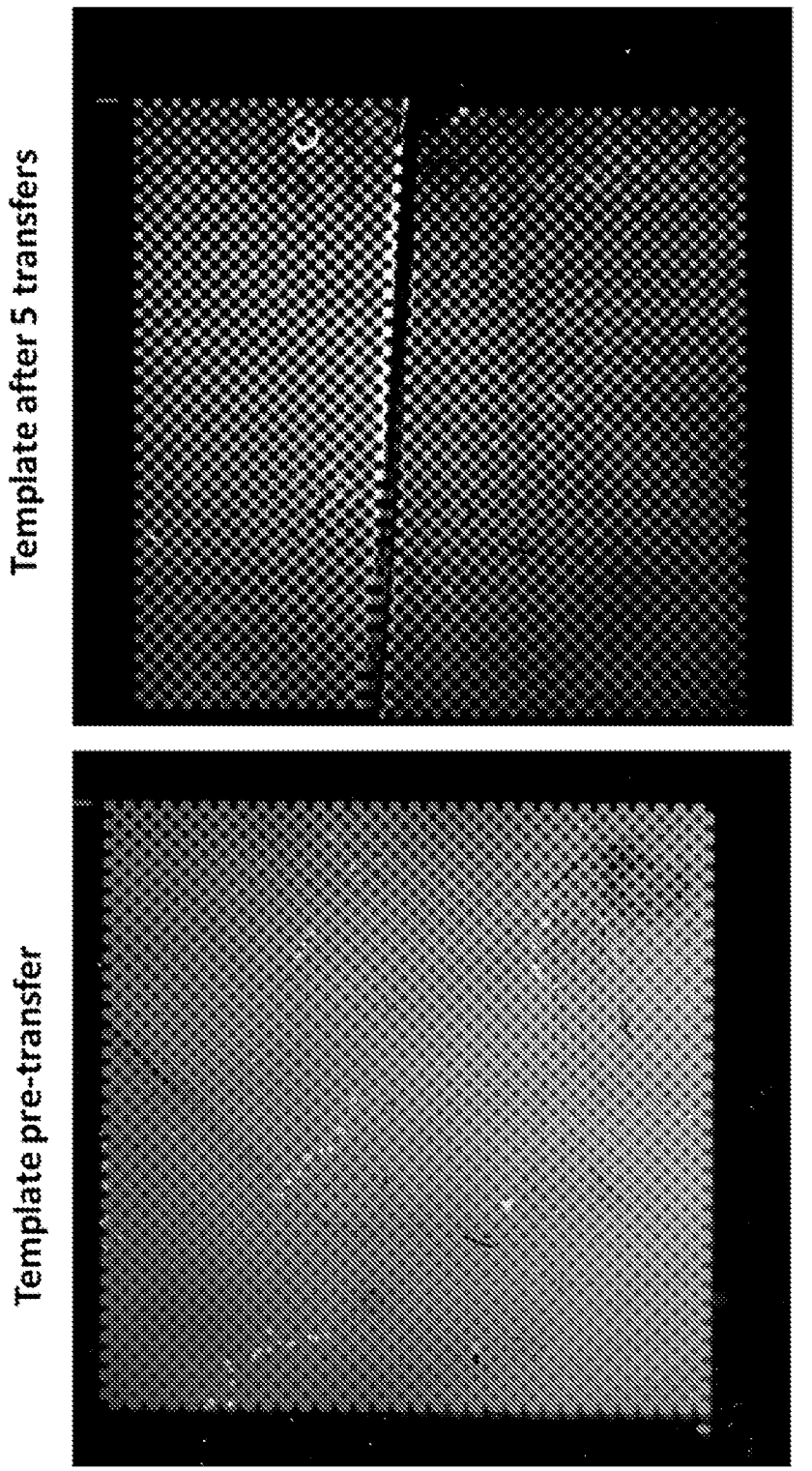
FIG. 30 illustrates a template array before (left) and after (right) 5 enzymatic transfers using the face-to-face enzymatic gel transfer process (e.g., enzymatic transfer by synthesis or ETS) described herein.

In some cases, a template oligo array can be generated by standard means, and a plurality of recipient transfer oligo arrays can be generated as complement or recipient arrays from the template. The recipient arrays can be generated using the face-to-face transfer process provided herein (e.g., ETS or OIT). This can result in reduced fabrication costs. In some instances, at least 5, 10, 20, 50, 100, 200, 500, 1,000, 2,000, 5,000, 10,000, 20,000, 100,000, 200,000, 500,000 complement arrays or recipient arrays can be generated from each template oligo array. For example, FIG. 30 shows images of a template array pre-transfer (left) and after five transfers (right) following face-to-face enzymatic gel transfer (i.e., ETS) as provided herein. Each of the complement arrays can result in oligonucleotide probes that are complementary to at least 50, 60, 70, 80, 90, 91, 92, 93, 94, 95, 96, 97, 98, 99, 99.5%, 99.9% or 100% of the template molecules on the template array.

Recipient transfer oligo arrays can comprise more enzymatically-favorable environments than arrays fabricated by standard means, thus allowing a wider range of reactions to be conducted on or near the array surface. For example, a recipient transfer array can comprise a polymer gel or coating, such as polyacrylamide, which can be more favorable to enzyme activity than an uncoated surface such as glass or silicon.

Recipient transfer oligo arrays can be fabricated comprising oligos with 3' ends up. This can provide reduced steric hindrance for hybridization. This can also provide oligos in a configuration useful for further extension, including sequencing by synthesis or genotyping (e.g. SNP detection).

Recipient transfer oligo arrays can be generated with very long oligos (e.g., greater than 50 base pairs). While synthesis of very long oligos can result in very few full-length oligo products, the compositions and methods described in this disclosure can generate recipient transfer arrays comprising mostly or only full-length oligonucleotides.

In some cases, the compositions and methods described in this disclosure can provide arrays with fine resolution, defined (i.e. not random) sequences in 5' to 3' orientation, and on an enzymatically compatible surface.

For enzymatic transfer methods, the immobilization of the oligos can reduce cross-contamination between array features. Furthermore, for a single-strand template the need to make a complementary strand before transfer can be eliminated.

Positional Sequencing of Nucleic Acids on an Array Surface

After an oligo array or chip is synthesized (and/or transferred) using methods as provided herein, a sample comprising a nucleic acid ("target polynucleotide") can be stretched and immobilized on the surface of the oligo array as outlined in FIGS. 1 and 2 and depicted in FIG. 3. The sample comprising the nucleic acid can be any sample as provided herein. The nucleic acid can be any nucleic acid as provided herein. In some cases, the nucleic acid is DNA. In some cases, the DNA is genomic DNA. The genomic DNA can be a chromosome or fragment of a chromosome. Oligo arrays fabricated using the methods provided herein can be used for determining sequences of polynucleotides or nucleic acid molecules such as RNA, DNA, chromosomes, and fragments thereof. Such polynucleotides are referred to herein as template or target polynucleotides. In some cases, target polynucleotides are stretched on an oligo array generated using the methods provided herein. The oligos on the array can comprise positional barcodes as described herein. The oligo array can be a template or recipient array. In some cases, prior to stretching a target polynucleotide on the oligo array (e.g., template or recipient array), is processed.

Target Polynucleotide Processing

In some cases, processing a target polynucleotide prior to stretching on an oligo array as provided herein involves isolating or extracting the target polynucleotide from a sample. The sample can be any sample as provided herein. Any of the methods for extracting Mb long DNA known in the art can be used, such as, for example, the method described in Zhang, M. et al. Preparation of megabase-sized DNA from a variety of organisms using the nuclei method for advanced genomics research. Nature protocols 7, 467-478, (2012), the disclosure of which is incorporated herein by reference in its entirety. In one example, the BioRad Mammalian Genomic DNA Plug Kit can be used. Briefly, the plug is washed, the agarose melted and subsequently digested with beta-agarase. Once isolated, a target polynucleotide to be used in the methods provided herein can be further processed as described below.

Figure 31:
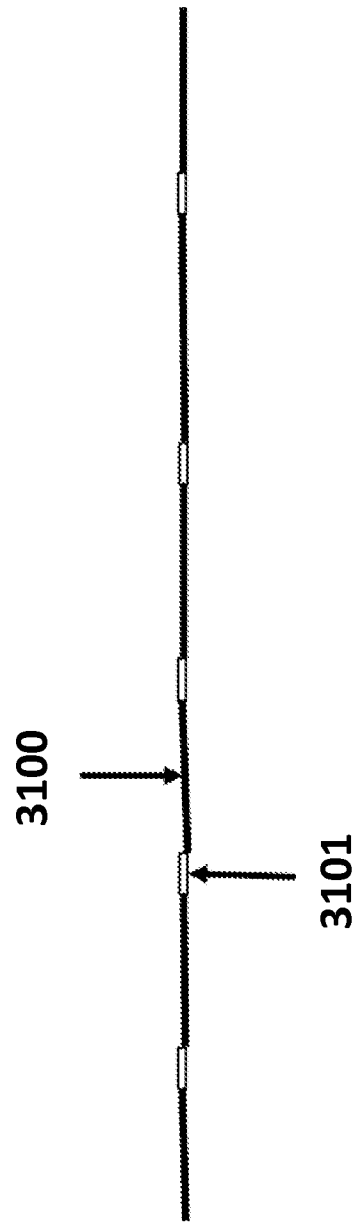
FIG. 31 illustrates a schematic of adding extendable sequences to long nucleic acid via transposon insertion.
Figure 32:
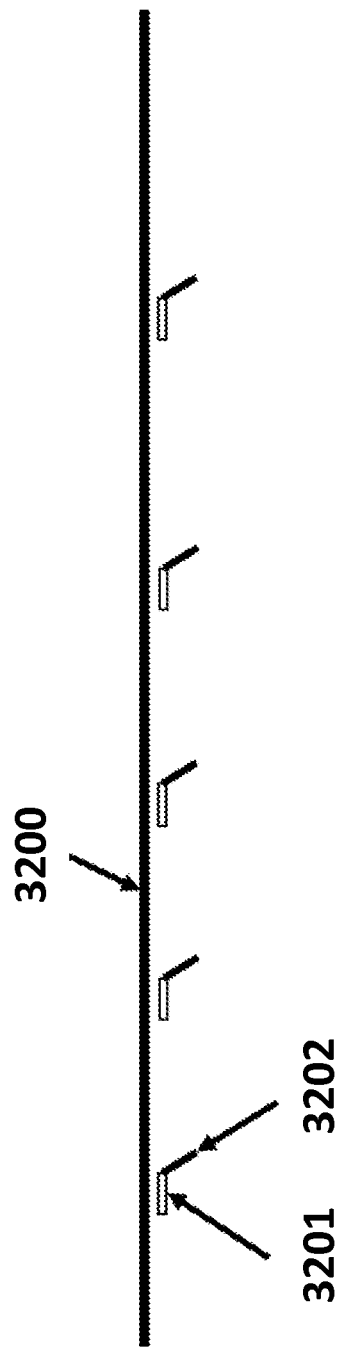
FIG. 32 illustrates a schematic of adding extendable sequences to long nucleic acid with random primers.

In some cases, a target polynucleotide isolated from a sample is further processed such that primer (e.g., oligo) binding sites are added to the target polynucleotide. For example, as shown in FIG. 31 and FIG. 32, universal primer binding sites can be incorporated into the template nucleic acid molecule 3102, 3202. Primer binding sites are regions of nucleic acid that can comprise sequence complementary to defined sequence in a primer. The primer comprising the defined sequence can be an oligo bound to a template or recipient array as provided herein. The defined sequence can be adaptor sequence. The defined sequence can be universal sequence. Primer binding sites in a template nucleic acid can be used to couple or bind the template nucleic acid comprising the primer binding sites to primers comprising complementary sequence to the primer binding sites. The defined sequence (e.g., adaptor or universal) of an array-bound primer can be capable of coupling to the template nucleic acid comprising complementary primer binding sites directly, such as by hybridizing to the primer binding site sequence within the template nucleic acid. The defined sequence (e.g., adaptor or universal) of an array-bound primer can be capable of coupling to the template nucleic acid indirectly, such as by hybridizing to a primer binding site sequence complementary to the defined sequence in a free primer while the free primer can be capable of hybridizing to the template nucleic acid. In some instances, the primers hybridize at defined intervals. In other instances, the primers hybridize at random intervals. Primers (e.g., array or non-array bound) are preferably hybridized to target polynucleotides at intervals along the target polynucleotides of at least 50, 100, 200, 300, 400, 500, 1,000, 1,200, 1,400, 1,600, 1,800, or 2,000 base pairs. The primers (e.g., array or non-array bound) can hybridize to random sequences on a target polynucleotide or primer binding sites on a target polynucleotide introduced using the methods provided herein. Primer binding sites can comprise at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. Primer binding sites can comprise at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases.

In some cases, primer (e.g., oligo) binding sites are added to a target polynucleotide using a nicking enzyme followed by ligation of the primer (e.g., oligo) binding sites. The method can comprise enzymatic nicking of the target polynucleotide (e.g., long DNA molecules) using Nt.CviPII, or any other suitable nicking enzyme, which cleaves only one strand at a CCD site. Following nicking of the target polynucleotide, the nicked ends of the target polynucleotides can be treated with a phosphatase (e.g., Next Shrimp Alkaline Phosphatase (rSAP)) to remove 5' phosphates and prevent ligation of the nicked ends of the target polynucleotides. In some cases, nicking of a target polynucleotide and removal of 5' phosphates is performed in a single reaction. For example, treatment of a target polynucleotide with Nt.CviPII and rSAP can be performed in a single reaction buffer (i.e., NEBuffer 2.1, New England Biolabs). Subsequently, the enzymes can be heat inactivated, followed by ligation of a primer binding site to the 3' ends of the target polynucleotide within the nick. Finally, the processed target polynucleotide with appended primer binding sites can be diluted in 0.5M pH 5.5 buffer and poured into stretching reservoir to prepare it for combing (stretching) on an oligo array fabricated using the methods provided herein.

In some cases, universal primer binding sites can be incorporated into the target polynucleotides (also referred to as template nucleic acid molecule) via transposon insertion, for example as outlined in FIG. 1, 102 and shown in FIG. 31. Preferably, such primer-binding sites are inserted on average every at least 50, 100, 200, 300, 400, 500, 1,000, 1,200, 1,400, 1,600, 1,800, or 2,000 base pairs along the length of a target polynucleotide. Transposons can be integrated into a target polynucleotide, such as DNA, at various intervals. Transposons can be inserted at an average of about 100, 200, 500, 1000, 1500, or 2000 base pairs. FIG. 31, shows primer binding sites 3101 added to the target polynucleotide 3100 by transposon insertion. The primer binding site can comprise defined sequence. The defined sequence can be universal, adaptor, and/or barcode sequence. The primer binding site can comprise universal, adaptor, and/or barcode sequence. Methods for integration of transposons are described, for example, in U.S. Patent Application Publication No. US 2012/0208724 A1, the disclosure of which is herein incorporated by reference in its entirety.

Figure 36:
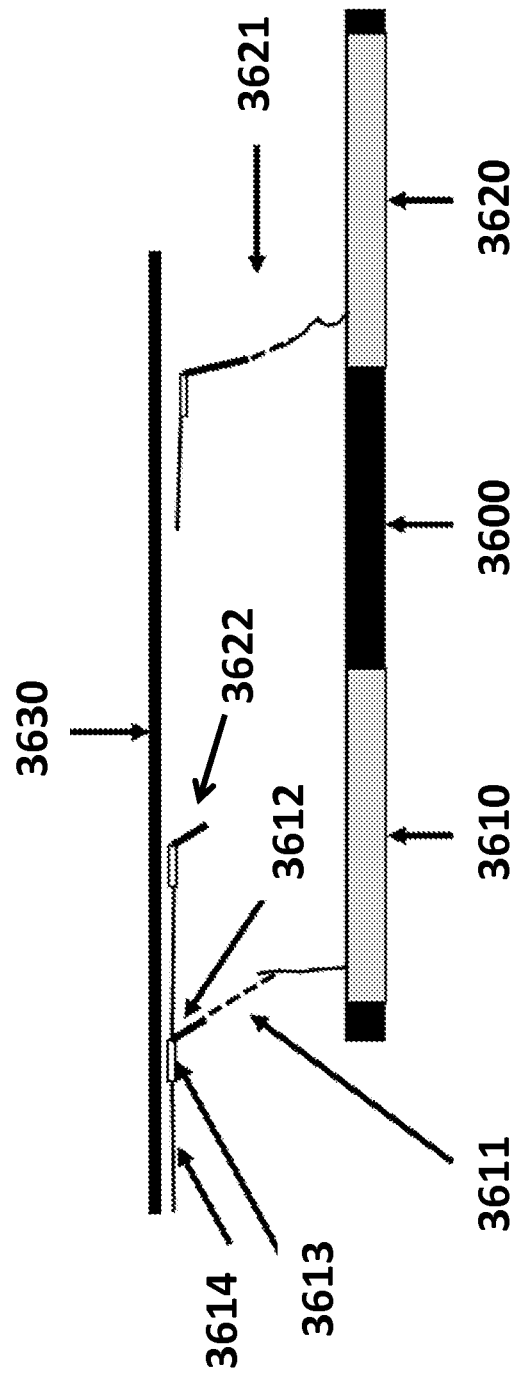
FIG. 36 illustrates a schematic of adding extendable sequences to long nucleic acid with random primers using substrate features.

In some cases, universal primer binding sites can be incorporated into target polynucleotides via hybridization with non-substrate or array-bound primers, for example as outlined in FIG. 2, 202. The non-substrate-bound primers can be referred to as free primers. The non-substrate bound primers can be in solution. For example, as shown in FIG. 32, a template nucleic acid (target polynucleotide) 3200 can be contacted with free primers that comprise a random sequence 3201 (e.g. random pentamer, random hexamer, or random nonomer) that hybridizes to the template nucleic acid molecule 3200, and a primer binding site sequence 3202 that does not hybridize to the template nucleic acid molecule 3200. As described herein, the primer binding site can comprise defined sequence. The defined sequence can be universal, adaptor, and/or barcode sequence. The primer binding site can comprise universal, adaptor, and/or barcode sequence. A random sequence in a free primer used for introducing primer binding sites into a target polynucleotide as provided herein can be at least 5, 6, 7, 8, 9, 10, 11, 12, 13, 14, or 15 base pairs in length. In some cases, the random sequences can be at most 5, 6, 7, 8, 9, 10, 11, 12, 13, 14, or 15 base pairs in length. In some cases, the random sequences can be 5, 6, 7, 8, 9, 10, 11, 12, 13, 14, or 15 base pairs in length. In some cases, the random sequences can be more than 5, 6, 7, 8, 9, 10, 11, 12, 13, 14, or 15 base pairs in length. In some cases, the random sequences can be less than 5, 6, 7, 8, 9, 10, 11, 12, 13, 14, or 15 base pairs in length. Array-bound primers can comprise defined sequence (e.g., adaptor, universal, and/or barcode sequence) that is complementary to and can hybridize to the primer binding site sequence of the free primers via binding between the complementary sequences, thereby indirectly coupling the template nucleic acid to an oligo array (template or recipient array). An example of this is shown in FIG. 36 and described herein. The oligo array can be generated using any of the methods provided herein.

In some cases, a target polynucleotide can be nicked, and biotinylated nucleotides can be added to the resulting nucleic acid fragments by primer extension, thereby producing nucleic acid fragments with biotin at or near one end. Alternatively, random primers (e.g. random hexamers or random nonomers) labeled with biotin are used to perform extension with a target polynucleotide, thereby producing nucleic acid extension products with biotin at or near one end. In any case, primer extension can be conducted by suitable enzymes, including polymerases such as PolI, PolII, PolIII, Klenow, T4 DNA Pol, modified T7 DNA Pol, mutated modified T7 DNA Pol, TdT, Bst, Taq, Tth, Pfu, Pow, Vent, Pab, Phusion and Phi-29. For example, reactions can be conducted using Bst polymerase by incubating the target polynucleotide and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20). DNA molecules comprising biotin, such as DNA fragments or DNA extension products prepared as described above, can then be stretched on a stretching substrate along with their template DNA molecules.

In some cases, a target polynucleotide can be nicked, and reversibly terminating nucleotides can be added to the 3' end of the resulting DNA fragments to prevent or reduce ligation. In some cases, random primers (e.g. random hexamers or random nonomers) are used to perform extension in the presence of nucleotides with a target polynucleotide template, thereby producing DNA extension products. As described herein, the random primers can be labeled with biotin at or near one end such that extension produces DNA extension products with biotin at or near one end. The nucleotides used for the extension can be native nucleotides mixed with a small percentage of terminator nucleotides, thereby producing some extension products with a terminating nucleotide at the 3' end of the resulting DNA extension products. Such DNA extension products can be less likely to be ligated. Primer extension can be conducted by suitable enzymes, including polymerases such as PolI, PolII, PolIII, Klenow, T4 DNA Pol, modified T7 DNA Pol, mutated modified T7 DNA Pol, TdT, Bst, Taq, Tth, Pfu, Pow, Vent, Pab, and Phi-29. For example, reactions can be conducted using Bst polymerase by incubating the target polynucleotide and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20). The dNTPs can have a small percentage of terminator nucleotides. DNA molecules, such as DNA fragments or DNA extension products prepared as described above, can then be stretched on a stretching substrate along with their target polynucleotide.

Target Polynucleotide Stretching

In some cases, a target polynucleotide for use in the methods provided herein is stretched. The target polynucleotide can be DNA. Stretching can be performed by various methods, including but not limited to molecular combing, transfer printing, molecular threading, nanochannels, electric force, magnetic force, optical force, and hydrodynamic force. Stretching can be performed by a combination of methods. For example the use of molecular combing and nanochannels. DNA stretching can be a process through which DNA in a solution ("free DNA") can be placed in a reservoir, and a hydrophobic-coated slide can be dipped into the DNA solution and retracted. While the physics of the process may not be fully understood, the DNA ends can interact with the surface of the slide through hydrophobic interactions, and the process of retracting the slide can produce a receding meniscus which can serve to pull the DNA across a surface in a linear fashion (see FIGS. 31 and 34 for examples of labeled DNA stretched on a surface). DNA stretching can be a highly parallel process that can produce high-density packed DNA molecules stretched on a surface or substrate. One of skill in the art can appreciate that DNA stretching can be performed on a variety of surfaces, and specific conditions for stretching on specific surfaces can be optimized using methods known in the art. The variety of surfaces or substrates can be glass, silicon, and/or polymers or polymer-coated surfaces. Stretching substrates can comprise features, such as microchannels, nanochannels, microposts, or nanoposts. The stretching substrate can be the same as the primer array or can be a separate substrate. The DNA molecules can range in size from several hundred kb to more than 1 Mb. Immobilization of intact, several kb to Mbase length target polynucleotides (e.g., DNA molecules) by stretching can provide the ability to resolve sequence in complex repetitive regions of a genome, and can further reduce the sequencing costs associated with WGS. Stretching can provide improved access for hybridization to the template nucleic acid molecule. Stretching can increase the linearity of the template nucleic acid molecule. Stretching nucleic acids can increase the resolution or distance between regions of the nucleic acid. Stretching can increase the length of DNA to 1.5 times the crystallographic length of DNA. Once a target polynucleotide (e.g., DNA) has been stretched and bound to a solid surface, it can be probed to create scaffolds for assembling the short NGS reads as described herein. For example, as shown in FIG. 1 and FIG. 2, in preparation for positional tagging with barcodes and subsequent applications (e.g., NGS), target polynucleotides (also referred to as template nucleic acids) processed as provided herein can be stretched or elongated 103, 203. The template nucleic acids can be stretched on an oligo array (e.g., template or recipient oligo arrays).

Figure 33:
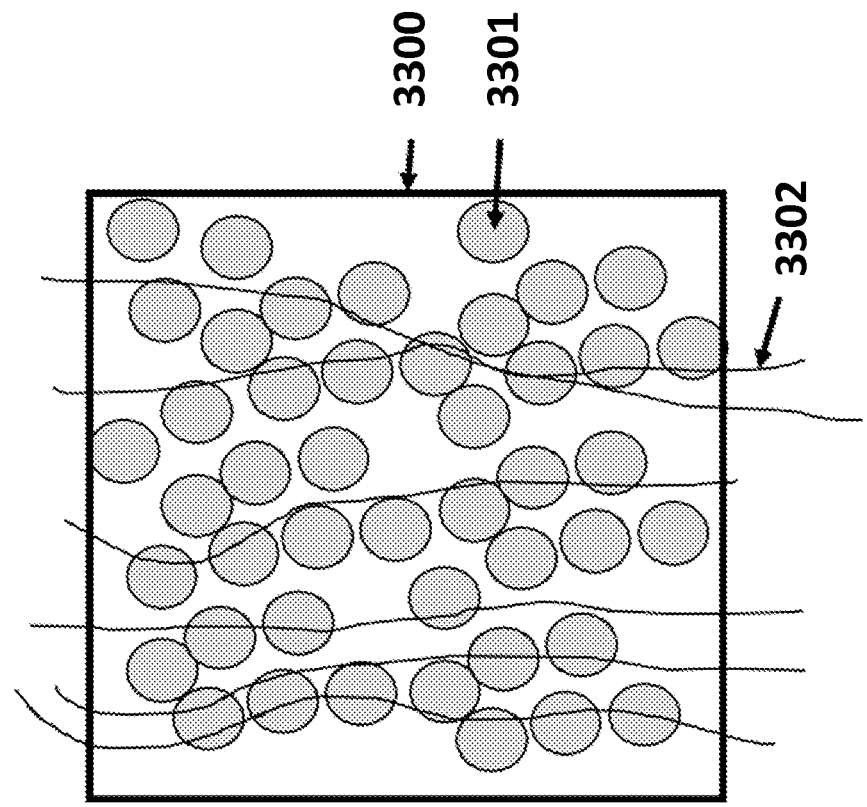
FIG. 33 illustrates a schematic of nucleic acid strands on a substrate with spatially-encoded clusters.
Figure 34:
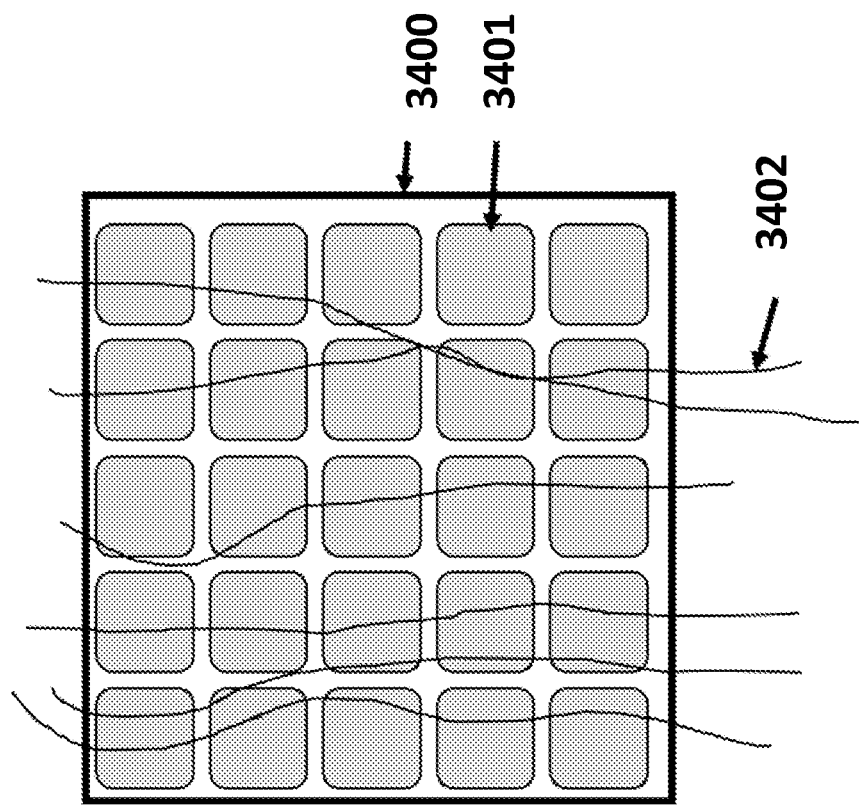
FIG. 34 illustrates a schematic of nucleic acid strands on a substrate with a spatially-encoded array.

While stretching can occur in solution or on a substrate, the stretched target polynucleotide can be eventually laid upon or can be positioned in an elongated fashion upon a substrate. For example, FIG. 33 shows stretched nucleic acid molecules 3302 on an array substrate 3300 comprising cluster array spots 3301. In another example, FIG. 34 shows stretched nucleic acid molecules 3402 on an array substrate 3400 comprising a two-dimensional array of array spots 3401. The array substrates can be template and/or recipient oligo arrays as described herein.

The stretching substrate can comprise a surface coating or functionalization. The surface coating or functionalization can be hydrophobic or hydrophilic. The stretching substrate can be an amine derivatized glass slides with a poly)maleic anhydride)-based comb-copolymer). The surface coating can comprise a polymer coating, such as polyacrylamide. The surface coating can comprise a gel, such as a polyacrylamide gel. The surface coating can comprise metal, such as patterned electrodes or circuitry. The surface coating or functionalization can comprise a binding agent, such as streptavidin, avidin, antibodies, antibody fragments, or aptamers. The surface coating or functionalization can comprise primers, e.g., for elongating fragments of the stretched nucleic acid. The surface coating or functionalization can comprise multiple elements, for example a polymer or gel coating and a binding agent, or a polymer gel coating and primers. The stretching substrate can comprise a primer array. Primer arrays are further discussed elsewhere in this disclosure.

In some cases, the target polynucleotides are subjected to molecular combing (also known as DNA combing or chromosome combing). The molecular combing method can be one such as the one described in Gueroui, Z., Place, C., Freyssingeas, E. & Berge, B. Observation by fluorescence microscopy of transcription on single combed DNA. Proceedings of the National Academy of Sciences of the United States of America 99, 6005-6010, (2002), or Bensimon, A. et al. Alignment and sensitive detection of DNA by a moving interface. Science 265, 2096-2098, (1994), or Michalet, X. et al. Dynamic molecular combing: stretching the whole human genome for high-resolution studies. Science 277, 1518-1523, (1997), or Allemand et al., 1997, *Biophysical Journal* 73:2064-2070, the disclosure of each of which is herein incorporated by reference in its entirety. Nucleic acid (e.g., DNA) strand ends can be bonded to the substrate, for example to ionizable groups on a substrate (e.g., silanized glass plate). Bonding of nucleic acids (e.g., DNA molecules) to the substrate can be accomplished at a specific pH, such as a pH below the pKa of the ionizable group. Nucleic acid molecules (e.g., DNA molecules) in solution can be combed and stretched by the retracting meniscus of the solution moving across a substrate. The nucleic acid (e.g., DNA) can be stretched by the retracting meniscus pulling against the tethered molecular end. The extent of stretching can be independent of the length of the nucleic acid (e.g., DNA). In some cases, the stretched nucleic acid (e.g., DNA) comprises about 2 kb per 1 μm.

In some cases, stretching of a target polynucleotide as provided herein is by by transfer printing. The transfer printing method can be one such as the one described in Zhang et al., 2005, *Langmuir* 21:4180-4184, the disclosure of which is hereby incorporated by reference in its entirety. Stretched nucleic acids can be prepared and aligned on a stamp, such as a PDMS stamp, by stretching with molecular combing. Nucleic acids stretched on the stamp can be anchored or bonded to the surface, for example by amino-terminated surface modification. Contact or transfer printing can be used to transfer aligned nucleic acids from the stamp to a surface. In some cases, the meniscus speed can influence the nucleic acid density on the surface.

In some cases, stretching of a target polynucleotide as provided herein is by by molecular threading. The molecular threading method can be one such as the one described in Payne et al., 2013, *PLoS ONE* 8:e69058 the disclosure of which is hereby incorporated by reference in its entirety. A droplet of nucleic acid molecules (e.g., DNA molecules) in solution can be positioned near a surface. A probe, such as a PMMA-treated glass needle, can be used to grab individual nucleic acid molecules (e.g., DNA molecules) in the solution. The probe can then be pulled from the solution, stretching the associated nucleic acid molecule (e.g., DNA molecule). The stretched nucleic acid molecule (e.g., DNA molecule) can then be deposited on a surface. In some cases, stretched nucleic acid molecules (e.g., DNA molecules) can be placed less than or equal to about 100 nm apart.

In some cases, stretching of a target polynucleotide as provided herein is performed by use of nanochannels. The stretching through the use of nanochannel can be such as described in Reisner et al., 2012, *Rep. Prog. Phys.*, 75(10): 106601 or in U.S. Pat. No. 7,670,770 the disclosures of which are each hereby incorporated by reference in their entireties. Nanochannels can be about 200, 190, 180, 170, 160, 150, 140, 130, 120, 110, 100, 90, 80, 70, 60, 50, 40, 30, 20, or 10 nm in width, height, diameter, or hydrodynamic radius. Nanochannels can be formed in materials including polymer, glass, and silicon. Nucleic acid molecules (e.g., DNA molecules) can stretch out when confined in nanochannels, due to self-avoidance interactions. Extension or stretching of nucleic acids (e.g., DNA) in nanochannels can depend on the ionic strength of the nucleic acid (e.g., DNA) solution.

In some cases, stretching of a target polynucleotide as provided herein is performed by use of nanostructures. The stretching through the use of nanostructures can be such as described in U.S. Pat. No. RE42315, the disclosure of which is hereby incorporated by reference in its entirety. Nanostructures on a substrate can comprise nanotroughs, and the substrate can have a lipid bilayer suspended on it. Nucleic acid molecules (e.g., DNA molecules) can be driven through the membrane into the troughs and stretched.

In some cases, stretching of a target polynucleotide as provided herein is performed by magnetic force (such as magnetic tweezers). The magnetic force method can be one such as the one described in Haber and Wirtz, 2000, *Rev. Sci. Instrum.* 71:4561, the disclosure of which is hereby incorporated by reference in its entirety. Nucleic acid molecules (e.g., DNA molecules) can be linked to a magnetic particle or bead, which can then be manipulated with an applied magnetic field. Applied magnetic force can be used to stretch the nucleic acid molecule (e.g., DNA molecule), for example while one end of the molecule is linked to a magnetic particle and the other end of the molecule is linked or tethered to a substrate.

In some cases, stretching of a target polynucleotide as provided herein is performed by optical force (such as optical tweezers). The optical force method can be one such as the one described in Wang et al., 1997, *Biophysical Journal*, 72(3):1335-1346, the disclosure of which is hereby incorporated by reference in its entirety. Nucleic acid molecules (e.g., DNA molecules) can be linked to a particle or bead, which can then be manipulated with an optical trap. The optical trapping force can be used to stretch the nucleic acid molecule (e.g., DNA molecule), for example while one end of the molecule is linked to a trapped particle and the other end of the molecule is linked or tethered to a substrate.

In some cases, stretching of a target polynucleotide as provided herein is performed by electrical fields. The electrical fields method can be one such as the one described in Ferree and Blanch, 2003, *Biophysical Journal*, 85(4):2539-2546, the disclosure of which is hereby incorporated by reference in its entirety. Nucleic acid molecules (e.g., DNA molecules) can be tethered to a substrate, such as by biotin-streptavidin binding or other methods. An applied electric field can then be used to generate a force to stretch the molecules.

In some cases, stretching of a target polynucleotide as provided herein is performed by hydrodynamic force. The hydrodynamic method can be one such as the one described in Kim et al., 2007, *Nature Methods*, 4:397-399, the disclosure of which is hereby incorporated by reference in its entirety. Target polynucleotides can be tethered to a substrate, such as by biotin-streptavidin binding or other methods. Fluid flow around the target polynucleotides can provide force to stretch the molecules.

In some cases, target polynucleotides can be stretched on a stretching substrate and then contacted with a primer array (e.g., template and/or recipient oligo array). Alternatively, target polynucleotides can be stretched directly on a primer array (e.g., template and/or recipient oligo array).

In some cases, molecular combing is used to stretch a target polynucleotide on an oligo array (e.g., template and/or recipient oligo array) as provided herein. The target polynucleotide can be any template nucleic acid from any template nucleic acid source as provided herein. There can be a number of variables that influence DNA binding to an array. Two critical variables can be the slide surface characteristics and the chemical composition of the buffer. One of skill in the art would appreciate that may be desirable to vary difference parameters such as surface properties to optimize molecularc combing on an oligo chip or array. In some cases, vinyl-functionalized slides are used for molecular combing. Surface characteristics can be a factor influencing DNA combing as described in Allemand, J. F., Bensimon, D., Jullien, L., Bensimon, A. & Croquette, V. pH-dependent specific binding and combing of DNA. *Biophys J* 73, 2064-2070, (1997), the disclosure of which is incorporated herein by reference in its entirety. In some cases, molecular combing of target polynucleotides is performed on amino-silane and vinyl-silane coated glass slides. In some cases, face-to-face enzymatic gel transfer of a template oligo array to a recipient array as described herein is performed on functionalized PDMS that has been treated with vinyl- or amino-silanes. In some cases, face-to-face enzymatic gel transfer of a template oligo array to a recipient array as described herein is performed on functionalized acrylamide surfaces that have been treated with vinyl- or amino-silanes. Acrylamide can be functionized using various modified monomers such as described in Seiffert, S. & Oppermann, W. Amine-Functionalized Polyacrylamide for Labeling and Crosslinking Purposes. *Macromolecular Chemistry and Physics* 208, 1744-1752, (2007), the disclosure of which is incorporated herein by reference in its entirety.

Additionally, one of skill in the art would appreciate that it can be desirable to optimize the surface treatments for molecular combing as provided herein and thus allow for enzymes to access a target polynucleotide. In some cases, the stretching constant of the target polynucleotide is reduced on a surface in order to obtain higher polymerase efficiency. The surface can be a functionalized PDMS that has been treated with vinyl- or amino-silanes. The surface can be a functionalized acrylamide surface that has been treated with vinyl- or amino-silanes.

Immobilization

This disclosure provides methods and compositions for immobilization of nucleic acids on a substrate. Optionally, immobilization can be used to help separate extension or amplification products from the template nucleic acid ("target polynucleotide"). In some cases, a target polynucleotide is immobilized to an immobilization substrate.

Many different materials are suitable for use as the immobilization substrate. The immobilization substrate can comprise glass, silicon, polymer (e.g. polyacrylamide, PMMA), or metal. The immobilization substrate can comprise physical features, such as microchannels or nanochannels.

The immobilization substrate can comprise a surface coating or functionalization. The surface coating or functionalization can be hydrophobic or hydrophilic. The surface coating can comprise a polymer coating, such as polyacrylamide. The surface coating can comprise a gel, such as a polyacrylamide gel. The surface coating can comprise metal, such as patterned electrodes or circuitry. The surface coating or functionalization can comprise a binding agent, such as streptavidin, avidin, antibodies, antibody fragments, or aptamers. The surface coating or functionalization can comprise multiple elements, for example a polymer or gel coating and a binding agent.

In some cases, a target polynucleotide can be nicked, and biotinylated nucleotides can be added to the resulting nucleic acid fragments by primer extension, thereby producing nucleic acid fragments with biotin at or near one end. Alternatively, random primers (e.g. random hexamers or random nonomers) labeled with biotin are used to perform extension with a nucleic acid molecule template, thereby producing nucleic acid extension products with biotin at or near one end. In any case, primer extension can be conducted by suitable enzymes, including polymerases such as PolI, PolII, PolIII, Klenow, T4 DNA Pol, modified T7 DNA Pol, mutated modified T7 DNA Pol, TdT, Bst, Taq, Tth, Pfu, Pow, Vent, Pab, and Phi-29. For example, reactions can be conducted using Bst polymerase by incubating the template nucleic acid and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20). In some cases, a target polynucleotide is a DNA molecule comprising biotin. The DNA molecule comprising biotin, such as DNA fragments or DNA extension products prepared as described above, can then be stretched on a stretching substrate along with their template DNA molecules. The DNA on the stretching substrate can then be contacted with an immobilization substrate. The immobilization substrate can comprise a binding agent, such as avidin or streptavidin. The biotin can be used to bind the DNA molecules to the immobilization substrate via avidin or streptavidin binding. The stretching substrate and the immobilization substrate can be separated with the use of heat or other denaturing methods. The immobilization substrate can then be contacted with a primer substrate (e.g., oligo array as provided herein) comprising positionally-encoded primers (oligos) as described in this disclosure. Primers can be ligated to the DNA fragments or DNA extension products on the immobilization substrate to encode positional information with barcodes, or to add adaptors useful for sequencing library construction.

In some cases, a DNA molecule can be nicked, and reversibly terminating nucleotides can be added to the 3' end of the resulting DNA fragments to prevent or reduce ligation. In some cases, random primers (e.g. random hexamers or random nonomers) are used to perform extension in the presence of nucleotides with a target polynucleotide template, thereby producing DNA extension products. As described herein, the random primers can be labeled with biotin at or near one end such that extension produces DNA extension products with biotin at or near one end. The nucleotides used for the extension can be native nucleotides mixed with a small percentage of terminator nucleotides, thereby producing some extension products with a terminating nucleotide at the 3' end of the resulting DNA extension products. Such DNA extension products can be less likely to be ligated. Primer extension can be conducted by suitable enzymes, including polymerases such as PolI, PolII, PolIII, Klenow, T4 DNA Pol, modified T7 DNA Pol, mutated modified T7 DNA Pol, TdT, Bst, Taq, Tth, Pfu, Pow, Vent, Pab, and Phi-29. For example, reactions can be conducted using Bst polymerase by incubating the template nucleic acid and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20). The dNTPs can have a small percentage of terminator nucleotides. DNA molecules, such as DNA fragments or DNA extension products prepared as described above, can then be stretched on a stretching substrate along with their template DNA molecules. The DNA on the stretching substrate can then be contacted with an immobilization substrate. The immobilization substrate can comprise a binding agent, such as avidin or streptavidin. The biotin can be used to bind the DNA molecules to the immobilization substrate via avidin or streptavidin binding. The stretching substrate and the immobilization substrate can be separated with the use of heat or other denaturing methods. The immobilization substrate can then be contacted with a primer substrate comprising positionally-encoded primers as described in this disclosure. Primers can be ligated to the DNA fragments or DNA extension products on the immobilization substrate to encode positional information with barcodes, or to add adaptors useful for sequencing library construction.

Extension Reactions

Once target polynucleotides are isolated and processed as provided herein, positional barcoded extension products can be generated from the target polynucleotides. In some cases, target polynucleotides processed as provided herein are stretched on a stretching substrate and contacted with primers on a primer array (e.g., template and/or recipient oligo array) prior to being subjected to primer extension reactions, as outlined in FIG. 1 and FIG. 2.

Figure 35:
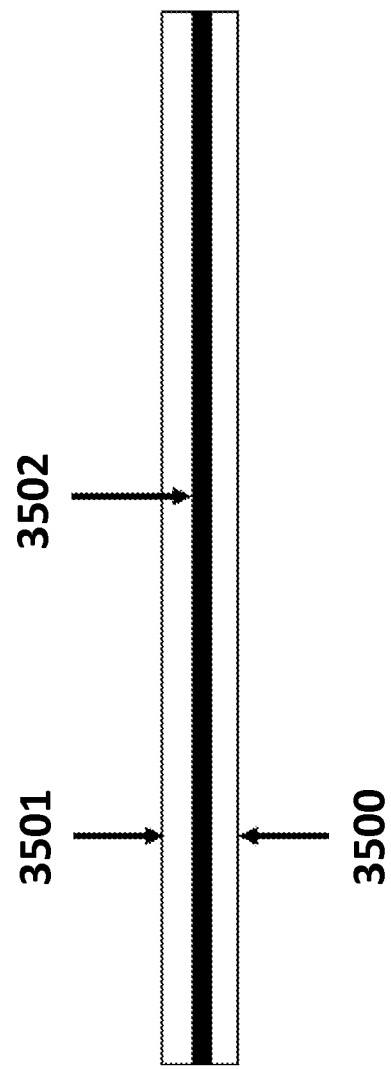
FIG. 35 illustrates a schematic of placement of a coverslip with combed nucleic acid onto a substrate with spatial encoding.

As shown in FIG. 35, a primer substrate 3500 comprising a gel surface coating 3502 can be brought into contact with a stretching substrate 3501 comprising stretched target polynucleotides. Alternatively, target polynucleotides can be stretched, immobilized on an immobilization substrate, and contacted with primers on a primer array (e.g., template and/or recipient oligo array). Alternatively, target polynucleotides can be stretched directly on a primer array (e.g., template and/or recipient oligo array) substrate. Primers on the primer array (e.g., template and/or recipient oligo array) can hybridize to primer binding sites introduced into target polynucleotides using the methods provided herein.

Extension reactions can be conducted to extend primers hybridized to a target polynucleotide using segments of the target polynucleotide as template. The target polynucleotide can be a stretched target polynucleotide. The primers hybridized to the target polynucleotide (e.g. stretched polynucleotide) can be non-substrate bound (i.e., free in solution) or substrate bound. In some cases, as outlined in FIG. 1 and FIG. 2, extension reactions are performed with primers bound to a primer array (e.g., template and/or recipient oligo array) to generate positionally-encoded extension products comprising sequence complementary to segments of the target polynucleotide 106, 206. The resulting extension products can remain bound to the primer array (e.g., template and/or recipient oligo array). The resulting extension products can comprise PCR primer sites, barcode sequences, and adaptor sequences present in the original array-bound primers as well as sequence complementary to a segment of the target polynucleotide.

In some cases, primers (e.g., oligo) on a primer array (e.g., template and/or recipient oligo array) hybridize or couple to stretched target polynucleotides at primer binding sites introduced into the target polynucleotides using the methods provided herein. The hybridized or coupled primers (e.g., oligos) can be used to conduct extension reactions. FIG. 36 depicts a multi-step process for generating extension products complementary to a target polynucleotide using a primer array (e.g., template and/or recipient oligo array) generated using the methods provided herein. In a first step, a non-array bound primer 3622 hybridizes to a target polynucleotide, which can be stretched prior to hybridization using any of the methods provided herein. Hybridization between the non-array bound primer 3622 and the target polynucleotide can be facilitated through a random sequence 3613 on the non-array bound primer 3622 and a sequence complementary to the random sequence 3613 on the target polynucleotide 3630. This is akin to the method depicted in FIG. 32. Following hybridization, the hybridized non-array bound primer 3622 can be extended using any of the polymerases provided herein using the target polynucleotide 3630 as template in order to generate extension products complementary to the target polynucleotide 3630. The non-array bound primer 3622 can further comprise a primer binding site 3612 such that the primer binding site 3612 does not hybridize to the target polynucleotide. The primer binding site 3612 can comprise defined sequence. The defined sequence can be universal, adaptor, PCR primer and/or barcode sequence. The primer binding site 3612 can comprise universal, adaptor, PCR primer and/or barcode sequence. The barcode sequence can encode positional information in a manner described herein. In some cases, the polymerase used comprises strand displacement activity. In some cases, the polymerase used does not comprise strand displacement activity. The extension products can be contacted with a primer array (e.g., template and/or recipient oligo array) 3600 comprising primer regions 3610, 3620. Each of the primer regions can comprise primers (e.g., oligos, 3621) bound to the primer array 3600 in one of the primer regions 3610, 3620. Each of the array-bound primers (e.g., oligos; 3621) can comprise sequence 3611 that is complementary to the primer binding site 3612 and can thus tether the extension products as provided to the substrate upon hybridization to the primer binding site 3612 to generate array-bound extension products 3614 as shown in FIG. 36. Alternatively, during the extension reaction in FIG. 36 template switching can occur from the free primer to the target polynucleotide, allowing the extension product to incorporate sequence complementary to a segment of target polynucleotide.

Figure 37:
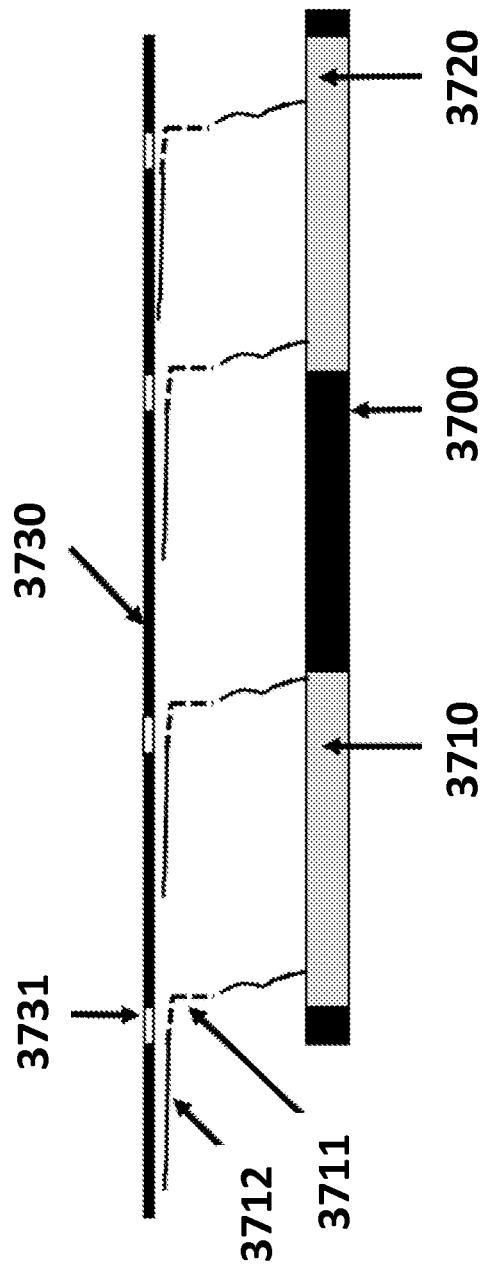
FIG. 37 illustrates a schematic of adding extendable sequences to long nucleic acid via transposon insertion using substrate features.

In some cases, extension products are generated from array-bound primers coupled to a target polynucleotide comprising primer binding sites introduced by transposon insertion as provided herein. For example, FIG. 37 depicts a primer substrate 3700 comprising primer regions 3710, 3720. Each of the primer regions 3710 and 3720 comprise primers (e.g., oligos) bound to the primer substrate 3700 such that each of the primers (e.g., oligos) are capable of binding to stretched target polynucleotide 3730 at a primer-binding site 3731 incorporated into the target polynucleotide 3730 using transposons as described herein and shown in FIG. 31. Subsequently, hybridized or coupled primers (e.g., oligos) are extended to generate array-bound extension products 3712. The primer binding site 3731 can comprise defined sequence. The defined sequence can be universal, adaptor, PCR primer and/or barcode sequence. The primer binding site 3731 can comprise universal, adaptor, PCR primer and/or barcode sequence. The barcode sequence can encode positional information in a manner described herein.

Extension reactions can be conducted with enzymes, such as any DNA polymerase as provided herein. The polymerase can include, but are not limited to, PolI, PolII, PolIII, Klenow, T4 DNA Pol, modified T7 DNA Pol, mutated modified T7 DNA Pol, TdT, Bst, Taq, Tth, Pfu, Pow, Vent, Pab, Phusion, and Phi-29. For example, extension reactions can be conducted using Bst polymerase by incubating the template nucleic acid and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20). Extension reactions can be conducted with reverse transcriptase enzymes. In some cases, the template nucleic acid comprises RNA, and enzymatic extension reactions elongate the primer using the RNA as template. Conducting extension reactions with array-bound primers and target polynucleotide can generate array-bound extension products, comprising sections of template nucleic acid sequence or its complement and a barcode tag sequence as provided herein.

Figure 38:
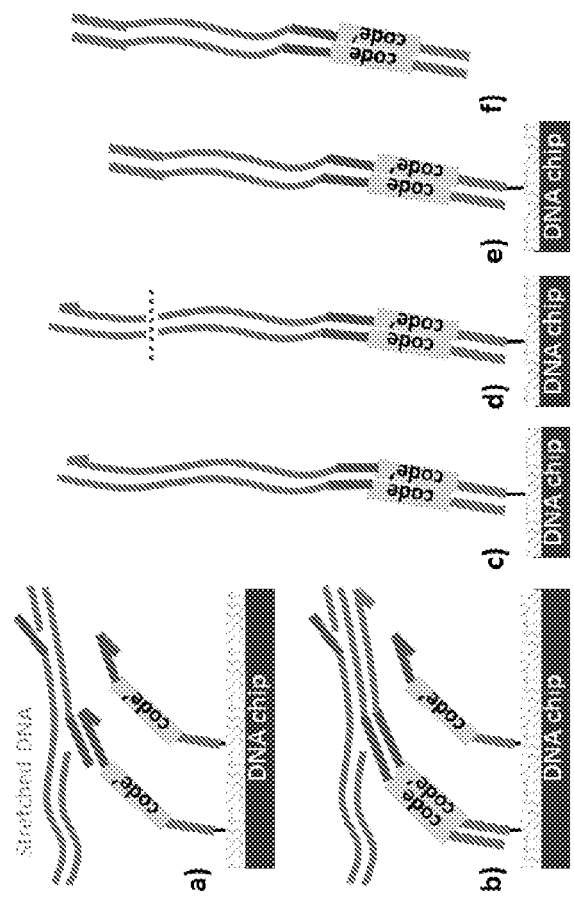
FIG. 38 illustrates steps a) through f) for the construction of a next-generation sequencing (NGS) library on an oligo chip (DNA Array). Step a) shows an immobilized oligo comprising a barcode hybridizing to a target polynucleotide (stretched DNA) stretched across the oligo array using molecular combing. Step b) shows extension and thereby copying of the combed target polynucleotide, resulting in a double stranded target polynucleotide (dsDNA). Step c)

In some cases, extension products are generated from array-bound primers on an array as provided herein coupled to a target polynucleotide comprising primer binding sites introduced by nicking the target polynucleotide using a nicking enzyme and subsequently appending the primer binding sites. The nicking enzyme can be any nicking enzymes as provided herein. In some cases, the nicking enzyme is Nt.CviPII. Appendage of the priming binding sites can be through ligation. Ligation can be any ligation method as described herein. Stretching of the target polynucleotide can be any stretching method provided herein. In some cases, a target polynucleotide is stretched using molecular combing. The target polynucleotide comprising appended primer binding sites can be stretched on an oligo array using molecular combing such that one or more primer binding sites comprise sequence complementary to an oligo on an oligo array. The oligo array can be prepared by the methods provided herein. The oligo array can be a template or recipient array. The recipient array can be generated using a transfer method as provided herein. The transfer method can be a face-to-face enzymatic transfer method as provided herein. In some cases, a primer binding site on a target polynucleotide stretched on an oligo array binds to an oligo comprising a complementary sequence such that the strand of the target polynucleotide comprising the bound primer binding site serves a template for extension using a polymerase of the oligo comprising the complementary sequence, thereby generating an array bound double stranded target polynucleotide. For example, FIG. 38 shows a target polynucleotide comprising priming binding sites introduced by a nicking enzyme and appendage of the primer binding sites and subsequently stretched across an oligo array as fabricated by the methods provided herein. FIG. 38 step a) shows an immobilized oligo comprising a barcode (code/code') on an oligo array hybridizing to a target polynucleotide (stretched DNA) stretched across the oligo array. Stretching of the target polynucleotide can through the use of molecular combing. The barcode can be a positional barcode as provided herein. FIG. 38 step b) shows extension and thereby copying of the target polynucleotide (stretched DNA), resulting in a double stranded target polynucleotide (dsDNA) immobilized on the oligo array (FIG. 38 step c). Primer extension can be conducted with Vent exo⁻ polymerase, a thermostable enzyme, in the presence of modified nucleotides (labeled with fluorophores) which can serve to visually confirm polymerase extension. However, one of skill in the art can appreciate that any suitable polymerase enzyme as provided herein can be used. In some cases, a polymerase comprising strand displacing properties is used. The strand displacing polymerase can be Vent exo⁻ polymerase as well as phi29 and Bst. FIG. 38 step d) shows fragmentation of the double stranded target polynucleotide followed by end-repair. In some cases, fragmentation can be achieved through methods known in the art. Fragmentation can be through physical fragmentation methods and/or enzymatic fragmentation methods. Physical fragmentation methods can include nebulization, sonication, and/or hydrodynamic shearing. In some cases, the fragmentation can be accomplished mechanically comprising subjecting the nucleic acid to acoustic sonication. In some cases, the fragmentation comprises treating the nucleic acid with one or more enzymes under conditions suitable for the one or more enzymes to generate breaks in the double-stranded nucleic acid. Examples of enzymes useful in the generation of nucleic acid fragments include sequence specific and non-sequence specific nucleases. Non-limiting examples of nucleases include DNase I, Fragmentase, restriction endonucleases, variants thereof, and combinations thereof. Reagents for carrying out enzymatic fragmentation reactions are commercially available (e.g., from New England Biolabs). For example, digestion with DNase I can induce random double-stranded breaks in DNA in the absence of $Mg^{++}$ and in the presence of $Mn^{++}$. In some cases, fragmentation comprises treating the target polynucleotides with one or more restriction endonucleases. Fragmentation can produce fragments having 5' overhangs, 3' overhangs, blunt ends, or a combination thereof. In some cases, such as when fragmentation comprises the use of one or more restriction endonucleases, cleavage of the target polynucleotide leaves overhangs having a predictable sequence. In some cases, the fragmented double stranded target polynucleotide is end-repaired as provided herein, thereby generating blunt ends. In some cases, the fragmented double stranded target polynucleotide is end-repaired as provided herein and subsequently subjected to an A-tailing reaction as provided herein. FIG. 38 step e) shows appending of an adapter to the fragmented double stranded target polynucleotide followed by release of the double stranded target polynucleotide from the oligo array for sequencing in FIG. 38 step f). Release of the double stranded target polynucleotide from the oligo array can be accomplished by fragmentation of the double stranded target polynucleotide from the oligo array substrate. Fragmentation can be by the use of any of the methods provided herein. In some cases, the array-bound primers (oligos) preferably have a restriction site in their 5' or 3' end, which is incorporated into the double stranded target polynucleotide and allows for the selective cleavage and release of the double stranded target polynucleotide or part thereof. In some cases, the double stranded target polynucleotide is enzymatically cleaved using NEB fragmentase. In some cases, the bond between the double stranded target polynucleotide and the primer substrate can be broken with thermal energy. In some cases, the double stranded target polynucleotide can be detached from the primer substrate by mechanical breakage or shear. Appending of the adapter to the fragmented double stranded target polynucleotide can comprise ligation. Ligation can be through any method of ligation proved herein. In some cases, the adapter appended to the double stranded target polynucleotide comprises a sequence compatible with a next generation sequencing platform (NGS) as provided herein. In some cases, the sequencing platform is an Illumina platform. In some cases, the adapter appended to the double stranded target polynucleotide comprises an Illumina primer sequence for use in the Illumina HiSeq 2500. The Illumina primer sequence can be a second Illumina primer. The released double stranded target polynucleotide can be sequenced using any sequencing method known in the art. In some cases, the released double stranded target polynucleotide is sequenced using a NGS method. The NGS method can be any NGS method as provided herein.

Production of Sequencing Libraries from Extension Products

Once extension products are produced from the target polynucleotide, as described elsewhere in this disclosure, the extension products can be either sequenced directly or used to generate sequencing libraries for subsequent sequencing. In some cases, following processing of a target polynucleotide, stretching on an oligo array, and extension of the stretched target polynucleotide as provided herein, a nucleic acid library is produced. As outlined in FIG. 1 and FIG. 2, the nucleic acid library can be a sequencing library that can be produced from extension products 107, 207.

In some cases, prior to sequencing, extension products produced by the methods described herein are released from an oligo array. An example of this embodiment is shown in FIG. 38, step f). In some cases, the bond between the extension product and the primer substrate can be broken with thermal energy. In some cases, the extension product can be detached from the primer substrate by mechanical breakage or shear. In some cases, the array-bound primers (oligos) preferably have a restriction site in their 5' or 3' end, which is incorporated into the extension product and allows for the selective cleavage and release of the extension products or part thereof. In some cases, releasing an extension product from an oligo array can be via digestion of the extension product with an enzyme for fragmenting nucleic acids as provided herein. In some cases, an extension product is released from an oligo array by digestion with restriction enzymes. The restriction enzymes can be any restriction enzymes known in the art and/or provided herein. In some cases, the extension product is enzymatically cleaved using NEB fragmentase. The digestion time for enzymatic digestion of the extension products can be adjusted to obtain select fragment sizes. In some cases, the extension products can be fragmented into a population of fragmented extension products of one or more specific size range(s). In some cases, the fragments can have an average length from about 10 to about 10,000 nucleotides or base pairs. In some cases, the fragments have an average length from about 50 to about 2,000 nucleotides or base pairs. In some cases, the fragments have an average length from about 100 to about 2,500, about 10 to about 1000, about 10 to about 800, about 10 to about 500, about 50 to about 500, about 50 to about 250, or about 50 to about 150 nucleotides or base pairs. In some cases, the fragments have an average length less than 10,000 nucleotides or bp, less than 7,500 nucleotides or bp, less than 5,000 nucleotides or bp, less than 2,500 nucleotides or bp, less than 2,000 nucleotides or bp, less than 1,500 nucleotides or bp, less than 1,000 nucleotides or bp, less than 500 nucleotides or bp, less than 400 nucleotides or bp, less than 300 nucleotides or bp, less than 200 nucleotides or bp, or less than 150 nucleotides or bp. In some cases, the fragments have an average length of about, more than, less than, or at least 10, 20, 30, 40, 50, 60, 70, 80, 90, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, or 10,000 nucleotides or base pairs.

In some cases, polynucleotide fragments generated by fragmentation of extension products on an oligo array as generated by the methods provided herein are subjected to end repair. End repair can include the generation of blunt ends, non-blunt ends (i.e. sticky or cohesive ends), or single base overhangs such as the addition of a single dA nucleotide to the 3'-end of the double-stranded nucleic acid product by a polymerase lacking 3'-exonuclease activity. In some cases, end repair is performed on the fragments to produce blunt ends wherein the ends of the fragments contain 5' phosphates and 3' hydroxyls. End repair can be performed using any number of enzymes and/or methods known in the art. An overhang can comprise about, more than, less than, or at least 1, 2, 3, 4, 5, 6, 7, 8, 9, 10, 11, 12, 13, 14, 15, 16, 17, 18, 19, or 20 nucleotides.

In some cases, extension products generated by the methods provided herein and bound to an oligo array as provided herein, remain bound to the oligo array and a sequencing library is generated from the bound extension products. The generation of a sequencing library from oligo array bound extension products generated by the methods provided herein can be by generating a second set of extension products using the array-bound extension products as templates. These second extension products can comprise a sequence complementary to the barcode sequence. The sequence complementary to the barcode sequence can be correlated to the original barcode sequence and thereby convey the same positional information as the original barcode. The second extension products can also comprise a sequence corresponding to a region or segment of the target polynucleotide, as they can be complementary to the regions of the first extension products that can be complementary to the target polynucleotide from which the array bound extension products were generated In some cases, preparation of a sequencing library from oligo array bound extension products generated by the methods provided herein is performed by hybridizing non-substrate bound primers (i.e., primers in solution or "free" primers) to the array-bound extension products and extending the hybridized non-substrate bound primers using the array bound extension products as template to generate non-array bound (or free) extension products. The non-substrate bound primers can hybridize to the array-bound extension products, for example through a random sequence segment as described herein of the non-substrate bound primer (e.g., random hexamer, etc.). The random sequence can be at least 5, 6, 7, 8, 9, 10, 11, 12, 13, 14, or 15 base pairs or nucleotides. The random sequence can be at most 5, 6, 7, 8, 9, 10, 11, 12, 13, 14, or 15 base pairs or nucleotides. Free primers can comprise PCR primer sequences. PCR primer sequences can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 base pairs or nucleotides. PCR primer sequences can be at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 base pairs or nucleotides. The non-substrate bound primers can comprise adaptor sequences. The adaptor sequences can be compatible with any sequencing platforms known in the art. In some cases, the adaptor sequence comprises sequence compatible for use in Illumina NGS sequencing methods such as the Illumina HiSeq 2500 system. The adaptor sequences can be Y-shaped adaptor, or duplex or partial duplex adaptors. Extension of the non-substrate bound primers hybridized to the array bound extension products can be conducted with enzymes, such as DNA polymerase. The polymerase can include, but are not limited to, PolI, PolII, PolIII, Klenow, T4 DNA Pol, modified T7 DNA Pol, mutated modified T7 DNA Pol, TdT, Bst, Taq, Tth, Pfu, Pow, Vent, Pab, and Phi-29. For example, extension reactions can be conducted using Bst polymerase by incubating the template nucleic acid and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20).

An example of the preparation of a sequencing library from oligo array bound extension products using non-substrate bound primers is shown in FIG. 39. A primer array (e.g., template and/or recipient oligo array) 3900 can comprise primer (oligo) regions 3910, 3920 comprising array-bound extension products 3913. The array-bound extension products 3913 can comprise a PCR primer sequence 3911 and a barcode sequence 3912, and sequence corresponding to a target polynucleotide or its complement. Non-substrate bound primers can be added to bind to the array-bound extension products 3913, for example through binding of a random hexamer or random nonomer segment 3932 of the non-substrate bound primer, and can be used for extension reactions. Non-array bound extension product 3931 can be generated that contains sections of the array bound extension product as well as a barcode sequence or its complement. The non-substrate bound primer can comprise a tail segment 3933 that contains a defined sequence that is non-complementary to sequence in the array bound extension product and thus does not hybridize to the array bound extension product. The defined sequence can comprise universal, adaptor, and/or barcode sequence.

Non-array bound extension products generated by the methods provided herein (e.g., as depicted in FIG. 39) can comprise sequence corresponding to a segment of the target polynucleotide. That is, a non-array bound extension product can comprise sequence complementary to some or all of the segment of an array-bound extension product from which it was generated which can comprises sequence corresponding to or complementary to a segment of the target polynucleotide. A non-array bound extension product can comprise a barcode which comprises sequence complementary to the barcode sequence of the array-bound extension product. This complementary barcode can convey the same positional information conveyed by the original barcode sequence by correlating the complementary barcode sequence with the original barcode sequence. In a non-array bound extension product, the positional information conveyed by the barcode or complementary barcode can be correlated with the sequence corresponding to a segment of the target polynucleotide, thereby locating the segment of the target polynucleotide along the length of the stretched target polynucleotide molecule. Non-array bound extension products can comprise one or more PCR primer sequences. A non-array bound extension product can comprise a PCR primer sequence complementary to a PCR primer sequence in the array-bound extension product from which it was generated. A non-array bound extension product can comprise a PCR primer sequence from the non-array bound primer that was extended to generate the non-array bound extension product. Non-array bound extension products can comprise adaptor sequences, such as sequencing adaptors. In some cases, an adaptor sequence appended to a non-array bound extension product comprise sequence compatible for use in Illumina NGS sequencing methods such as the Illumina HiSeq 2500 system.

Extension products (non-array bound or released from an oligo array as described herein) or fragments thereof can be amplified and/or further analyzed such as by sequencing. The sequencing can be any sequencing methods known in the art. Amplification can be conducted by methods any amplification methods known in the art or provided herein. Amplification can be conducted with any enzyme as provided herein. For example, reactions can be conducted using Bst polymerase by incubating the template nucleic acid and primers with Bst polymerase and dNTPs at 65° C. in 1× Isothermal Amplification Buffer (e.g., 20 mM Tris-HCl, 10 mM $(NH_4)_2SO_4$, 50 mM KCl, 2 mM $MgSO_4$, and 0.1% Tween 20). Amplification can utilize PCR primer sites incorporated into the extension products, for example from the array-bound primers (oligos) and the non-substrate bound primers. Amplification can be used to incorporate adaptors, such as sequencing adaptors, into the amplified extension products. The sequencing adaptors can be compatible with any sequencing method known in the art.

Sequencing

Once prepared into a sequencing library, the extension products can be sequenced. Prior to sequencing, a prepared sequencing library bound to an oligo array can be released from the oligo array by either denaturation, selected cleavage, or PCR amplification. For example as outlined in FIG. 1 and FIG. 2, the sequencing library can be sequenced and the order and alignment of sequence reads can be determined with the use of positional barcode information 108, 208. Sequence reads from the extension products can be aligned or assembled into the target polynucleotide. Alignment or assembly can be aided by the positional information conveyed by the barcode sequences associated with each segment of target polynucleotide. The positional information conveyed by the barcode can be correlated with the sequence corresponding to a segment of the target polynucleotide, thereby locating the segment of the target polynucleotide along the length of the stretched target polynucleotide. The use of positional information can be especially beneficial when sequencing long nucleic acid molecules or nucleic acid molecules containing long repeat sequences, insertions, deletions, transpositions, or other features.

Sequencing of the sequencing library can be performed with any appropriate sequencing technology, including but not limited to single-molecule real-time (SMRT) sequencing, Polony sequencing, sequencing by ligation (e.g. SOLiD sequencing), reversible terminator sequencing, proton detection sequencing, ion semiconductor (e.g. Ion Torrent) sequencing, nanopore sequencing, electronic sequencing, pyrosequencing (e.g. 454), Maxam-Gilbert sequencing, chain termination (e.g. Sanger) sequencing, +S sequencing, or sequencing by synthesis (e.g. Illumina HiSeq).

Sequencing can be performed by single-molecule real-time (SMRT) sequencing (e.g. Pacific Biosciences) as described in U.S. Pat. Nos. 7,462,452; 7,476,504; 7,405,281; 7,170,050; 7,462,468; 7,476,503; 7,315,019; 7,302,146; 7,313,308; and U.S. Patent Application Publication Nos. US20090029385; US20090068655; US20090024331; and US20080206764, the disclosure of each of which is herein incorporated by references in its entirety. Nucleic acid inserts from libraries prepared using the methods described herein or extension products released from an oligo array can be immobilized in zero mode waveguide arrays. A single DNA polymerase enzyme can be affixed at the bottom of a zero-mode waveguide with a single target polynucleotide. Fluorescently-labeled nucleotides can be incorporated into nucleic acid synthesis, and the zero-mode waveguide can be used to detect the fluorescent dyes as they are cleaved from the nucleotides. This can allow real-time base-by-base measurement of the template nucleic acid sequence. The fluorescent labels are clipped off as part of the nucleotide incorporation. In some cases, circular templates are utilized to enable multiple reads on a single molecule.

Sequencing can be performed by Polony sequencing. For example, nucleic acid inserts from libraries prepared using the methods described herein or extension products released from an oligo array cancan be sheared into strands about 1 kb in length. These strands can be circularized and amplified with rolling circle amplification. Amplified circularized products can be digested, for example with MmeIIIs restriction enzyme, producing T30 fragments flanked by tags. Fragments can be amplified, for example with PCR, and formed into a library. Emulsion PCR can be conducted on the library with bead-bound primers and capture beads are used to enrich the beads with amplified DNA. Beads can then be isolated with centrifugation, bound in a monolayer to a substrate, and contacted with sequencing reagents. Fluorescently labeled degenerate nonamers and imaged, allowing measurement of fragment sequences, and fragment sequences can be assembled.

In some cases, the methods described herein can be useful for preparing released extension products or libraries whose inserts are sequenced by the sequencing by ligation methods commercialized by Applied Biosystems (e.g., SOLiD sequencing). Nucleic acid inserts from libraries prepared using the methods described herein or extension products released from an oligo array can be incorporated into a water in oil emulsion along with polystyrene beads and amplified by for example PCR. In some cases, alternative amplification methods can be employed in the water-in-oil emulsion such as any of the methods provided herein. The amplified product in each water microdroplet formed by the emulsion interact, bind, or hybridize with the one or more beads present in that microdroplet leading to beads with a plurality of amplified products of substantially one sequence. When the emulsion is broken, the beads float to the top of the sample and are placed onto an array. The methods can include a step of rendering the nucleic acid bound to the beads stranded or partially single stranded. Sequencing primers are then added along with a mixture of four different fluorescently labeled oligonucleotide probes. The probes bind specifically to the two bases in the polynucleotide to be sequenced immediately adjacent and 3' of the sequencing primer to determine which of the four bases are at those positions. After washing and reading the fluorescence signal form the first incorporated probe, a ligase is added. The ligase cleaves the oligonucleotide probe between the fifth and sixth bases, removing the fluorescent dye from the polynucleotide to be sequenced. The whole process is repeated using a different sequence primer, until all of the intervening positions in the sequence are imaged. The process allows the simultaneous reading of millions of DNA fragments in a 'massively parallel' manner. This 'sequence-by-ligation' technique uses probes that encode for two bases rather than just one allowing error recognition by signal mismatching, leading to increased base determination accuracy.

Sequencing can be performed by reversible terminator sequencing. For example, fluorescently-labeled reversible terminator-bound dNTPs can be incorporated into a nucleic acid product being formed from a template nucleic acid insert from a library prepared using the methods provided herein or extension products released from an oligo array. Fluorescently-labeled terminators can then be imaged and cleaved to allow for an additional cycle of incorporation and imaging. Fluorescent labels can indicate which bases were incorporated and the sequence of the template nucleic acids can be derived.

Another example of a sequencing technique that can be used in the methods described herein is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Nucleic acid inserts from libraries prepared using the methods described herein or extension products released from an oligo array can be introduced into the wells, e.g., a clonal population of single nucleic can be attached to a single bead, and the bead can be introduced into a well. To initiate sequencing of the nucleic acids on the beads, one type of deoxyribonucleotide (e.g., dATP, dCTP, dGTP, or dTTP) can be introduced into the wells. When one or more nucleotides are incorporated by DNA polymerase, protons (hydrogen ions) are released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors. Correlation between the species of dNTP added to the microwell with the detection of hydrogen ions can allow determination of the sequence of the target polynucleotides.

Another example of a sequencing technique that can be used in the methods described herein is nanopore sequencing (see e.g. Soni G V and Meller A. (2007) *Clin Chem* 53: 1996-2001). A nanopore can be a small hole of the order of 1 nanometer in diameter. Immersion of a nanopore in a conducting fluid and application of a potential across it can result in a slight electrical current due to conduction of ions through the nanopore. The amount of current that flows is sensitive to the size of the nanopore. As nucleic acid inserts from libraries prepared using the methods described herein or extension products released from an oligo array pass through a nanopore, each nucleotide on the nucleic acid insert or released extension product obstructs the nanopore to a different degree. Thus, the change in the current passing through the nanopore as the nucleic acid insert or released extension product passes through the nanopore can represent a reading of the nucleic acid insert or released extension product sequence.

Sequencing can be performed by pyrosequencing (e.g. 454) As described in Margulies et al., *Nature* (2005) 437: 376-380 (2005); and U.S. Pat. Nos. 7,244,559; 7,335,762; 7,211,390; 7,244,567; 7,264,929; and 7,323,305, the disclosure of each of which is herein incorporated by reference in its entirety. Nucleic acid inserts from libraries prepared using the methods described herein or extension products released from an oligo array can be immobilized onto beads, and compartmentalized in a water-in-oil emulsion suitable for amplification by PCR. In some cases, alternative amplification methods other than PCR can be employed in the water-in-oil emulsion such as any of the methods provided herein. When the emulsion is broken, amplified fragments remain bound to the beads. The methods can include a step of rendering the nucleic acid bound to the beads single stranded or partially single stranded. The beads can be enriched and loaded into wells of a fiber optic slide so that there is approximately 1 bead in each well. Nucleotides are flowed across and into the wells in a fixed order in the presence of polymerase, sulfhydrolase, and luciferase. Single species of dNTPs can be added to the reaction area. Incorporation of dNTPs can produce pyrophosphate (PPi), which can be converted to ATP by ATP sulfurylase. The ATP can then fuel luciferase to produce light which can be detected. Addition of nucleotides complementary to the target strand results in a chemiluminescent signal that is recorded such as by a camera. This allows monitoring of whether the added dNTP species is incorporated, and therefore allows analysis of the target polynucleotides. The combination of signal intensity and positional information generated across the plate allows software to determine the DNA sequence.

Sequencing can be performed by Maxam-Gilbert sequencing. For example, a nucleic acid insert from libraries prepared using the methods described herein or extension product released from an oligo array can be radioactively labeled at one 5' end of a double-stranded nucleic acid molecule. Chemical treatment can be used to generate breaks at a small fraction of nucleotide bases. Four different reactions can be used, each generating a break at a particular base or pair of bases (e.g., G, A+G, C, and C+T). The nucleic acid molecules can then be cleaved, generating fragments with a radiolabel on one end and a length dependent on the break site. Reaction products can then be separated on a gel and analyzed based on their length and presence of label. Reaction products can be ordered based on length, and the sequence of the target polynucleotide can be determined.

Sequencing can be performed by chain termination (e.g. Sanger) sequencing. For example, a nucleic acid inserts from libraries prepared using the methods described herein or extension products released from an oligo array can be amplified with polymerase, normal dNTPs, and modified ddNTPs which terminate strand elongation if incorporated into a nucleic acid strand. ddNTPs can be labeled (e.g., fluorescently or radioactively). Single species of ddNTPs can be added to an extension reaction of a template nucleic acid, along with all four species of dNTPs. Reaction products can then be separated on a gel and analyzed based on their length and presence of label. Reaction products can be ordered based on length, and the sequence of the template nucleic acid molecule can be determined.

Sequencing can be performed by sequencing by synthesis by the method commercialized by Illumina, as described U.S. Pat. Nos. 5,750,341; 6,306,597; and 5,969,119. Nucleic acid inserts from libraries prepared using the methods described herein or extension products released from an oligo array can then be denatured and the single-stranded amplified polynucleotides can be randomly attached to the inside surface of flow-cell channels. Unlabeled nucleotides can be added to initiate solid-phase bridge amplification to produce dense clusters of double-stranded DNA. To initiate the first base sequencing cycle, four labeled reversible terminators, primers, and DNA polymerase can be added. After laser excitation, fluorescence from each cluster on the flow cell is imaged. The identity of the first base for each cluster is then recorded. Cycles of sequencing can be performed to determine the fragment sequence one base at a time.

Sequencing can be performed by +S sequencing as described in WO2012134602, the disclosure of which is herein incorporated by reference. In some cases, +S sequencing is performed on nucleic acid inserts from libraries prepared using the methods described herein or extension products released from an oligo array as provided herein. The +S sequencing can entail repeated rounds of controlled extension and wash cycles. Similar to the pulse extension, the controlled extension can be performed by limiting the availability of nucleotides or by adding reversible terminator nucleotide(s). The limited extension can be carried out by using a nucleic acid polymerase and one or more sets of nucleotides. The one or more sets generally each comprise no more than three different nucleotides. In some cases, the one or more sets of nucleotides employed in +S sequencing comprise one to four nucleotides and at least one of the nucleotides is a reversible terminator nucleotide. The extending can be with more than one set of nucleotides, such as at least 1, 2, 3, or more sets. A set of nucleotides can comprise one, two or three different nucleotides. In some cases, the +S sequencing method further comprises obtaining one or more additional sequence reads, such as by repeating the steps of releasing a primer extension product from the template (e.g., nucleic acid inserts from libraries prepared using the methods described herein or extension products released from an oligo array); hybridizing an additional sequencing primer (or extension primer) to the template; generating an additional primer extension product by extending the additional sequencing primer through controlled extension; and sequencing one or more bases of the template by further extending the additional primer extension product to generate an additional primer extension product, thereby obtaining an additional sequence read. The additional sequencing primer can target the same or similar regions of the template. The sequencing of the template can be by extending the sequencing primer using any of the sequencing methods provided herein. In some cases, a washing step or nucleotide degradation step is performed prior to a subsequent addition of a set of nucleotides.

Bioinformatics and Software

After sequencing, the sequence data can be aligned. Each sequence read can be separated into primer/tag sequence information, based on the known designed sequences of the primers/tags, and target polynucleotide information. Alignment can be aided by the encoded positional barcode information associated with each piece of target polynucleotide through its primer/tag sequence. Sequencing of the sequencing library or released extension products can generate overlapping reads with the same or adjacent barcode sequences. For example, some extension products can be long enough to reach the next specific sequence site associated with the target polynucleotide. Use of barcode sequence information can group together likely overlapping reads, which can increase accuracy and reduce computational time or effort.

In some cases, sequence reads and associated barcode sequence information obtained by the methods provided herein are analyzed by software. The sequence reads can be short (e.g., <100 bps) or long sequence reads (e.g., >100 bps). The software can perform the steps of arranging sequence reads derived from the same template. These reads can be identified by, for example, searching for reads that have barcodes from the same or neighboring columns in an oligo array comprising spot or regions as provided herein. In some cases, only reads of a certain range of distance, horizontal rows, and/or vertical columns are considered as putatively from the same template. In reading the barcodes, the software can take into account potential sequencing (and other) errors based upon barcode design. The error can be barcodes with edit distance four allows certain errors. In some cases, if a barcode contains too many errors and cannot be uniquely identified, its associate read is not directly used to assemble a sequence. While many reads can be assembled based upon relative barcode position (e.g., row numbers), some gaps can be filled by aligning reads coming from the same genomic region. One of skill in the art would appreciate that the software product can string reads together based upon barcode and can account for orientation of stretching of the target polynucleotide on an oligo array as provided herein.

For example, if DNA molecules are not strictly vertical after stretching on the DNA array, the orientation of the DNA molecules relative to the barcode columns can be analyzed by, for example, a known reference DNA sample that is spiked in. This reference DNA sample can be used to detect the relative angle of stretching, assuming the angle of stretching is similar to all the DNA molecules. For assembly of sequence reads based on comparison to a reference DNA sample (e.g. genome), such as in re-sequencing, software useful for re-sequencing assembly can be used. The software used can be compatible with the type of sequencing platform used. If sequencing is done with an Illumnia system, software packages such as Partek, Bowtie, Stampy, SHRiMP2, SNP-o-matic, BWA, BWA-MEM, CLC workstation, Mosaik, Novoalign, Tophat, Splicemap, MapSplice, Abmapper. ERNE-map (rNA), and mrsFAST-Ultra can be used. For SOliD based NGS sequencing, Bfast, Partek, Mosaik, BWA, Bowtie, and CLC workstation can be used. For 454 based sequencing, Partek, Mosaic, BWA, CLC workstation, GSMapper, SSAHA2, BLAT, BWA-SW, and BWA-MEM can be used. For Ion torrent based sequencing, Partek, Mosaic, CLC workstation, TMAP, BWA-SW, and BWA-MEM can be used. For de novo assembly of sequence reads obtained from the methods provided herein, any alignment software known in the art can be used. The software used can use an overlap layout approach for longer reads (i.e., >100 bps) or a de Bruijn graph based k-mer based approach for shorter reads (i.e., <100 bp reads). The software used for de novo assembly can be publically available software (e.g., ABySS, Trans-ABySS, Trinity, Ray, Contrail) or commercial software (e.g., CLCbio Genomics Workbench).

The above description discloses several methods and systems of the present invention. This invention is susceptible to modifications in the methods and materials, as well as alterations in the fabrication methods and equipment. Such modifications will become apparent to those skilled in the art from a consideration of this disclosure or practice of the invention disclosed herein. For example, the invention has been exemplified using nucleic acids but can be applied to other polymers as well. Consequently, it is not intended that this invention be limited to the specific embodiments disclosed herein, but that it cover all modifications and alternatives coming within the true scope and spirit of the invention.

Applications and Advantages

In some cases, the devices and methods described herein can be useful for sequencing long nucleic acid molecules such as DNA or RNA molecules. For example, E. coli has a genome of approximately 4.6 Mb, which can be sequenced in one process. Sequencing larger segments of DNA or RNA, for example 50 kb or 100 kb, can accurately characterize some repeating sequences and larger structural changes, but can mischaracterize structural changes on the order of megabases. The devices and methods described herein can more accurately characterize repeating sequences, larger structural changes, and megabase-scale structural changes. The nucleic acid molecules sequenced can be entire genomes, for example E. coli genomes. The nucleic acid molecules sequenced can be very long strands of human DNA or chromosome.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1—Production of a Flat Surface Array

Initiator silanes of the structure shown in FIG. 40 are bound to a flat silica substrate in the presence of EtOH, forming di-podal surface polymer initiation sites. A mixture of acrylamide and ethoxylated acrylamide, together with acrydite-modified oligonucleotides, undergoes atom-transfer radical polymerization (ATRP) on the substrate in the presence of CuBr, PMDETA, and $H_2O$. This forms a covalently-bonded, lightly-crosslinked polyacrylamide surface coating bound to the surface initiator sites, with thickness between about 50 nm and about 200 nm, with oligonucleotides incorporated into the structure. This process is depicted in FIG. 43.

Example 2—Use of a Flat Surface Array in Sequencing

A polyacrylamide coated substrate is prepared as described in Example 1. DNA to be sequenced is bound to the oligonucleotides incorporated into the polymer structure. Sequencing by synthesis reagents are added to the substrate and sequencing by synthesis is performed for 40 cycles. At least 90% of polymer chains remain intact and bonded to the surface.

Example 3—Enzymatic Transfer of Template Via Single Extension Silanation of Gel-Chip Surfaces Preparation of Array Surfaces Glass slides were cleaned overnight in NanoStrip solution, rinsed with deionized (DI) water, and dried with $N_2$. The surface was then functionalized with acrylamide monomers which bind a polyacrylamide gel to the surface. A silanation solution was prepared with 475 mL ethanol, 25 mL deionized water, and 26 mL (3-acrylamidopropyl) trimethoxysilane, for a 5% v/v final concentration of silane. A rack of cleaned and dried glass slides were submerged in the silanation solution and agitated gently at room temperature for 5 hours. Slides were subsequently placed in a fresh ethanol bath a total of five times. Slides were then rinsed in a deionized water bath and dried with $N_2$. Slides were stored in a desiccated chamber until further use.

Preparation of Acrylamide Gel Mix

A 12% acrylamide gel mix was prepared with 5.00 mL of $H_2O$, 1.00 mg gelatin, 600.00 mg acrylamide, and 32.00 mg bis-acrylamide. The components were dissolved and mixed together for a final concentration of 12% acrylamide gel mix. For a 6% gel chip, 50 µL of 12% acrylamide gel mix, 45 µL of deionized water, and µL of 5'-acrydite-FC1 (1 mM concentration) functionalized oligonucleotides were combined for a total volume of 50 µL and vortexed.

Polymerization of Thin Gels

To the mix for a 6% gel chip prepared above, 1.3 µL of 5% ammonium persulfate per 100 µL reaction mix and 1.3 µL of 5% TEMED per 100 µL reaction mix were added as activators, for a final activator concentration of 0.065% each. The mixture was then vortexed. 15 µL of the gel mix was pipetted onto a clean flat surface, for example a glass slide or a silicon wafer. The gel mix on the surface was covered with a gel-chip glass slide surface as prepared in above, face down. The glass chip was pressed down to achieve a more uniform spread of the gel mix. The gel was allowed to polymerize at room temperature for 20 minutes. The gel was bound to the chips and the gel-chip substrates were removed from the clean flat surface, with the aid of a razor blade or other implement if necessary. Gel chips were rinsed in deionized water and excess gel from the chip edges was removed. Gel chips can be used immediately or stored in 4× saline-sodium citrate (SSC) buffer.

Preparation of Enzyme Mix

Enzyme mix was prepared with 37 µL of $H_2O$, 5 µL of 10× Thermopol buffer, 5 µL of BSA (10 mg/mL), 1 µL of dNTPs (10 mM), and 2 µL Bst DNA polymerase enzyme (8 U/µL).

Enzymatic Transfer of Template Via Single Extension

18 µL of enzyme mix as prepared above was placed on top of the prepared gel chip. The enzyme mix solution was allowed to permeate into the gel for 30 seconds. The gel chip was then placed face down onto a template chip. The template chip surface is prepared as in Example 1. A piece of PDMS was placed on top of the two chips as a compliant layer, and the chip stack was placed into a clamp, such as an aluminum clamp. The chip stack was incubated at 55° C. for 2 hours in a humidity chamber. Then, extra 4× saline-sodium citrate (SSC) buffer was added around the edges of the chip stack and allowed to soak in to loosen the gel chip. The gel chip surface and template chip surface were then pulled apart, with the aid of a razor blade or other implement if necessary. The gel remained bound to the gel chip, with transferred oligonucleotides. The template chip was washed in deionized water and dried with $N_2$. The gel chip was washed three times with 4×SSC buffer and three times with 2×SSC buffer.

Imaging of the Transferred Pattern

FC2QC-Cy3 oligonucleotides were hybridized for 35 minutes at 55° C. to a template chip as used in above. After hybridization, the template chip was rinsed and imaged. SP2-Cy3 oligonucleotides were hybridized for 30 minutes at 55° C. to a gel chip with transferred oligonucleotides as prepared in above. The gel chip was then rinsed twice with 4×SSC buffer and twice with 2×SSC buffer, and let to soak in 4×SSC buffer for 3 hours to reduce background signal. Rather than soaking for 3 hours, the gel chip could alternatively have been shaken for 20 minutes in 4×SSC buffer. The gel chip was then imaged under an epi-fluorescence microscope at desired magnifications, such as 10× and 40×. The gel chip was then stripped and hybridized with FC2QC-Cy3 oligonucleotides as for the template chip. The gel chip was then reimaged, and signal indicating physical transfer of template molecules was observed.

Preparation of Reaction Buffer for Template Amplification by Ingredient Volume

Reaction buffer was prepared with 1.5 mL of 10×Taq buffer, 750 µL of 100% DMSO, 3 mL of 5 M Betaine, 120 µL of 25 mM dNTPs, 75 µL of 5000 U/mL Taq polymerase, and 9.555 mL nuclease-free $H_2O$.

Preparation of Reaction Buffer for Template Amplification by Final Concentration Reaction buffer was prepared with a final concentration of 1×Taq buffer, 5% DMSO, 1 M Betaine, 0.2 mM dNTPs, 25 U/mL Taq polymerase, in nuclease-free $H_2O$.

Template Amplification Via Thermal Cycling

A gel chip with oligonucleotides was washed with 0.3× SSC buffer with 0.1% Tween-20 added. The gel chip then underwent 50 cycles of immersion into solution baths as follows: a) 45 seconds in 0.3×SSC buffer with 0.1% Tween- 20 at 94° C., b) 2 minutes in 5×SSC buffer with 0.1% Tween-20 at 60° C., and c) 1 minute in reaction buffer, prepared as per above, at 72° C. The template on the gel chip was amplified.

Probe Hybridization on a Chip

A chip to be imaged with double stranded DNA (dsDNA) was placed in 0.1 N NaOH solution for 3 minutes to denature the DNA. After washing, the chip was washed with 4×SSC buffer. The chip was then incubated for 40 minutes at 55° C. with 20 mL of 100 nM fluorescently-labeled hybridizing probe solution on a nutator. After the incubation, the chip was washed twice with 4×SSC buffer and twice with 2×SSC buffer for 20 minutes per wash step. The chip was then imaged.

Example 4—From Photo-Directed 3'-5' Array to 5'-3' Full Length Array

Via standard photo-directed synthesis, a template microarray is fabricated with 3'-5' oligonucleotide features, with the oligonucleotides containing an adaptor 1 sequence, a probe sequence that varies between features, and an adaptor 2 sequence. The template oligonucleotides are hybridized with a primer complementary to adaptor 1 which also contains an immobilizable linker. Primer extension reactions are conducted with polymerase. A first recipient array surface is brought into contact with the template array and the linkers are bound to its surface. The two surfaces are separated, and the recipient array contains both partial length and full length products in 5'-3' orientation. The oligonucleotides are hybridized with a primer complementary to adaptor 2 which also contains an immobilizable linker. Primer extension reactions are conducted with polymerase. A second recipient array surface is brought into contact with the first recipient (now template) array and the linkers are bound to its surface. The two surfaces are separated, and the second recipient array contains mostly full length products in 5'-3' orientation.

Example 5—Tagging and Sequencing a Long DNA Molecule with Binding Primers

A solution of DNA extract is prepared, comprising long pieces of template DNA molecules, approximately 4 Mb long. The template DNA is stretched by molecular combing onto a glass slide comprising nanochannel features. Free primers are added to the stretched template DNA molecules, each free primer comprising a random hexamer sequence and a primer binding site sequence. Free primers bind via their random hexamer regions at different locations along the template DNA molecules. A substrate with a gel coating is provided, the gel coating comprising a spatially-defined array of bound primers. Each array-bound primer has an adaptor sequence complementary to the primer-binding site sequence, a nucleic acid amplification primer sequence, and a barcode sequence, with all the primers in a given array spot sharing a barcode sequence unique to that region. The adaptor sequences hybridize to the primer-binding site sequences. Extension reactions are conducted to generate copies of regions (fragments) of the template DNA molecule, with the extension reaction beginning at the nucleic acid amplification primer sequences on the array-bound primers, and incorporating the barcode sequence into the resulting extension product. Array-bound extension products containing barcode sequences and sequences complementary to regions of the template DNA molecules are produced. Extension products are assembled into a sequencing library and sequenced. Alignment and assembly of the sequence reads is aided by the barcode information, and a complete 4 Mb template DNA sequence is produced.

Example 6—Tagging and Sequencing a Long DNA Molecule with Transposon Sites

A solution of DNA extract is prepared, comprising long pieces of template DNA molecules, approximately 4 Mb long. Primer binding sites are added to the template DNA molecules by transposon integration at an average spacing of 500 bp. The template DNA is stretched by molecular combing onto a glass slide (a first substrate) comprising nanochannel features. A second substrate with a gel coating is provided. The gel coating comprises a spatially-defined array of bound primers. Each array-bound primer has an adaptor sequence complementary to the primer-binding site sequence, a nucleic acid amplification primer sequence (e.g., PCR primer sequence), and a barcode sequence. All of the primers in a given array spot or region share a barcode sequence unique to that region. The array-bound primers hybridize to the primer binding sites previously integrated into the template DNA molecule. Extension reactions are conducted to generate multiple copies of regions of the template DNA molecules (or complements thereto), beginning at the 5' end with the nucleic acid amplification (e.g., PCR) primer sequences of the array-bound primers, next incorporating the barcode sequence, next incorporating the primer binding site sequence, and then extending to incorporate template nucleic acid sequence into the resulting extension product. Thus, array-bound extension products comprising barcode sequences and sequences complementary to regions of the template DNA molecules are produced. Extension products are assembled into a sequencing library and sequenced. Alignment and assembly of the sequence reads is aided by the barcode information, and a complete 4 Mb template DNA sequence is produced.

Example 7—PCR Amplification of Extension Products

A primer substrate comprising array-bound primer regions is used to generate an array of extension products. Each extension product comprises a portion of nucleic acid complementary to a template nucleic acid molecule, as well as a PCR primer sequence and a positionally-encoded barcode sequence. The barcode sequences are the same for all products in a given array spot or region. PCR primers are introduced which hybridize with the extension products, at the PCR primer sequence at one end and via a random hexamer binding sequence at the other end. PCR is conducted to amplify the extension products. PCR amplification products comprising template nucleic acid sequence and a sequence complementary to the barcode sequence are sequenced. Sequence reads are aligned with the help of the positional barcode information.

Example 8—Tagging and Sequencing an RNA Molecule

A solution of RNA extract is prepared comprising pieces of RNA molecules. The RNA is stretched by molecular combing onto a glass slide comprising nanochannel features. Free (i.e., non-array bound) primers are added to the stretched RNA molecules, each free primer includes a random hexamer sequence and a primer-binding site sequence. Free primers hybridize via their random hexamer regions at different locations along the stretched RNA molecules. A substrate with a gel coating prepared as described in Example 1 is provided, the gel coating includes a spatially-defined array of primers adhered to the array surface at their 5' ends. Each array-bound primer has from 3' to 5' an adaptor sequence complementary to the primer-binding site sequence on the free primer, a barcode sequence, and a nucleic acid amplification primer sequence, with all the primers in a given array spot or region sharing a positional barcode sequence unique to that region. The adaptor sequences hybridize to the primer-binding site sequences of the free primers that are hybridized to the RNA molecules. Extension reactions are conducted with reverse transcriptase to generate copies of regions or fragments of the RNA molecule. The extension reactions begin at the nucleic acid amplification primer sequences on the primers, and incorporating the barcode sequence into the resulting extension product. Extension products containing barcode sequences and sequences complementary to regions of the RNA molecules are produced and are bound to the substrate. Extension products are assembled into a sequencing library. To generate a sequencing library, non-substrate bound primers are added to bind to the array-bound extension products and are used for extension reactions. Non-array bound extension product are generated that contains section of the array bound extension product as well as a barcode sequence or its complement. The non-substrate bound primers comprise a tail segment that contains a defined sequence that is non-complementary to sequence in the array bound extension product and thus does not hybridize to the array bound extension product. The defined sequence comprises adaptor and amplification primer sequences compatible with an Illumina NGS sequencing system. Thus the non-array bound extension products comprise sequences for use in the Illumina HiSeq 2500 system and are therefore sequenced using the Illumina HiSeq 2500 system.

Alignment and assembly of the sequence reads is aided by the barcode information, and a complete RNA sequence is produced by assembling the sequence reads in silico. For sequence reads obtained from new genes, software useful for de novo assembly is used. The software used for de novo assembly is publically available software (e.g., ABySS, Trans-ABySS, Trinity, Ray, Contrail) or commercial software (e.g., CLCbio Genomics Workbench). For sequence reads obtained from re-sequencing, software useful for re-sequencing assembly is used. The software used is compatible with the Illumnia system such as BWA, BWA-MEM, Novoalign, Tophat, Splicemap, MapSplice, Abmapper, or ERNE-map (rNA).

Example 9—Oligonucleotide Immobilization Transfer

An oligonucleotide immobilization transfer (OIT) is performed according to the following protocol:

Hybridize primer to template surface and extend: A) Incubate 200 uL of 500 nM Acr-FC1 primer in Grace hyb chamber at 55 C for 1 hour. B) Rinse with 4×SSC (2 times), 2×SSC (2 times). C) Extend the primer with Bst at 37 C for 10 mins in Grace Chamber (200 uL)+20 min at 55 C. Bst mix is prepared with 38 uL of $H_2O$, 5 uL of 10× Thermopol, 5 uL of BSA (10 mg/ml), 1 uL of dNTPs (10 mM), 1 uL of Bst (8 U/μl). D) Rinse with 4×SSC (2 times), 2×SSC (2 times)

Prepare Gel Mix at 2× concentration with: $H_2O$ (0.50 mL), Gelatin (0.10 mg), Acrylamide (60.00 mg), Bis-Acrylamide (3.20 mg). Prepare the master mix by combining 50 uL of 2× Acrylamide Mix and 50 uL of 2×SSC.

Activation of Acrylamide Gel (activator final conc.=0.065% each): A) Add 1.3 uL of 5% ammonium persulfate for each 100 uL reaction. B) Add 1.3 ul of 5% temed for each 100 uL reaction. C) Vortex.

Polymerization of Thin Gels: A) Pipette 20 uL of gel mix onto template glass. B) Cover template with silanated glass chip (receptor surface) face down, and press to get uniform bubble free spread. C) Allow to polymerize for 10-15 min.

Denaturation/Separation: A) Place bound chips in 1×TE bath and heat them to 65 C. B) Pull the surfaces apart with razor. The gel should stay on the Chip side.

Imaging: A) Denature any remaining Acr-FC1 from template surface in 0.1N NaOH for 3 min. B) Rinse with 4×SSC (3 times), 2×SSC (3 times). C) Hybridize SP2-Cy3 oligo (500 nM) at 55 C for 45 mins on the Chip side. Use the humidity chamber with concentrated NaCl solution (74% RH). D) Hybridize FC2-QC-Cy3 oligo (500 nM) at 55 C for 1 hour on the template side. E) Rinse with 4×SSC (3 times), 2×SSC (3 times). F) Image gel or template with epi-fluoresence microscope.

What is claimed is:
1. A method for sequencing a template nucleic acid molecule, comprising:
(a) contacting a stretched and primed template nucleic acid molecule with a substrate, the primed template nucleic acid molecule comprising one or more primer-binding sites, the substrate comprising primers immobilized thereon,
each primer comprising:
(i) a region complementary to a primer-binding site, and
(ii) a barcode sequence indicative of a physical position of the primer on the substrate;
(b) conducting extension reactions using the primers and the template nucleic acid molecule as a template, thereby generating extension products, each extension product comprises (i) sequence of a fragment of the template nucleic acid or complement of the fragment, and (ii) sequence of the barcode sequence or a complement thereof;
(c) sequencing the extension products to determine sequences of the fragments or complements thereof and barcode sequences or complements thereof; and
(d) assembling the sequences of the fragments using the barcode sequence to thereby determine sequence of the template nucleic acid molecule.

2. The method of claim 1, wherein the stretching is performed by molecular combing, molecular threading, transfer printing, magnetic tweezers, or optical tweezers.

3. The method of claim 1, wherein the stretching is performed by molecular combing, by molecular threading, by transfer printing, by magnetic tweezers, by optical tweezers, or in nanochannels.

4. The method of claim 1, wherein the substrate is glass, hydrophobic glass, or a polymer coating.

5. The method of claim 1, wherein the one or more primer-binding sites are introduced into the template nucleic acid molecule via transposon insertion.

6. The method of claim 1, wherein the one or more primer-binding sites are introduced into the template nucleic acid molecule via (i) enzymatic nicking of the template nucleic acid molecule by a nicking enzyme to cleave one strand of the template nucleic acid molecule, (ii) removing 5'-phosphate from the nicked strand of the templated nucleic acid molecule, and (iii) ligating the primer-binding site to 3'-end of the nicked strand of the template nucleic acid molecule.

7. The method of claim 1, wherein at least 100 of the extension products are aligned using the barcode sequence indicative of the physical position of the primer on the substrate.

8. The method of claim 1, further comprising, prior to (a): (a1) covalently bonding initiator species to a surface of the substrate; and (a2) conducting a surface initiated polymerization of a polymer from the initiator species, wherein the polymer comprises a plurality of polymer chains, wherein a fraction of the plurality of polymer chains comprise the primers.

9. The method of claim 8, wherein the surface is selected from the group consisting of glass, silica, titanium oxide aluminum oxide, indium tin oxide (ITO), silicon, polydimethylsiloxane (PDMS), polystyrene, polycyclic olefins, poly(methyl methacrylate) (PMMA), titanium, and gold.

10. The method of claim 8, wherein in (a2) the conducting the surface initiated polymerization comprises atom-transfer radical polymerization (ATRP).

11. The method of claim 8, wherein in (a2) the conducting the surface initiated polymerization comprises reversible addition fragmentation chain-transfer (RAFT).

12. A method for determining sequence of a template nucleic acid molecule, comprising:
  (a) contacting the template nucleic acid molecule with a plurality of probes immobilized on a surface of a nucleic acid probe array, each the probe being uniquely tagged based on its location on the nucleic acid probe array;
  (b) performing extension reactions at locations of probe:template contact points on the template nucleic acid molecule; and
  (c) using the tags to compile the sequence of the template nucleic acid molecule, wherein the method further comprises stretching the template nucleic acid molecule prior to (a).

13. The method of claim 12, wherein prior to (b) a plurality of primer-binding sites are incorporated into or attached to the template nucleic acid molecule.

14. The method of claim 13, wherein the plurality of probes are immobilized at different individually addressable locations on the surface, and wherein each probe comprises (i) a binding sequence having sequence complementarity with the primer-binding site, and (ii) a barcode sequence indicative of the addressable location for the probe, wherein the barcode sequence is different for different addressable location.

15. The method of claim 13, wherein the plurality of primer-binding sites are incorporated into or attached to the template nucleic acid on average every at least 200 bp along the template nucleic acid molecule.

16. The method of claim 13, wherein the plurality of primer-binding sites are attached to the template nucleic acid molecule via free primers, each the free primer comprises (i) the primer-binding site, and (ii) a random sequence having complementarity with part of the template nucleic acid molecule, wherein the free primers are not bound to the substrate of the nucleic acid probe array.

17. The method of claim 13, wherein the plurality of primer-binding sites are attached to the template nucleic acid molecule via (i) enzymatic nicking of the template nucleic acid molecule by a nicking enzyme to cleave one strand of the template nucleic acid molecule, (ii) removing 5'-phosphate from the nicked strand of the templated nucleic acid molecule, and (iii) ligating the primer-binding site to 3'-end of the nicked strand of the template nucleic acid molecule.

18. The method of claim 12, wherein the template nucleic acid molecule is more than 100,000 base pairs (bp) in length.

19. The method of claim 12, wherein the probes have a density of more than $10^8/cm^2$.

20. The method of claim 12, wherein the extension reactions produce a plurality of extension products, each the extension product comprising a first complementary sequence of a fragment of the template nucleic acid molecule and a second sequence indicative of the individually addressable location of corresponding probe.

* * * * *